US009107750B2

(12) United States Patent
Cartledge et al.

(10) Patent No.: US 9,107,750 B2
(45) Date of Patent: Aug. 18, 2015

(54) IMPLANTABLE DEVICES FOR CONTROLLING THE SIZE AND SHAPE OF AN ANATOMICAL STRUCTURE OR LUMEN

(75) Inventors: Richard G. Cartledge, Hollywood, FL (US); Leonard Y. Lee, New York, NY (US); James I. Fann, Los Altos, CA (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 426 days.

(21) Appl. No.: 12/522,089

(22) PCT Filed: Jan. 3, 2008
(Under 37 CFR 1.47)

(86) PCT No.: PCT/US2008/000014
§ 371 (c)(1),
(2), (4) Date: Apr. 9, 2010

(87) PCT Pub. No.: WO2008/085814
PCT Pub. Date: Jul. 17, 2008

(65) Prior Publication Data
US 2011/0066231 A1  Mar. 17, 2011

Related U.S. Application Data

(60) Provisional application No. 60/878,068, filed on Jan. 3, 2007.

(51) Int. Cl.
*A61F 2/24* (2006.01)
*A61B 17/064* (2006.01)
(Continued)

(52) U.S. Cl.
CPC ............. *A61F 2/2448* (2013.01); *A61B 17/068* (2013.01); *A61B 17/0644* (2013.01);
(Continued)

(58) Field of Classification Search
CPC ... A61F 2/2466; A61F 2/2445; A61F 2/2448; A61B 17/068; A61B 17/0644
USPC ............ 623/213, 2.37, 1.36, 2.11; 227/175.1; 600/37
See application file for complete search history.

(56) References Cited

U.S. PATENT DOCUMENTS 4,042,979 A   8/1977 Angell
4,489,446 A   12/1984 Reed
(Continued)

FOREIGN PATENT DOCUMENTS

EP   0495417 A1   7/1992
EP   1 554 990 A2  7/2005
(Continued)

OTHER PUBLICATIONS

U.S. Appl. No. 13/123,768.
(Continued)

*Primary Examiner* — Gregory Anderson
*Assistant Examiner* — Christina Lauer
(74) *Attorney, Agent, or Firm* — Lerner, David, Littenberg, Krumholz & Mentlik, LLP

(57) ABSTRACT

An implantable device system for controlling the dimensions of internal anatomic passages corrects physiologic dysfunctions resulting from a structural lumen which is either too large or too small. Implantable devices are disclosed which employ various mechanisms for adjusting and maintaining the size of an orifice to which they are attached. Systems permit the implants to be implanted using minimally invasive procedures and permit final adjustments to the dimensions of the implants after the resumption of normal flow of anatomic fluids in situ.

32 Claims, 36 Drawing Sheets

(51) Int. Cl.
    *A61B 17/068*     (2006.01)
    *A61B 17/00*     (2006.01)
    *A61B 17/06*     (2006.01)
    *A61F 2/30*     (2006.01)

(52) U.S. Cl.
    CPC ............ *A61F2/2445* (2013.01); *A61F 2/2466* (2013.01); *A61B 17/00234* (2013.01); *A61B 2017/00243* (2013.01); *A61B 2017/00455* (2013.01); *A61B 2017/00783* (2013.01); *A61B 2017/00862* (2013.01); *A61B 2017/0641* (2013.01); *A61B 2017/0647* (2013.01); *A61B 2017/0649* (2013.01); *A61B 2017/06071* (2013.01); *A61F 2002/30537* (2013.01); *A61F 2250/0004* (2013.01)

(56) References Cited

U.S. PATENT DOCUMENTS

| | | |
|---|---|---|
| 4,602,911 A | 7/1986 | Ahmadi et al. |
| 4,676,253 A | 6/1987 | Newman et al. |
| 5,064,431 A | 11/1991 | Gilbertson et al. |
| 5,102,417 A | 4/1992 | Palmaz |
| 5,119,674 A | 6/1992 | Nielsen |
| 5,201,880 A | 4/1993 | Wright et al. |
| 5,226,429 A | 7/1993 | Kuzmak |
| 5,243,976 A | 9/1993 | Ferek-Petric et al. |
| 5,306,296 A | 4/1994 | Wright et al. |
| 5,405,378 A | 4/1995 | Strecker |
| 5,411,552 A | 5/1995 | Andersen et al. |
| 5,423,851 A | 6/1995 | Samuels |
| 5,443,477 A | 8/1995 | Marin et al. |
| 5,522,884 A | 6/1996 | Wright |
| 5,593,424 A | 1/1997 | Northrup III |
| 5,601,604 A | 2/1997 | Vincent |
| 5,674,279 A | 10/1997 | Wright et al. |
| 5,702,419 A | 12/1997 | Berry et al. |
| 5,709,695 A | 1/1998 | Northrup, III |
| 5,709,701 A | 1/1998 | Parodi |
| 5,713,951 A | 2/1998 | Garrison et al. |
| 5,769,812 A | 6/1998 | Stevens et al. |
| 5,814,056 A | 9/1998 | Prosst et al. |
| 5,814,097 A | 9/1998 | Sterman et al. |
| 5,824,055 A | 10/1998 | Spiridigliozzi et al. |
| 5,908,435 A | 6/1999 | Samuels |
| 5,961,539 A | 10/1999 | Northrup, III et al. |
| 5,972,030 A | 10/1999 | Garrison et al. |
| 5,984,959 A | 11/1999 | Robertson et al. |
| 5,989,284 A | 11/1999 | Laufer |
| 6,067,991 A | 5/2000 | Forsell |
| 6,110,200 A | 8/2000 | Hinnenkamp |
| 6,120,525 A | 9/2000 | Westcott |
| 6,152,144 A | 11/2000 | Lesh et al. |
| 6,152,936 A | 11/2000 | Christy et al. |
| 6,168,616 B1 * | 1/2001 | Brown, III ................... 623/1.11 |
| 6,168,816 B1 | 1/2001 | Hammond |
| 6,183,512 B1 | 2/2001 | Howanec, Jr. et al. |
| 6,187,040 B1 | 2/2001 | Wright |
| 6,217,610 B1 | 4/2001 | Carpentier et al. |
| 6,231,561 B1 | 5/2001 | Frazier et al. |
| 6,235,040 B1 | 5/2001 | Chu et al. |
| 6,245,012 B1 | 6/2001 | Kleshinski |
| 6,269,819 B1 | 8/2001 | Oz et al. |
| 6,355,030 B1 | 3/2002 | Aldrich et al. |
| 6,368,348 B1 | 4/2002 | Gabbay |
| 6,402,781 B1 | 6/2002 | Langberg et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,464,707 B1 | 10/2002 | Bjerken |
| 6,470,892 B1 | 10/2002 | Forsell |
| 6,514,265 B2 | 2/2003 | Ho et al. |
| 6,524,338 B1 | 2/2003 | Gundry |
| 6,537,314 B2 | 3/2003 | Langberg et al. |
| 6,547,801 B1 | 4/2003 | Dargent et al. |
| 6,551,332 B1 | 4/2003 | Nguyen et al. |
| 6,564,805 B2 | 5/2003 | Garrison et al. |
| 6,569,198 B1 | 5/2003 | Wilson et al. |
| 6,607,541 B1 | 8/2003 | Gardiner et al. |
| 6,613,059 B2 | 9/2003 | Schaller et al. |
| 6,619,291 B2 | 9/2003 | Hlavka et al. |
| 6,629,534 B1 | 10/2003 | St. Goar et al. |
| 6,641,593 B1 | 11/2003 | Schaller et al. |
| 6,651,671 B1 | 11/2003 | Donlon et al. |
| 6,685,713 B1 | 2/2004 | Ahmed |
| 6,689,164 B1 | 2/2004 | Seguin |
| 6,706,065 B2 | 3/2004 | Langberg et al. |
| 6,709,456 B2 | 3/2004 | Langberg et al. |
| 6,716,243 B1 | 4/2004 | Colvin et al. |
| 6,723,038 B1 | 4/2004 | Schroeder et al. |
| 6,749,630 B2 | 6/2004 | McCarthy et al. |
| 6,767,362 B2 | 7/2004 | Schreck |
| 6,776,789 B2 | 8/2004 | Bryant et al. |
| 6,790,229 B1 | 9/2004 | Berreklouw |
| 6,793,673 B2 | 9/2004 | Kowalsky et al. |
| 6,797,002 B2 | 9/2004 | Spence et al. |
| 6,800,090 B2 | 10/2004 | Alferness et al. |
| 6,810,882 B2 | 11/2004 | Langberg et al. |
| 6,824,562 B2 | 11/2004 | Mathis et al. |
| 6,840,246 B2 | 1/2005 | Downing |
| 6,872,223 B2 | 3/2005 | Roberts et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,911,035 B1 | 6/2005 | Blomme |
| 6,921,407 B2 | 7/2005 | Nguyen et al. |
| 6,926,715 B1 | 8/2005 | Hauck et al. |
| 6,932,838 B2 | 8/2005 | Schwartz et al. |
| 6,942,694 B2 | 9/2005 | Liddicoat et al. |
| 6,974,476 B2 | 12/2005 | McGuckin, Jr. et al. |
| 6,986,738 B2 | 1/2006 | Glukhovsky et al. |
| 6,989,028 B2 | 1/2006 | Lashinski et al. |
| 7,011,082 B2 | 3/2006 | Husges |
| 7,011,682 B2 | 3/2006 | Lashinski et al. |
| 7,097,658 B2 | 8/2006 | Oktay |
| 7,169,141 B2 | 1/2007 | Brock et al. |
| 7,175,660 B2 | 2/2007 | Cartledge et al. |
| 7,179,225 B2 | 2/2007 | Shluzas et al. |
| 7,220,237 B2 | 5/2007 | Gannoe et al. |
| 7,258,701 B2 | 8/2007 | Aram et al. |
| 7,297,150 B2 | 11/2007 | Cartledge et al. |
| 7,329,280 B2 | 2/2008 | Bolling et al. |
| 7,361,190 B2 | 4/2008 | Shaoulian et al. |
| 7,377,916 B2 | 5/2008 | Rudko et al. |
| 7,381,219 B2 | 6/2008 | Salahieh et al. |
| 7,416,557 B2 | 8/2008 | Drasler et al. |
| 7,442,207 B2 | 10/2008 | Rafiee |
| 7,455,690 B2 | 11/2008 | Cartledge et al. |
| 7,527,647 B2 | 5/2009 | Spence |
| 7,655,040 B2 | 2/2010 | Douk et al. |
| 7,666,204 B2 | 2/2010 | Thornton et al. |
| 7,780,683 B2 | 8/2010 | Roue et al. |
| 7,815,676 B2 | 10/2010 | Greenberg |
| 7,842,098 B2 | 11/2010 | Rioux et al. |
| 8,226,707 B2 | 7/2012 | White |
| 8,236,049 B2 | 8/2012 | Rowe et al. |
| 8,241,351 B2 | 8/2012 | Cabiri |
| 8,449,605 B2 | 5/2013 | Lichtenstein et al. |
| 8,470,023 B2 | 6/2013 | Eidenschink et al. |
| 2001/0021874 A1 | 9/2001 | Carpentier et al. |
| 2001/0049558 A1 | 12/2001 | Liddicoat et al. |
| 2002/0007222 A1 | 1/2002 | Desai |
| 2002/0095175 A1 | 7/2002 | Brock et al. |
| 2002/0107540 A1 | 8/2002 | Whalen et al. |
| 2002/0128708 A1 | 9/2002 | Northrup et al. |
| 2002/0151961 A1 | 10/2002 | Lashinski et al. |
| 2002/0151967 A1 | 10/2002 | Mikus et al. |
| 2002/0169358 A1 | 11/2002 | Mortier et al. |
| 2002/0173841 A1 | 11/2002 | Ortiz et al. |
| 2003/0018358 A1 | 1/2003 | Saadat |
| 2003/0040791 A1 | 2/2003 | Oktay |
| 2003/0050649 A1 | 3/2003 | Brock et al. |
| 2003/0050693 A1 | 3/2003 | Quijano et al. |

(56) References Cited

U.S. PATENT DOCUMENTS

| | | |
|---|---|---|
| 2003/0074012 A1 | 4/2003 | Nguyen et al. |
| 2003/0083742 A1 | 5/2003 | Spence et al. |
| 2003/0093148 A1 | 5/2003 | Bolling et al. |
| 2003/0130730 A1 | 7/2003 | Cohn et al. |
| 2003/0130731 A1 | 7/2003 | Vidlund et al. |
| 2003/0191479 A1 | 10/2003 | Thornton |
| 2003/0199974 A1 | 10/2003 | Lee et al. |
| 2003/0229359 A1 | 12/2003 | Fortier |
| 2003/0233142 A1 | 12/2003 | Morales et al. |
| 2004/0011365 A1 | 1/2004 | Govari et al. |
| 2004/0019378 A1 | 1/2004 | Hlavka et al. |
| 2004/0030382 A1 | 2/2004 | St. Goar et al. |
| 2004/0068276 A1 | 4/2004 | Golden et al. |
| 2004/0088047 A1 | 5/2004 | Spence et al. |
| 2004/0111099 A1 | 6/2004 | Nguyen et al. |
| 2004/0127980 A1 | 7/2004 | Kowalsky et al. |
| 2004/0133147 A1 | 7/2004 | Woo |
| 2004/0138744 A1 | 7/2004 | Lashinski et al. |
| 2004/0148019 A1 | 7/2004 | Vidlund et al. |
| 2004/0148021 A1 | 7/2004 | Cartledge et al. |
| 2004/0153144 A1 | 8/2004 | Seguin |
| 2004/0153146 A1 | 8/2004 | Lashinski et al. |
| 2004/0153147 A1 | 8/2004 | Mathis |
| 2004/0161611 A1 | 8/2004 | Mueller et al. |
| 2004/0162611 A1 | 8/2004 | Marquez |
| 2004/0172046 A1 | 9/2004 | Hlavka et al. |
| 2004/0176840 A1 | 9/2004 | Langberg et al. |
| 2004/0181238 A1 | 9/2004 | Zarbatany et al. |
| 2004/0186566 A1 | 9/2004 | Hindrichs et al. |
| 2004/0193191 A1 | 9/2004 | Starksen et al. |
| 2004/0204760 A1 | 10/2004 | Fitz et al. |
| 2004/0225353 A1 | 11/2004 | McGuckin, Jr. et al. |
| 2004/0243153 A1 | 12/2004 | Liddicoat et al. |
| 2004/0243229 A1 | 12/2004 | Vidlund et al. |
| 2004/0249453 A1 | 12/2004 | Cartledge et al. |
| 2005/0060030 A1 | 3/2005 | Lashinski et al. |
| 2005/0065550 A1 | 3/2005 | Starksen et al. |
| 2005/0070999 A1 | 3/2005 | Spence |
| 2005/0075736 A1 | 4/2005 | Collazo |
| 2005/0107886 A1 | 5/2005 | Crabtree et al. |
| 2005/0119734 A1 | 6/2005 | Spence et al. |
| 2005/0119735 A1 | 6/2005 | Spence et al. |
| 2005/0131533 A1 | 6/2005 | Alfieri et al. |
| 2005/0143766 A1 | 6/2005 | Bachmann et al. |
| 2005/0149114 A1* | 7/2005 | Cartledge et al. ............ 606/213 |
| 2005/0192601 A1 | 9/2005 | Demarais |
| 2005/0216079 A1 | 9/2005 | MaCoviak |
| 2005/0222678 A1 | 10/2005 | Lashinski et al. |
| 2006/0058817 A1 | 3/2006 | Starksen et al. |
| 2006/0074485 A1 | 4/2006 | Realyvasquez |
| 2006/0100697 A1 | 5/2006 | Casanova |
| 2006/0106405 A1 | 5/2006 | Fann et al. |
| 2006/0135964 A1 | 6/2006 | Vesely |
| 2006/0241748 A1 | 10/2006 | Lee et al. |
| 2007/0016287 A1 | 1/2007 | Cartledge et al. |
| 2007/0051377 A1 | 3/2007 | Douk et al. |
| 2007/0118215 A1 | 5/2007 | Moaddeb |
| 2007/0233239 A1 | 10/2007 | Navia et al. |
| 2007/0244556 A1 | 10/2007 | Rafiee et al. |
| 2007/0250160 A1 | 10/2007 | Rafiee |
| 2007/0299543 A1 | 12/2007 | Cartledge et al. |
| 2008/0004697 A1 | 1/2008 | Lichtenstein et al. |
| 2008/0027483 A1 | 1/2008 | Cartledge et al. |
| 2008/0109076 A1 | 5/2008 | Cartledge et al. |
| 2008/0306586 A1 | 12/2008 | Cartledge et al. |
| 2009/0005760 A1 | 1/2009 | Cartledge et al. |
| 2009/0054974 A1 | 2/2009 | McGuckin, Jr. et al. |
| 2009/0062825 A1 | 3/2009 | Pool et al. |
| 2009/0125102 A1 | 5/2009 | Cartledge et al. |
| 2009/0210052 A1 | 8/2009 | Forster et al. |
| 2009/0234404 A1 | 9/2009 | Fitzgerald et al. |
| 2009/0248148 A1 | 10/2009 | Shaolian et al. |
| 2010/0161047 A1 | 6/2010 | Cabiri |
| 2010/0168835 A1 | 7/2010 | Dorn |
| 2010/0211166 A1 | 8/2010 | Miller et al. |
| 2010/0217385 A1 | 8/2010 | Thompson et al. |
| 2010/0305609 A1 | 12/2010 | Cartledge et al. |
| 2010/0331949 A1 | 12/2010 | Habib |
| 2011/0009956 A1 | 1/2011 | Cartledge et al. |
| 2011/0022168 A1 | 1/2011 | Cartledge |
| 2011/0093060 A1 | 4/2011 | Cartledge et al. |
| 2011/0093062 A1 | 4/2011 | Cartledge et al. |
| 2011/0118828 A1 | 5/2011 | Thompson |
| 2011/0196480 A1 | 8/2011 | Cartledge |
| 2011/0202130 A1 | 8/2011 | Cartledge et al. |
| 2011/0208283 A1 | 8/2011 | Rust |
| 2011/0208295 A1 | 8/2011 | Cartledge et al. |
| 2011/0257633 A1 | 10/2011 | Cartledge et al. |
| 2011/0257737 A1 | 10/2011 | Fogarty et al. |
| 2011/0264191 A1 | 10/2011 | Rothstein |
| 2012/0022633 A1 | 1/2012 | Olson et al. |
| 2012/0022640 A1 | 1/2012 | Gross et al. |
| 2012/0059458 A1 | 3/2012 | Buchbinder et al. |
| 2012/0123531 A1 | 5/2012 | Tsukashima et al. |
| 2012/0136436 A1 | 5/2012 | Cabiri et al. |
| 2012/0158115 A9 | 6/2012 | Arnault De La Menardiere et al. |
| 2012/0197379 A1 | 8/2012 | Laske et al. |
| 2012/0277842 A1 | 11/2012 | Kunis |
| 2013/0006352 A1 | 1/2013 | Yaron |
| 2013/0144371 A1 | 6/2013 | Kavteladze |
| 2013/0172977 A1 | 7/2013 | Forde et al. |

FOREIGN PATENT DOCUMENTS

| | | |
|---|---|---|
| EP | 1611868 A2 | 1/2006 |
| JP | 61013818 | 1/1986 |
| JP | 05-049655 | 3/1993 |
| JP | 10-503399 A | 3/1998 |
| JP | 3049359 B2 | 6/2000 |
| JP | 3180136 B2 | 4/2001 |
| JP | 3180136 B2 | 6/2001 |
| JP | 2002509448 A | 3/2002 |
| JP | 2002523172 A | 7/2002 |
| JP | 2002526194 A | 8/2002 |
| JP | 2003533275 A | 11/2003 |
| JP | 2004535851 A | 12/2004 |
| JP | 2005537067 A | 12/2005 |
| JP | 2006507104 A | 3/2006 |
| JP | 2006520651 A | 9/2006 |
| JP | 2006520670 A | 9/2006 |
| JP | 2007-502689 | 2/2007 |
| JP | 2008534086 A | 8/2008 |
| WO | 9101697 A1 | 2/1991 |
| WO | 9315690 A2 | 8/1993 |
| WO | 9603938 A1 | 2/1996 |
| WO | 97/16135 A1 | 5/1997 |
| WO | 9719655 A1 | 6/1997 |
| WO | 99/04730 A1 | 2/1999 |
| WO | 99/30647 A1 | 6/1999 |
| WO | 9960952 A1 | 12/1999 |
| WO | 00/03759 A2 | 1/2000 |
| WO | 0015158 A1 | 3/2000 |
| WO | 0016700 A1 | 3/2000 |
| WO | 01/26586 A1 | 4/2001 |
| WO | 01 50985 A1 | 7/2001 |
| WO | 2004/012583 A2 | 2/2004 |
| WO | 2004/019816 A2 | 3/2004 |
| WO | 2004019826 A1 | 3/2004 |
| WO | 2004047677 A2 | 6/2004 |
| WO | 2004/060217 A1 | 7/2004 |
| WO | 2004080336 A2 | 9/2004 |
| WO | 2004084746 A2 | 10/2004 |
| WO | 2004100803 | 11/2004 |
| WO | 2004/112585 A2 | 12/2004 |
| WO | 2004/112651 A2 | 12/2004 |
| WO | 2004/112658 A1 | 12/2004 |
| WO | 2005/007036 A1 | 1/2005 |
| WO | 2005/007037 A1 | 1/2005 |
| WO | 2005/007219 A2 | 1/2005 |
| WO | 2005009285 | 2/2005 |
| WO | 2005/025644 A2 | 3/2005 |
| WO | 2005018507 A2 | 3/2005 |
| WO | 2005/046488 A2 | 5/2005 |
| WO | 2005/055883 A1 | 6/2005 |

(56) References Cited

FOREIGN PATENT DOCUMENTS

| WO | 2005/062931 | A2 | 7/2005 |
|---|---|---|---|
| WO | 2005084592 | A2 | 9/2005 |
| WO | 2006/105084 | A2 | 10/2006 |
| WO | 2007/136783 | A2 | 11/2007 |
| WO | 2009/052509 | A1 | 4/2009 |
| WO | 2010/085649 | A1 | 7/2010 |
| WO | 2010/085659 | A1 | 7/2010 |

OTHER PUBLICATIONS

Extended European Search Report for Application No. EP13166640 dated Jul. 1, 2013.
Extended European Search Report for Application No. 10733913 dated Dec. 11, 2012.
International Search Report for Application No. PCT/US07/11961 dated Aug. 25, 2008.
International Search Report for Application No. PCT/US2008/000014 dated Jul. 2, 2008.
Letter dated Jan. 27, 2011 from Richard H. Levinstein, Esq.
Canadian Office Action for Application No. 2,674,485 dated Dec. 12, 2013.
Japanese Office Action for Application No. 2011-548135 dated Dec. 6, 2013.
Supplementary European Search Report for Application No. EP 08712925 dated Feb. 26, 2014.

* cited by examiner

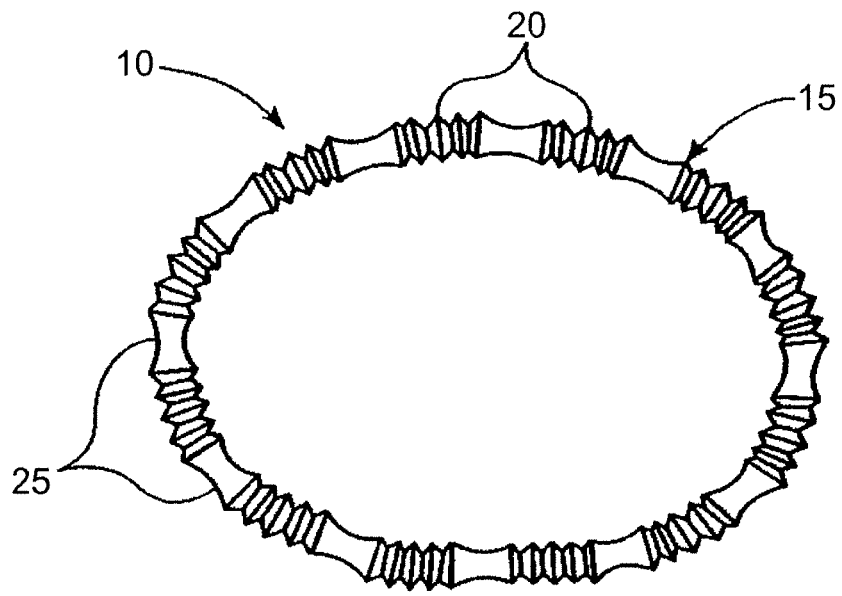
FIG. 1
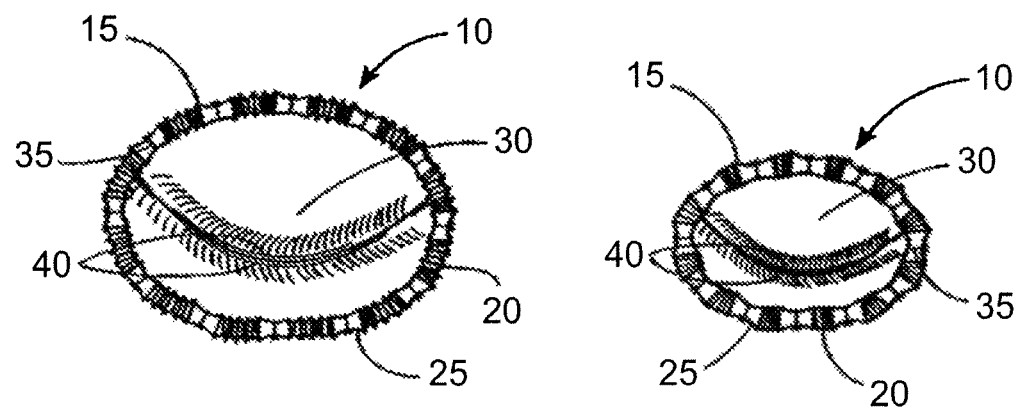
FIG. 2  FIG. 3

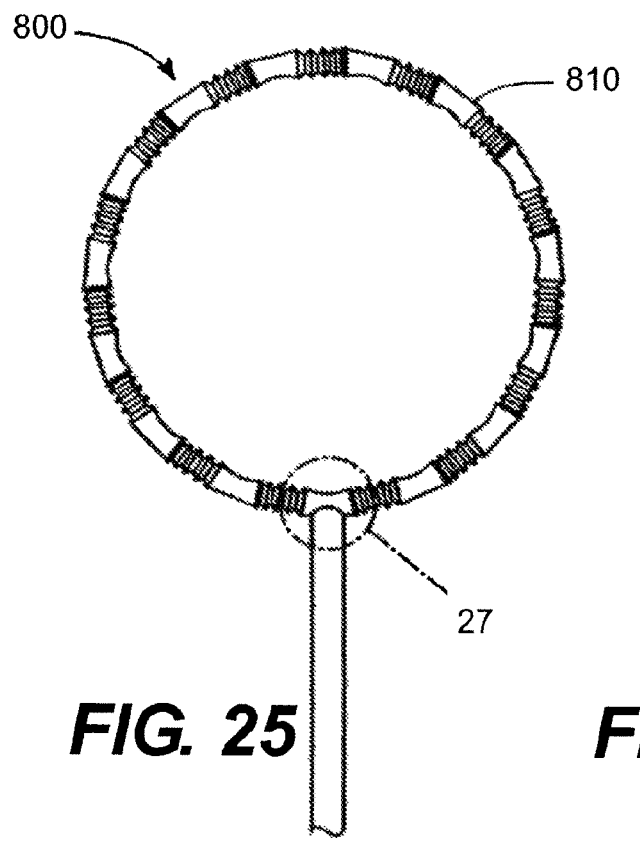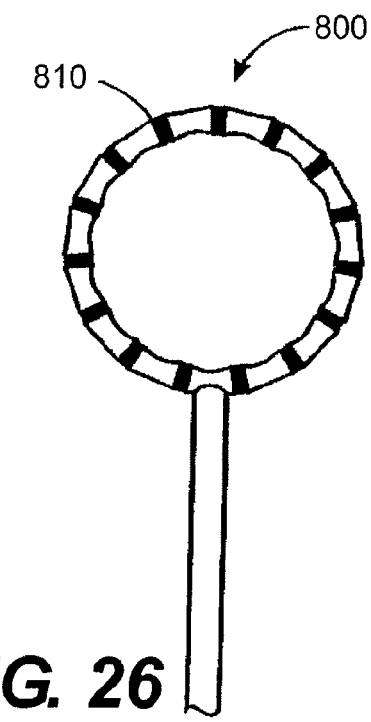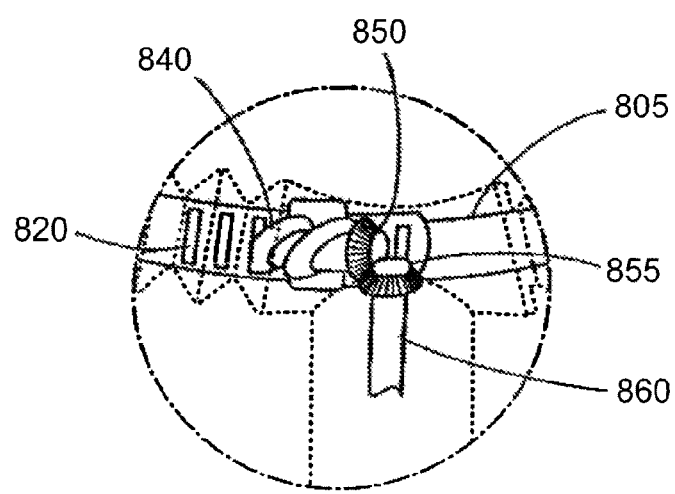

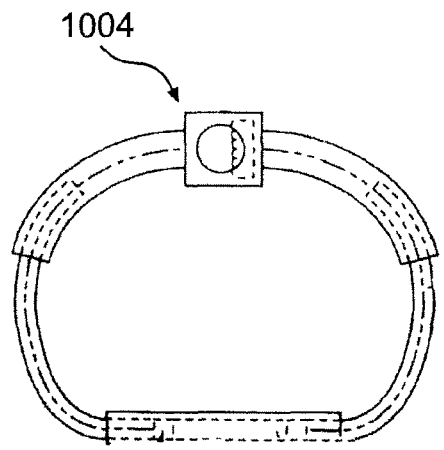
FIG. 33
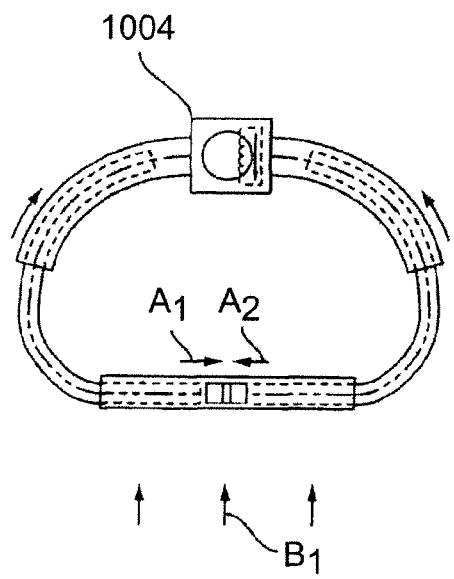 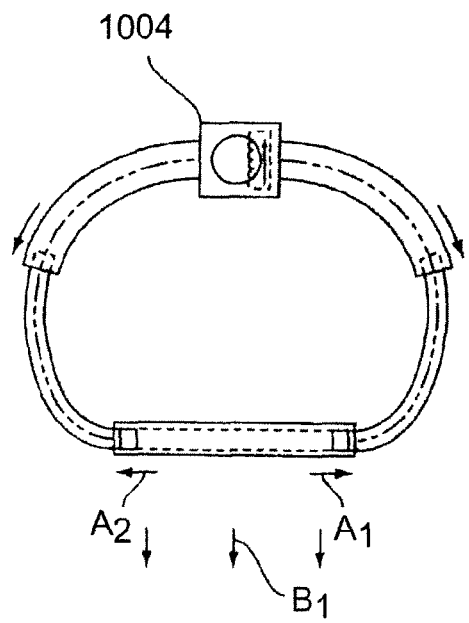
FIG. 34  FIG. 35

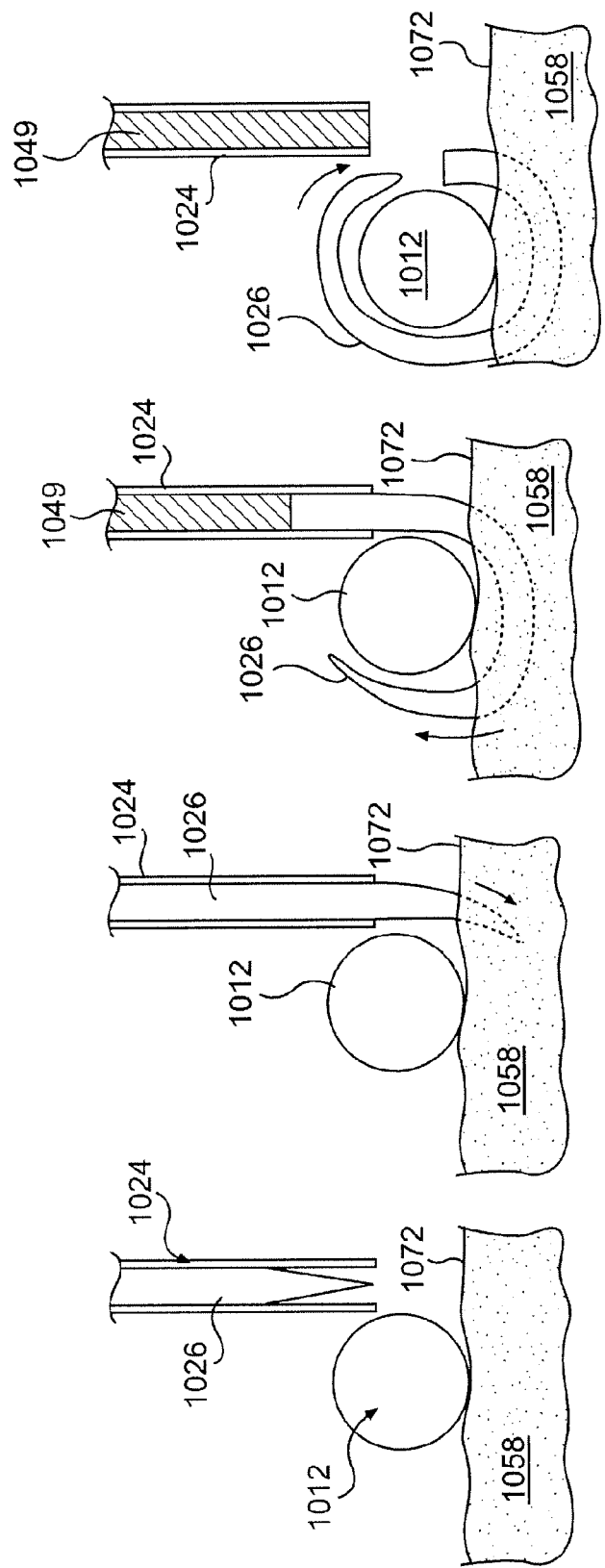

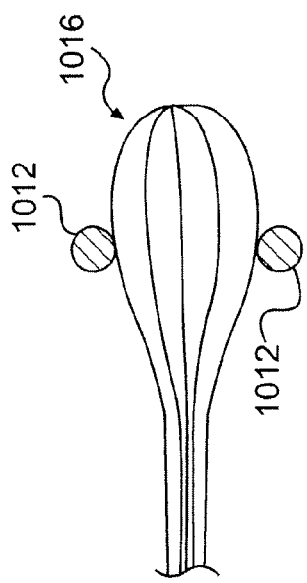
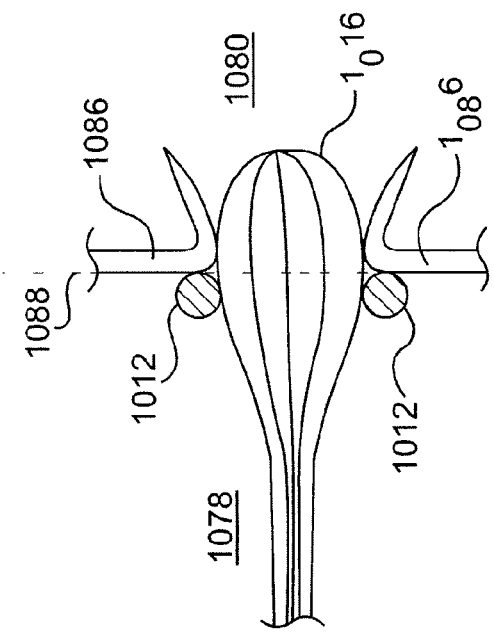
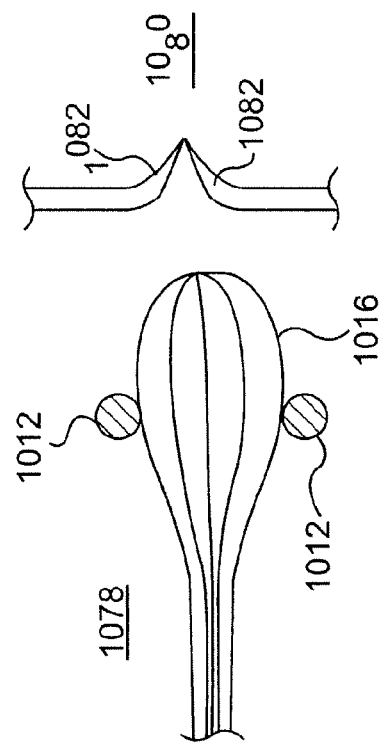
FIG. 44a
FIG. 44b
FIG. 44c

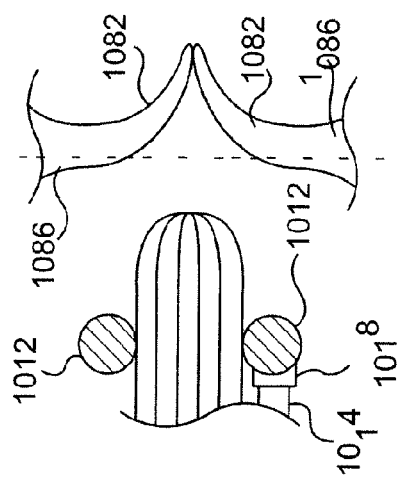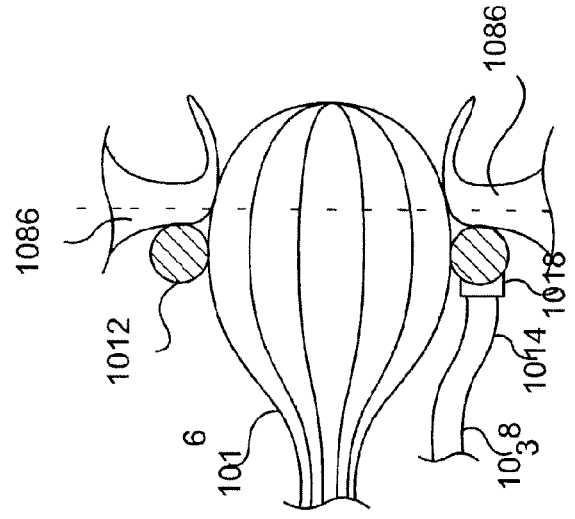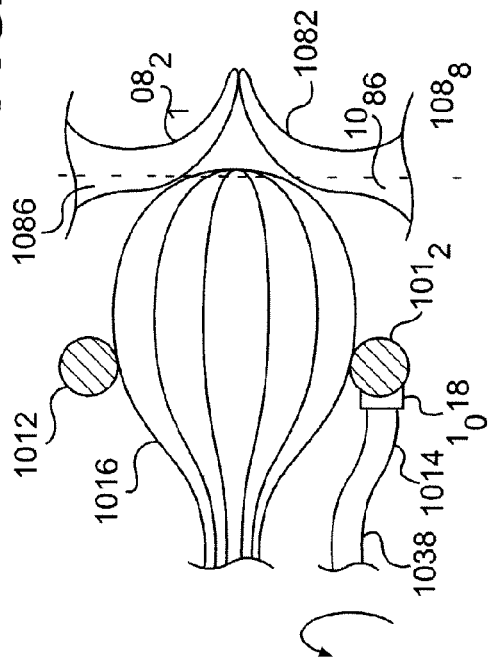

IMPLANTABLE DEVICES FOR CONTROLLING THE SIZE AND SHAPE OF AN ANATOMICAL STRUCTURE OR LUMEN

CROSS REFERENCE TO RELATED APPLICATIONS

This application also claims priority under 35 U.S.C. §119 (e) from U.S. Provisional Patent Application No. 60/878,068, filed on Jan. 3, 2007, which is also incorporated herein by reference.

STATEMENT REGARDING SPONSORED RESEARCH OR DEVELOPMENT

Not Applicable.

REFERENCE TO SEQUENCE LISTING

Not Applicable.

BACKGROUND OF THE INVENTION

1. Field of the Invention

This invention relates generally to implantable devices for controlling at least one of shape and size of an anatomic structure or lumen.

2. Description of Related Art

There is often a need to reduce the internal circumference of an orifice or other open anatomic structure to narrow or increase the size of the orifice or opening to achieve a desired physiologic effect. Often, such surgical procedures require interruption in the normal physiologic flow of blood, other physiologic fluids, or other structural contents through the orifice or structure. The exact amount of the narrowing or widening required for the desired effect often cannot be fully appreciated until physiologic flow through the orifice or structure is resumed. It would be advantageous, therefore, to have an adjustable means of achieving the narrowing or widening effect, such that the degree of narrowing or widening could be changed after its implantation, and after the resumption of normal flow in situ.

One example of a dysfunction within an anatomic lumen is in the area of cardiac surgery, and specifically valvular repair. Approximately one million open heart surgical procedures are now performed annually in the United States, and twenty percent of these operations are related to cardiac valves.

The field of cardiac surgery was previously transformed by the introduction of the pump oxygenator, which allowed open heart surgery to be performed. Valvular heart surgery was made possible by the further introduction of the mechanical ball-valve prosthesis, and many modifications and different forms of prosthetic heart valves have since been developed. However, the ideal prosthetic valve has yet to be designed, which attests to the elegant form and function of the native heart valve.

As a result of the difficulties in engineering a perfect prosthetic heart valve, there has been growing interest in repairing a patient's native valve. These efforts have documented equal long-term durability to the use of mechanical prostheses, with added benefits of better ventricular performance due to preservation of the subvalvular mechanisms and obviation of the need for chronic anticoagulation. Mitral valve repair has become one of the most rapidly growing areas in adult cardiac surgery today.

Mitral valve disease can be subdivided into intrinsic valve disturbances and pathology extrinsic to the mitral valve ultimately affecting valvular function. Although these subdivisions exist, many of the repair techniques and overall operative approaches are similar in the various pathologies that exist.

Historically, most valvular pathology was secondary to rheumatic heart disease, a result of a streptococcal infection, most commonly affecting the mitral valve, followed by the aortic valve, and least often the pulmonic valve. The results of the infectious process are mitral stenosis and aortic stenosis, followed by mitral insufficiency and aortic insufficiency. With the advent of better antibiotic therapies, the incidence of rheumatic heart disease is on the decline, and accounts for a smaller percentage of valvular heart conditions in the developed world of the present day. Commissurotomy of rheumatic mitral stenosis was an early example of commonly practiced mitral valve repair outside of the realm of congenital heart defects. However, the repairs of rheumatic insufficient valves have not met with good results due to the underlying valve pathology and the progression of disease.

Most mitral valve disease other than rheumatic results in valvular insufficiency that is generally amenable to repair. Chordae rupture is a common cause of mitral insufficiency, resulting in a focal area of regurgitation. Classically, one of the first successful and accepted surgical repairs was for ruptured chordae of the posterior mitral leaflet. The technical feasibility of this repair, its reproducible good results, and its long-term durability led the pioneer surgeons in the field of mitral valve repair to attempt repairs of other valve pathologies.

Mitral valve prolapse is a fairly common condition that leads over time to valvular insufficiency. In this disease, the plane of coaptation of the anterior and posterior leaflets is "atrialized" relative to a normal valve. This problem may readily be repaired by restoring the plane of coaptation into the ventricle.

The papillary muscles within the left ventricle support the mitral valve and aid in its function. Papillary muscle dysfunction, whether due to infarction or ischemia from coronary artery disease, often leads to mitral insufficiency (commonly referred to as ischemic mitral insufficiency). Within the scope of mitral valve disease, this is the most rapidly growing area for valve repair. Historically, only patients with severe mitral insufficiency were repaired or replaced, but there is increasing support in the surgical literature to support valve repair in patients with moderate insufficiency that is attributable to ischemic mitral insufficiency. Early aggressive valve repair in this patient population has been shown to increase survival and improve long-term ventricular function.

In addition, in patients with dilated cardiomyopathy the etiology of mitral insufficiency is the lack of coaptation of the valve leaflets from a dilated ventricle. The resultant regurgitation is due to the lack of coaptation of the leaflets. There is a growing trend to repair these valves, thereby repairing the insufficiency and restoring ventricular geometry, thus improving overall ventricular function.

Two essential features of mitral valve repair are to fix primary valvular pathology (if present) and to support the annulus or reduce the annular dimension using a prosthesis that is commonly in the form of a ring or band. The problem encountered in mitral valve repair is the surgeon's inability to fully assess the effectiveness of the repair until the heart has been fully closed, and the patient is weaned off cardiopulmonary bypass. Once this has been achieved, valvular function can be assessed in the operating room using transesophageal echocardiography (TEE). If significant residual valvular insufficiency is then documented, the surgeon must re-arrest the heart, re-open the heart, and then re-repair or replace the valve. This increases overall operative, anesthesia, and bypass times, and therefore increases the overall operative risks.

If the prosthesis used to reduce the annulus is larger than the ideal size, mitral insufficiency may persist. If the prosthesis is too small, mitral stenosis may result.

The need exists, therefore, for an adjustable prosthesis that would allow a surgeon to adjust the annular dimension in situ in a beating heart under TEE guidance or other diagnostic modalities to achieve optimal valvular sufficiency and function.

Cardiac surgery is but one example of a setting in which adjustment of the annular dimension of an anatomic orifice in situ would be desirable. Another example is in the field of gastrointestinal surgery, where the Nissen fundoplication procedure has long been used to narrow the gastro-esophageal junction for relief of gastric reflux into the esophagus. In this setting, a surgeon is conventionally faced with the tension between creating sufficient narrowing to achieve reflux control, but avoiding excessive narrowing that may interfere with the passage of nutrient contents from the esophagus into the stomach. Again, it would be desirable to have a method and apparatus by which the extent to which the gastro-esophageal junction is narrowed could be adjusted in situ to achieve optimal balance between these two competing interests.

Aside from the problem of adjusting the internal circumference of body passages in situ, there is often a need in medicine and surgery to place a prosthetic implant at a desired recipient anatomic site. For example, existing methods proposed for percutaneous mitral repair include approaches through either the coronary sinus or percutaneous attempts to affix the anterior mitral leaflet to the posterior mitral leaflet. Significant clinical and logistical problems attend both of these existing technologies. In the case of the coronary sinus procedures, percutaneous access to the coronary sinus is technically difficult and time consuming to achieve, with procedures which may require several hours to properly access the coronary sinus. Moreover, these procedures employ incomplete annular rings, which compromise their physiologic effect. Such procedures are typically not effective for improving mitral regurgitation by more than one clinical grade. Finally, coronary sinus procedures carry the potentially disastrous risks of either fatal tears or catastrophic thrombosis of the coronary sinus.

Similarly, percutaneous procedures which employ sutures, clips, or other devices to affix the anterior mitral leaflets to the posterior mitral leaflets also have limited reparative capabilities. Such procedures are also typically ineffective in providing a complete repair of mitral regurgitation. Furthermore, surgical experience indicates that such methods are not durable, with likely separation of the affixed valve leaflets. These procedures also fail to address the pathophysiololgy of the dilated mitral annulus in ischemic heart disease. As a result of the residual anatomic pathology, no ventricular remodeling or improved ventricular function is likely with these procedures.

The need exists, therefore, for a delivery system and methods for its use that would avoid the need for open surgery in such exemplary circumstances, and allow delivery, placement, and adjustment of a prosthetic implant to reduce the diameter of such a mitral annulus in a percutaneous or other minimally invasive procedure, while still achieving clinical and physiologic results that are at least the equivalent of the yields of the best open surgical procedures for these same problems.

The preceding cardiac applications are only examples of some applications according to the present invention. Another exemplary application anticipated by the present invention is in the field of gastrointestinal surgery, where the aforementioned Nissen fundoplication procedure has long been used to narrow the gastro-esophageal junction for relief of gastric reflux into the esophagus. In this setting, a surgeon is conventionally faced with the tension between creating sufficient narrowing to achieve reflux control, but avoiding excessive narrowing that may interfere with the passage of nutrient contents from the esophagus into the stomach. Additionally, "gas bloat" may cause the inability to belch, a common complication of over-narrowing of the GE junction. An adjustable prosthetic implant according to the present invention could allow in situ adjustment in such a setting under physiologic assessment after primary surgical closure.

Such an adjustable prosthetic implant according to the present invention could be placed endoscopically, percutaneously, or with an endoscope placed within a body cavity or organ, or by trans-abdominal or trans-thoracic approaches. In addition, such an adjustable prosthetic implant according to the present invention could be coupled with an adjustment means capable of being placed in the subcutaneous or other anatomic tissues within the body, such that remote adjustments could be made to the implant during physiologic function of the implant. This adjustment means can also be contained within the implant and adjusted remotely, i.e. remote control adjustment. Such an adjustment means might be capable of removal from the body, or might be retained within the body indefinitely for later adjustment.

The present invention and the methods for its use anticipate many alternate embodiments in other potential applications in the broad fields of medicine and surgery. Among the other potential applications anticipated according to the present invention are adjustable implants for use in the treatment of morbid obesity, urinary incontinence, anastomotic strictures, arterial stenosis, urinary incontinence, cervical incompetence, ductal strictures, and anal incontinence. The preceding discussions are intended to be exemplary embodiments according to the present invention and should not be construed to limit the present invention and the methods for its use in any way.

SUMMARY OF THE INVENTION

Implantable devices, methods and systems for controlling at least one of shape and size of an anatomical structure or lumen, including minimally invasive implantable devices and methods are disclosed herein. In embodiments, an implantable device is provided that has a adjustable member configured to adjust the dimensions of the implantable device. A rotatable or torqueable adjustment tool is configured to provide adjustment of the dimensions of the implantable device. Such adjustments may be under the control of an operator, and may be effected my manual force alone or may be effected with the aid of gears, motors, or other mechanical, electrical, hydraulic or other aids. An adjustment tool is configured to engage with an implantable device in a non-planar orientation, so that at least a portion of the adjustment tool is non-planar with respect to the plane defined by the implantable device and/or tissue in contact with or adjacent to, the implantable device. For example, where the implantable device is in contact with, or adjacent to, a valve annulus, at least a portion of the adjustment tool is non-planar with respect to the valve annulus. Embodiments of the devices, systems and methods disclosed herein provide implantable devices and methods for controlling a perimeter of an anatomic orifice or lumen, including minimally invasive implantable devices and methods for controlling a perimeter of an anatomic orifice or lumen.

In embodiments of the present invention, an implantable device is provided for controlling at least one or more of a shape, a size, a configuration, or other attribute of an anatomical structure or lumen. An implantable device has an adjustable member configured to adjust the dimensions of the implantable device. An adjustment tool is configured to provide adjustment of the dimensions of the implantable device, the adjustment tool providing translated motion through rotation.

In embodiments of the present invention, having an implantable device for controlling at least one of shape and size of an anatomical structure or lumen, an adjustable member is provided that is configured to adjust a dimension of the implantable device. In embodiments, an adjustable member having features of the invention may include first and second bands, An adjustable member having features of the invention may be configured to adjust a dimension of an implantable device, the implantable device having an anterior portion, a posterior portion and dual threads that provide preferential adjustment of one side or the other of the implantable device:

Disclosed herein are methods, systems and devices for positioning an adjustable implant adjacent target tissue, and for attaching an adjustable implant device to target tissue. In embodiments of devices having features of the invention, a device for positioning an adjustable implant device adjacent to target tissue, includes an implant tool holding element configured to releasably hold the adjustable implant device; a tool holding element configured to hold an adjustment tool and to allow operation thereof while so held, the adjustment tool being configured to adjust the adjustable implant device; and an implant securing element having a configuration effective to secure the implant to the target tissue.

In embodiments of the devices having features of the invention, an implant securing element may have a first configuration adapted for penetrating tissue and a tip portion adapted for penetrating tissue, and a second configuration adapted for engaging tissue. In embodiments, an implant securing element in the second configuration may be adapted to engage tissue and to engage and adjustable implant device, effective to secure the adjustable implant device to tissue.

Methods, systems and devices having features of the invention may further include an implant positioning element that is configured to guide an adjustable implant device effective to properly orient the adjustable implant device adjacent target tissue for securing the implant device to target tissue. Such positioning may be effective to guide or orient, or both, the implant to a desired position or orientation, or both, within an anatomic orifice or lumen.

In embodiments, an implant securing element is configured to co-operate with an implant positioning element effective to secure the adjustable implant device to target tissue while the adjustable implant device is properly positioned adjacent the anatomic orifice or lumen. An implant positioning element may include an expansible portion adapted to assume a collapsed first configuration and to assume an expanded second configuration. An implant positioning element may be configured to allow fluid to pass therethough. In embodiments, am implant positioning element is configured to allow fluid to pass therethrough when disposed in a second configuration, or when disposed in a first configuration, or both. In embodiments, an implant positioning element may include a fenestrated surface; may include a mesh; and may include a plurality of elongated elements forming a whisk, the elongated elements may include flexible elements, which may include metal wires, an organic polymer material, or other flexible material.

In embodiments of the methods, systems, and devices having features of the invention, an adjustable implant may have an expansible internal perimeter, and an implant positioning element may be configured to expand as the internal perimeter of the adjustable implant is increased. In embodiments of the methods, systems and devices having features of the invention, and adjustable implant may have an expansible internal perimeter, and an implant positioning element may be configured toe expand so as to effect the increase of the internal perimeter of the adjustable implant device. In embodiments, an implant positioning element may be configures to contract, and may be configured toe reduce an internal perimeter of an adjustable implant device.

In embodiments of the methods, systems, and devices having features of the invention, an implant securing element may have a first configuration and a second configuration. A first configuration may be substantially straight configuration, and a second configuration may be a non-linear configuration. In embodiments, a second configuration may have one or more configurations elements, and may include a configuration element that is a curve, a loop, a coil, a spiral coil, a barb, a bifurcation, an anchor shape, or a combination thereof. In embodiments, an implant securing device may include at least two configurations elements selected from a curve, a loop, a coil, a spiral coil, a barb, a bifurcation, an anchor shape. Such configuration elements may be at least two of the same configuration element, or may be at least two different configuration elements.

In embodiments of the methods, systems, and devices having features of the invention, an implant securing element is configured toe engage an implant device and to engage tissue. Such an engagement may be effective to secure an adjustable implant device to tissue, such as tissue adjacent to an anatomical orifice or lumen. In embodiments, an implant securing element may be configured to engage tissue and to coil around at least a portion of an implant device; may be configured to engage tissue and to pass through at least a portion of an implant device; or may be otherwise configured to engage tissue and to engage an adjustable implant device, effective to secure an adjustable implant device to tissue. In embodiments, engagement of tissue may include penetration of tissue, anchoring within tissue, attaching to tissue, or other means of engaging tissue.

In embodiments of the methods, systems, and devices having features of the invention, an implant holding element may include a housing configured to house an implant securing element. A housing may be configured to allow egress of at least a portion of an implant securing element from the housing. An implant securing element may be configured to be housed or substantially contained within a housing in a first configuration. A housing may include a substantially linear portion, and an implant securing element first configuration may be linear, or substantially straight configuration. In embodiments, a housing may include a non-linear portion, and an implant securing element first configuration may include a non-linear configuration.

Embodiments of the methods, systems, and devices having features of the invention may include or be configured to cooperate or work with an adjustment tool that is configured to operably engage with an adjustable implant device having features of the invention, effective to adjust a dimension of the adjustable implant device.

Also discussed herein are methods of securing an adjustable implant device to target tissue. Target tissue may be, for example, tissue adjacent an anatomical orifice or lumen. A method of securing an adjustable implant device to target tissue having an anatomic orifice or lumen may have steps including: providing an adjustable implant having an expansible internal perimeter and configured for controlling the internal perimeter of an anatomic orifice or lumen; providing an adjustable implant holding element that is configured to releasably hold the adjustable implant; providing an implant securing element that is configured to assume at least a first configuration (adapted for penetrating tissue) and a second configuration (adapted for engaging tissue), where the implant securing element has a tip portion that is configured to penetrate tissue; placing the adjustable implant device at a desired location adjacent the target tissue near the adjustable implant device; advancing the implant securing element in a first configuration effective that the implant securing element tip portion penetrates tissue; engaging tissue with the implant securing element in a second configuration; and engaging the adjustable implant device with the implant securing element while the implant securing element secures the adjustable implant device to target tissue. An implant securing element may have a configuration that includes on or more of a curve, a loop, a coil, a spiral coil, a barb, a bifurcation, an anchor shape. An implant securing element may have more than one of the same configuration element.

Devices, systems and methods having features of the invention may include, provide, or use a housing for housing an implant securing element. In embodiments of methods having features of the invention, an advancing step may include a step of advancing at least a portion of an implant securing element outside the housing.

Methods having features of the invention may further include that a placing step includes placing the implant in contact with target tissue; that an advancing step includes moving the implant securing element tip portion, effective that the tip portion enters tissue at a location on a tissue surface; and that an engaging tissue step includes moving the tip portion effective that the tip portion exits tissue from a location on the tissue surface different than the entry location.

Methods of securing an adjustable implant device to target tissue having features of the invention may further include an engaging step where the engaging includes passing at least a portion of an implant securing element around at least a portion of the adjustable implant device, or may further include passing at least a portion of the implant securing element through at least a portion of the adjustable implant device. An adjustable implant device may include a material that is configured to hold the implant securing element and through which the implant securing element tip portion may pass. A material suitable for such methods may include a woven material. An adjustable implant device may have a passage that is configured to accept a portion of an implant securing element. In embodiments, a passage configured to accept a portion of an implant securing element may include a loop, and may include a hole providing a pathway completely through a portion of said adjustable implant device.

Embodiments of methods having features of the invention may further adjusting the internal perimeter of an adjustable implant device. An adjusting step may include adjusting a tool that is releasably coupled to an adjustable implant device; may further include, where an implant device is held by an implant holding element, releasing the adjustable implant device from the implant holding element.

Also provided are systems having features of the inventions. In embodiments, a system for controlling the internal perimeter of an anatomic orifice or lumen disposed adjacent target tissue may include: an adjustable implant device having an adjustable perimeter, a perimeter adjustment mechanism, and a docking element that is configured to operably engage an adjustment tool, where the perimeter adjustment mechanism is operably connected with the docking element; an adjustment tool that is configured to operably engage the docking element; and an implant placement device that includes an implant engagement element and an implant securing element that is configured to secure the implant to target tissue.

A system having features of the invention may also have an implant securing element that has a tip portion configured to penetrate tissue. An implant securing element tip portion configured to penetrate tissue may be configured to assume more than one configuration. Such configurations may include at least a first configuration and a second configuration, the first configuration being adapted for penetrating tissue, and the second configuration being adapted for engaging tissue. A second configuration adapted for engaging tissue may include a configuration element that is selected from a curve, a loop, a coil, a spiral coil, a barb, a bifurcation, and an anchor shape. An implant securing element tip portion configured to penetrate tissue may have at least two configuration elements, which may be at least two of the same configuration element, or may be at least two different configuration elements. In embodiments, an implant securing element tip portion configured to penetrate tissue may be configured to engage tissue and to engage an adjustable implant device, effective to secure an adjustable implant device to tissue.

A system having features of the invention may further include an implant positioning device that is configured to properly orient an adjustable implant device for securing the adjustable implant device to target tissue. An implant positioning device may be configured to guide an adjustable implant device effective to properly orient said adjustable implant device adjacent target tissue for securing to said target tissue. In embodiments, an implant positioning device may include a plurality of flexible elements. In embodiments, an implant positioning device may have a fenestrated surface, or a mesh, configured to allow fluid to pass therethrough.

In embodiments, a system having features of the invention may include an expansible element that is adapted to assume a collapsed first configuration and to assume an expanded second configuration. An expansible element may be configured to allow fluid to pass therethrough when disposed in a second configuration, or a first configuration, or both. In embodiments, the flexible elements may be or include elongated elements, such as metal wires. Flexible elements may be made of, or include, an organic polymer material.

In embodiments of systems having features of the invention, an implant positioning device may have a plurality of elongated elements forming a whisk. An implant positioning device may be configured to expand as the adjustable perimeter of the adjustable implant is increased, and may be configured to expand so as to effect the increase of the adjustable perimeter of the adjustable implant. In embodiments, an implant positioning device may be configured to contract, and may be configured to reduce an internal perimeter of an adjustable implant device.

Devices, systems and methods having features of the invention allow an operator, such as a surgeon, to adjust a dimension of an anatomical orifice or lumen in a patient, thereby providing for better operation and function of that anatomical orifice or lumen and improving the health and quality of life of that patient. The devices, systems and methods disclosed herein provide advantages over the prior art in that such adjustments may be made with less trauma to the patient, and such adjustments may be made, and re-made, to provide adjustments that are adapted to the individual patient and to changes in the physiology or function of the anatomical orifice or lumen over time or as a result of treatment. Where, for example, the anatomical orifice or lumen is a heart valve, the devices, systems and methods disclosed herein provide for repair of a heart valve while the heart remains beating, and for adjustment of the repair to accommodate changes to valve function under different conditions, as may be found following surgery, to provide adjustments tailored to the patient during recovery and to insure that the valvular adjustments are suited to the patients condition not just during surgery, but also after surgery.

BRIEF DESCRIPTION OF FIGURES

FIG. 1 is a front view of a first embodiment of an implant for reducing the circumference of an anatomic orifice.

FIG. 2 is a front view of the implant of FIG. 1 secured to the annulus of a mitral valve, with the implant in an expanded position.

FIG. 3 is a front view of the implant of FIG. 1 secured to the annulus of a mitral valve, with the implant in a contracted position to reduced the size of the heart valve opening.

FIG. 17 shows the implant in the folded position, and FIG. 18 shows the implant in the unfolded position.

FIG. 25 is a front view of a fifth embodiment of an implant for reducing the circumference of an anatomic orifice, with the implant shown in its expanded configuration.

FIG. 26 is a front view of the implant of FIG. 25, with the implant shown in its contracted configuration.

FIG. 27 is an enlarged view of the area indicated by the circle 27 in FIG. 25, with the outer body removed to show interior detail.

FIG. 33 is a schematic view of an embodiment of an implantable device of the present invention with an outer tubing and an inner tubing in a relative first position.

FIG. 34 is a schematic view of an embodiment of an implantable device of the present invention with an outer tubing and an inner tubing in a relative second position.

FIG. 35 is a schematic view of an embodiment of an implantable device of the present invention with an outer tubing and an inner tubing in a relative third position.

FIG. 38A shows portions of the illustrated system with the implant device in a reduced-diameter configuration disposed proximal to the distal end of the positioning element;

FIG. 38B shows the portions of the illustrated system with the implant device in a reduced-diameter configuration disposed distal to the position shown in FIG. 38A; and FIG. 38C indicates operation of the adjustment tool, showing the illustrated system with the implant device and positioning device in expanded-diameter configurations.

FIG. 39A shows a partial cut-away side view of a distal portion of a securing element housing and of a securing element and a securing-element deployment element within the housing;

FIG. 39B shows the partial cut-away side view of FIG. 39A with the securing element partially extending from the aperture at the distal end of the housing;

FIG. 39C shows the partial cut-away side view of FIG. 39A with the securing element extending further from the aperture at the distal end of the housing than shown in FIG. 39B and the curvature of the distal tip portion of the securing element that extends beyond the aperture of the housing having an increased curvature as compared to the configuration in FIG. 39B; and FIG. 39D shows a partial cut-away side view of a distal portion of a securing element housing, a securing-element deployment element extended distally to the distal end of the housing, and of a securing element released from within the housing vial the aperture at the distal end of the housing, the curvature of the securing element forming a substantially closed loop.

FIG. 40A is a schematic partial cross-sectional illustration of an adjustable implant holding element that is also a securing-element housing element, and of a securing element disposed within the housing, and a schematic cross-sectional illustration of an adjustable implant device showing only an outline, with the adjustable implant device in contact with a tissue surface defining a tissue plane;

FIG. 40B-G sequentially show advancement of a securing-element deployment element, and an advancement of a securing element outward of an aperture of the housing, the tip portion of the securing element penetrating the adjustable implant device and then penetrating the tissue, followed by the tip portion exiting from tissue on the same tissue surface (although at a different location on that surface) effective to secure the adjustable implant device to tissue; where FIG. 40B shows a tip portion of the adjustable implant securing element penetrating the adjustable implant device;

FIG. 40C shows a tip portion of the adjustable implant securing element having passed through the adjustable implant device and penetrating tissue adjacent the device;

FIG. 40D shows further advancement of the tip portion of the adjustable implant securing element and further penetration of the tissue;

FIG. 40E shows further advancement of the tip portion of the adjustable implant securing element and its emergence from the tissue and further curvature as it advances;

FIG. 40F shows further advancement of the curved element to form a curved shape with the tip of the deployment element disposed outside the adjustable implant device effective to secure the adjustable implant device to tissue; and FIG. 40G shows an embodiment in which the securing element forms a curved shape with the tip of the deployment element disposed within the adjustable implant device effective to secure the adjustable implant device to tissue.

FIG. 41A-D provide a series of schematic partial cross-sectional illustration showing deployment of a securing element from a housing to secure an adjustable implant device to tissue, where FIG. 41A is a schematic partial cross-sectional illustration of an adjustable implant holding element that is also a securing-element housing element, and of a securing element disposed within the housing, and a schematic cross-sectional illustration of a adjustable implant device disposed adjacent a tissue surface;

FIG. 41B-D are sequential illustrations following FIG. 41A, where FIG. 41B shows a distal tip portion of the securing element extending from the distal end of the housing and assuming a curved shape, the distal portion also shown penetrating the tissue as it extends and curves;

FIG. 41C shows further extension and further curvature of the securing element, as the securing element deployment element is advance distally within the housing;

FIG. 41D shows further extension and further curvature of the securing element, effective that the securing element substantially surrounds the adjustable implant device as well as extends into and out of the tissue, effective to dexure the adjustable implant device to the tissue.

FIG. 42A is a schematic partial cross-sectional illustration of an adjustable implant holding element that is also a securing-element housing element having a securing element disposed within the housing. A schematic cross-sectional illustration of an adjustable implant device disposed adjacent to a tissue surface is also shown. The adjustable implant holding element has a retention element that secures the adjustable implant holding element to the adjustable implant device. The retention element is illustrate in these figures as an anchor-shaped element.

FIG. 42B-I are sequential illustrations following FIG. 41A showing penetration of the implant device by the implant securing element, penetration of tissue by the implant device securing element, securing of the implant device to tissue by the implant device securing element, and release of the adjustable implant holding element from the adjustable implant device, where FIG. 41B shows a tip portion of the adjustable implant securing element penetrating the adjustable implant device;

FIG. 42C shows a tip portion of the adjustable implant securing element having passed through the adjustable implant device and penetrating adjacent tissue;

FIG. 42D shows further advancement of the tip portion of the adjustable implant securing element and further penetration of the tissue, the tip portion also assuming a curved configuration within the tissue;

FIG. 42E shows further advancement of the tip portion of the adjustable implant securing element, further curvature, and the emergence of a distal portion of the adjustable implant securing element from the tissue;

FIG. 42F shows further advancement of the securing element to form a curved shape with the tip of the deployment element disposed inside a portion of the adjustable implant device effective to secure the adjustable implant device to tissue;

FIG. 42G shows deployment of the adjustable implant securing element from its housing, and withdrawal of the aperture portion of the housing from contact with the adjustable implant device, the adjustable implant device being secured to the tissue by the adjustable implant securing element;

FIG. 42H shows further withdrawal of the aperture of the housing from contact with the adjustable implant device, and deformation of the anchor-shaped retention element;

FIG. 42I shows release of the housing and of the anchor-shaped retention element from the adjustable implant device, effective that the adjustable implant device is secured to tissue and freed from contact with the adjustable implant device holding element.

FIG. 44A is a partial schematic side-view of an implant device positioning element shown as a whisk of flexible wire-shaped material carrying an adjustable implant device having features of the invention ahs shown in schematic cross-sectional view.

FIG. 44B is a partial schematic side-view of the whisk and implant device of FIG. 44A, disposed adjacent a human mitral valve within a left atrium (shown in schematic cross-sectional view).

FIG. 44C is a partial schematic cross-sectional side-view of the whisk embodiment of the implant device positioning element and adjustable implant device disposed within a human mitral valve, showing the mitral valve leaflets displaced by the implant device positioning element which has expanded to substantially fill the aperture of the valve effectively to substantially center the device within the mitral valve. The implant device positioning element is shown here as it positions the adjustable implant device in proper position in contact with tissue adjacent the mitral valve in contact with the mitral valve annulus. Such positioning is effective to position the adjustable implant device in proper position for attachment to the mitral valve annulus for adjustment of a perimeter of the mitral valve.

FIG. 45C is a schematic partial cross-sectional side view showing distal portions of the whisk, implant device and adjustment tools of FIG. 45A, disposed within a left atrium near a mitral valve, the atrium and valve shown in partial schematic cross section, the mitral valve leaflets shown in a closed, apposed configuration. The whisk and adjustable implant device are shown in reduced-diameter configurations.

FIG. 45D is a schematic partial cross-sectional side view showing distal portions of the whisk, implant device and adjustment tools of FIG. 45A, disposed within a left atrium near a mitral valve, the atrium and valve shown in partial schematic cross sections, the mitral valve leaflets shown in a closed, apposed configuration. The whisk and adjustable implant device are shown in expanded-diameter configurations, due to operation of the adjustment tool, and the resulting radial expansion of the adjustable implant device and whisk.

FIG. 45E is a schematic partial cross-sectional side view showing distal portions of the whisk, implant device and adjustment tools of FIG. 45A, disposed within a human mitral valve, showing the mitral valve leaflets displaced by the implant device positioning element which is in an expanded configuration, as adjusted by the operation of the adjustment tool, effective to substantially fill the aperture of the valve effective to substantially center the adjustable implant device within the mitral valve and to size the adjustable implant device properly for placement of the adjustable implant device and for the use of the adjustable implant device to adjust a perimeter of the valve.

DETAILED DESCRIPTION OF THE INVENTION

Figure 4:
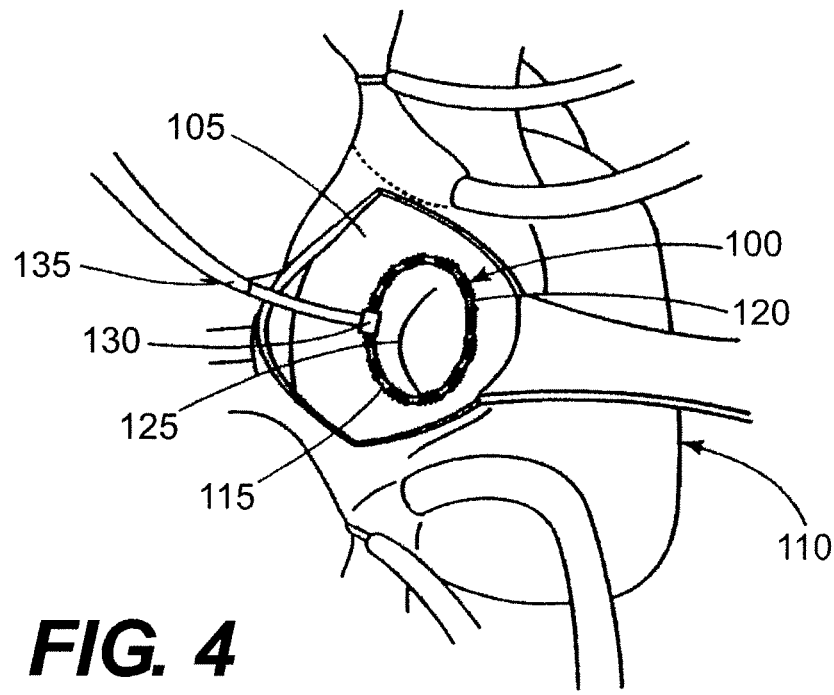
FIG. 4 is a perspective view of a second embodiment of an implant for reducing the circumference of an anatomic orifice, inserted through an open operative cardiac incision and secured around the mitral valve.

Referring now to the drawings, in which like numerals indicate like elements throughout the several views, an exemplary implant 10 comprising an implant body 15 is shown in FIG. 1. The implant body may be provided in a shape and size determined by the anatomic needs of an intended native recipient anatomic site within a mammalian patient. Such a native recipient anatomic site may be, by way of illustration and not by way of limitation, a heart valve, the esophagus near the gastro-esophageal junction, the anus, or other anatomic sites within a mammalian body that are creating dysfunction that might be relieved by an implant capable of changing the size and shape of that site and maintaining a desired size and shape after surgery.

The implant 10 of FIG. 1 comprises a circular implant body 15 which is provided with adjustable corrugated sections 20 alternating with intervening grommet-like attachment means 25 having narrowed intermediate neck portions. As can be seen in FIGS. 2 and 3, the implant body 15 may be secured to the annulus of a heart valve 30 by a fixation means such as a suture 35 secured over or through the attachment means 25. The corrugated sections 20 fold and unfold as the circumference of the implant body 15 shortens or lengthens. Adjustment of the implant 10 in situ may decrease the overall size of the heart valve 30, increasing the coaptation of the valve leaflets 40, and changing the configuration from that shown in FIG. 2 to that shown in FIG. 3.

Figure 5:
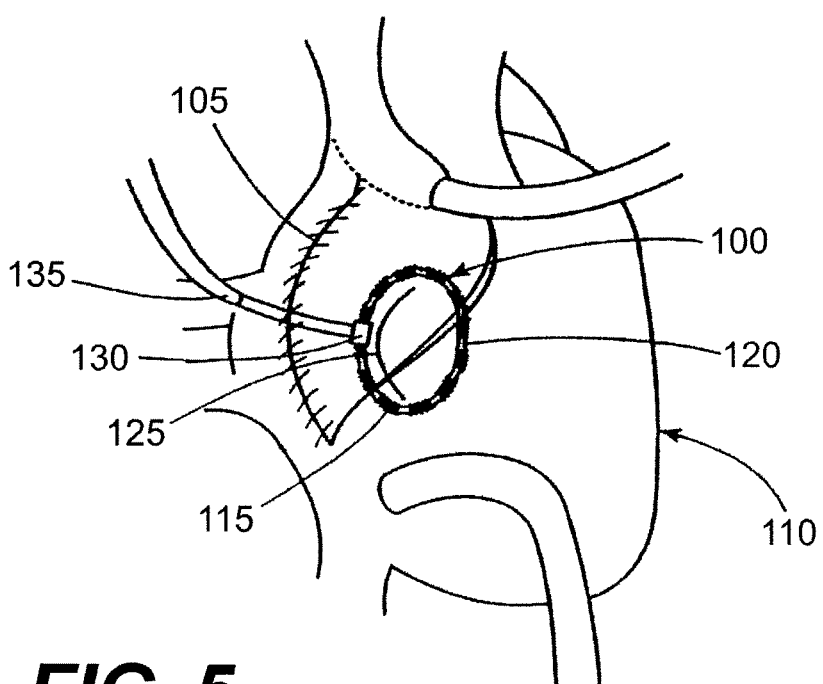
FIG. 5 is a perspective view of the implant of FIG. 4, showing the cardiac incision closed, an adjustment tool extending through the closed incision, and adjustment of the implant possible after the patient has been taken "off pump."

An additional exemplary embodiment 100 of the present invention is shown in FIGS. 4 and 5, with an open operative cardiac incision 105 in a heart 110 shown in FIG. 4, and closure of the cardiac incision 105 in FIG. 5. As shown in FIG. 4, the exemplary adjustable implant 100 according to the present invention comprises an implant body 115 with attachment means 120 that allows fixation to the annulus of a mitral valve 125. The exemplary adjustable implant 100 is further provided with an adjustment means 130 that is controlled by an attached or coupled adjustment tool 135. After closure of the myocardial incision 105 in FIG. 5, the adjustment tool 135 remains attached or coupled to the adjustment means 130, so that the size and shape of the implant 100 may further be affected after physiologic flow through the heart 110 is resumed, but with the chest incision still open. Once the desired shape and function are achieved, the adjustment tool 135 may be disengaged from the adjustment means 130 and withdrawn from the myocardial incision 105. In various embodiments according to the present invention, the adjustment means 130 may be configured and placed to allow retention by or re-introduction of the adjustment tool 135 for adjustment following closure of the chest incision.

To use the implant 100 of FIGS. 4 and 5, the physician makes the open operative incision 105 in the heart 110, as shown in FIG. 4, in the conventional manner. The implant 100, mounted at the forward end of adjustment tool 135, is then advanced through the incision 105 and sutured to the annulus of the mitral valve 125. The adjustment tool 135 is then manipulated, e.g., rotated, depending upon the design of the adjustment means 130, to cause the adjustment means to reduce the size of the implant body 115, and hence the underlying mitral valve 125 to which it is sutured, to an approximate size. The myocardial incision 105 can now be closed, as shown in FIG. 5, leaving the adjustment tool extending through the incision for post-operative adjustment.

Once the patient has been taken "off pump" and normal flow of blood through the heart 110 has resumed, but before the chest incision has been closed, further adjustments to the size of the mitral valve 125 can be made by manipulating the adjustment tool 135.

Figure 6:
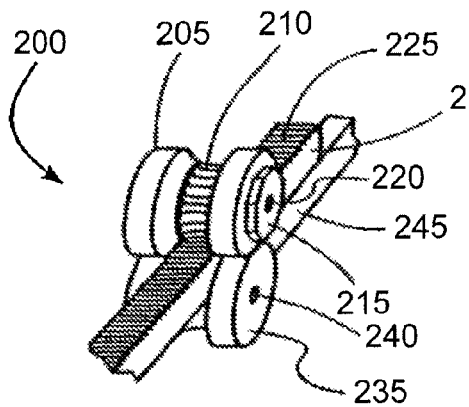
FIG. 6 is a perspective view of a first embodiment of an adjustment means for adjusting the circumference of an implant for reducing the circumference of an anatomic orifice.
Figure 7:
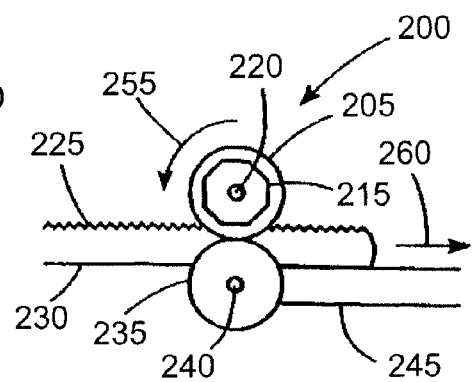
FIG. 7 is a right side view of the adjustment means of FIG. 6.
Figure 8:
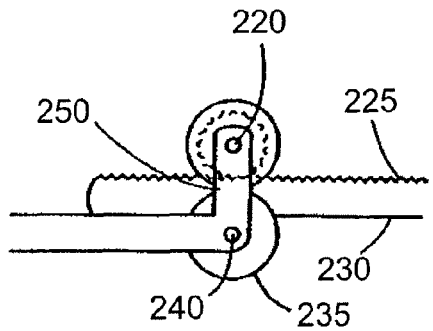
FIG. 8 is a left side view of the adjustment means of FIG. 6.

FIGS. 6-8 show an exemplary adjustment means 200 for adjusting the circumference of an annular implant such as the implant 100 previously described. The adjustment means 200 comprises a rack and pinion system in which a first cam 205 with geared teeth 210 and an engagement coupler 215 turns on a first axel 220. In this example, the first cam 205 engages a geared rack 225 on one or more surfaces of a first band 230. The first band 230 passes between the first cam 205 and a second cam 235 that turns on a second axel 240 that is joined to a second band 245. As shown in FIG. 8, the first and second axels 220, 240 are maintained in suitable spaced-apart relation by means of a bracket 250 formed at the end of the second band 245.

The adjustment means 200 is preferably set within a hollow annular implant 100 of the type previously described, though it is possible to use the adjustment means in a stand-alone configuration wherein the first and second bands 230, 245 are opposing ends of the same continuous annular structure. In either event, to adjust the length of an implant comprising the adjustment means 200, a tool such as a hex wrench engages the engagement coupler 215 on the first cam 205 and rotates the first cam in a counterclockwise direction as shown in FIG.

7, as indicated by the arrow 255. Rotation of the first cam 205 causes the teeth 210 to drive the rack 225 to move the first band 230 toward the right, as indicated by the arrow 260 in FIG. 7. This movement of the first band tightens the circumference of the annular implant. If the physician inadvertently adjusts the implant too tight, reversing direction of the engagement coupler 215 will loosen the implant.

In various embodiments according to the present invention, the first and second bands 230, 245 may be separate structures, or they may be opposing ends of the same continuous structure. In such an embodiment, when motion is imparted to the engagement coupler 215, the first cam 205 is rotated, causing the geared teeth 210 to engage the geared rack 225, and causing the first band 230 to move with respect to the second band 245 to adjust the circumference of an implant.

Figure 9:
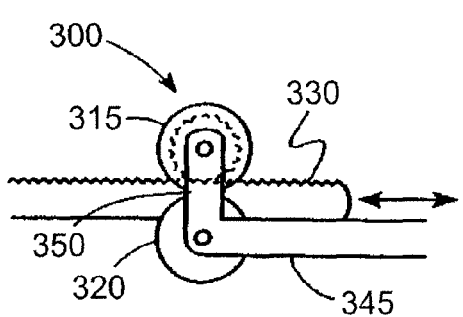
FIG. 9 is a right side view of a second embodiment of an adjustment means for adjusting the circumference of an implant for reducing the circumference of an anatomic orifice.

FIG. 9 shows a somewhat different configuration of an exemplary engagement means 300 according to the present invention, in which there is no engagement coupler, and a bracket 350 is provided on both sides of the cams to maintain the first cam 315 and the second cam 320 in close approximation. In one proposed embodiment, the bracket is designed with close tolerances so as to press the first band 330 closely against the second band 345, thereby to hold the bands in fixed relative position by friction. In another proposed embodiment, the brackets 350 are fabricated from an elastic material such that the cams 315, 320 can be spread apart to insert the first band 330 between the cams, whereupon the cams are pulled back together with sufficient force to hold the bands 330, 345 in fixed relative position by friction. In still another proposed embodiment involving an elastic mounting arrangement between the cams 315, 320, the lower edge of the first band 330 and the upper edge of the second band 345 have mating frictional or mechanical surfaces, whereby the cams 315, 320 can be spread apart to permit relative movement between the bands or released to clamp the bands together in fixed relation.

Figure 10:
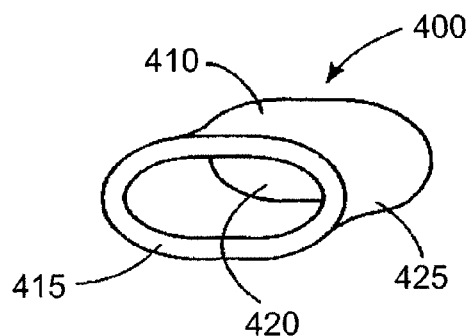
FIG. 10 is a perspective view of a first alternate embodiment of an attachment means for the implant of FIG. 1.

FIG. 10 shows an exemplary attachment means 400 for an implant according to the present invention. The attachment means 400 could be used, for example, in place of the attachment means 25 of the implant 10. The attachment means 400 takes the form of a grommet 410 comprising a wall 415 defining a lumen 420 and an attachment surface 425. Such an attachment means would be used with the implant body extending through the lumen 420 and with fixation devices such as sutures or wires either tied over or affixed through the attachment surface 425.

Figure 11:
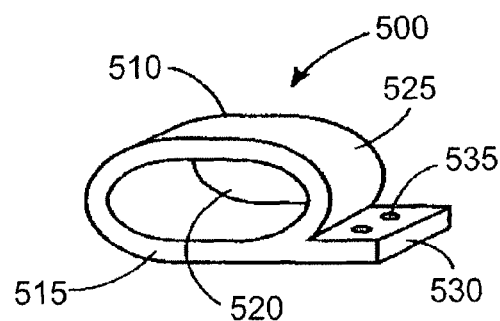
FIG. 11 is a perspective view of a second alternate embodiment of an attachment means for the implant of FIG. 1.
Figure 12:
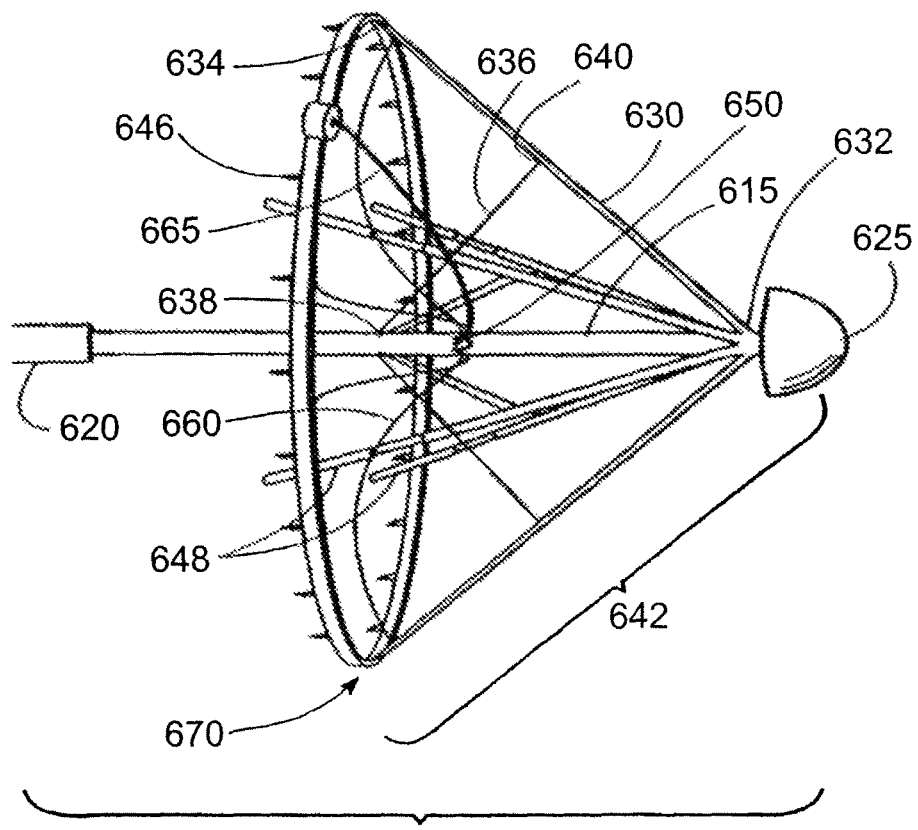
FIG. 12 is a perspective view of a third embodiment of an implant for reducing the circumference of an anatomic orifice.

FIG. 11 shows another alternate embodiment of an attachment means 500 for an implant according to the present invention. The attachment means 500 could also be used, for example, in place of the attachment means 25 of the implant 10. FIG. 11 shows an attachment means 500 in the form of a hollow tube or tube segment 510 comprising a wall 515 defining a lumen 520, an outer surface 525, and an attachment tab 530. Such an attachment means would be used with the implant body extending through the lumen 520 and with fixation devices such as sutures or wires either tied or otherwise affixed over or through the attachment tab 530. Such fixation devices might be placed through holes 535 provided in the attachment tab 530. Alternately a solid attachment tab 530 might be provided, and the fixation devices might be passed through the solid tab. Modifications of these attachment means may be used in conjunction with a sutureless attachment system.

Figure 13:
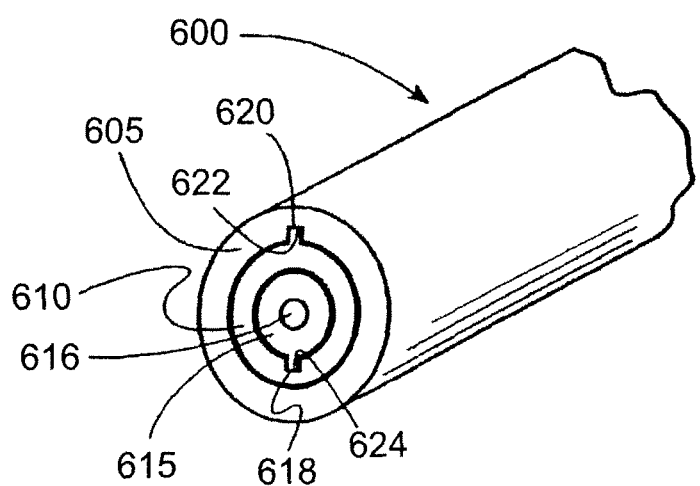
FIG. 13 is a perspective view of one end of the implant of FIG. 12 showing an optional keyed relationship between three coaxial cannulae to prevent relative rotation between the three components.

FIGS. 12-18 show another embodiment of a percutaneous annuloplasty device according to the present invention, in which an implant/delivery system array 600 includes a housing sheath 605 (not seen in FIG. 12), an actuating catheter 610 coaxially slidably mounted within the housing sheath 605, and a core catheter 615 coaxially slidably mounted within the actuating catheter 610. The core catheter has a central lumen 616 (FIG. 13). The actuating catheter 610 and core catheter 615 may be round tubular structures, or as shown in FIG. 13, either or both of the actuating and core catheters may be provided with one or more keyed ridges 618, 620 respectively to be received by one or more reciprocal slots 622, 624 within the inner lumen of either the housing sheath 605 or the actuating catheter 610, respectively. Such keyed ridges 618, 620 would limit internal rotation of an inner element within an outer element, should such restriction be desirable to maintain control of the inner contents from inadvertent displacement due to undersired rotational motion during use.

The implant/delivery system array 600 includes a distal tip 625 at the forward end of the core catheter 615. One or more radial implant support arms 630 have their distal ends 632 pivotably or bendably mounted to the core catheter 615 adjacent its distal tip 625. The proximal ends 634 of the radial implant support arms 630 normally extend along the core catheter 615 but are capable of being displaced outward away from the core catheter.

One or more radial support struts 636 have their proximal ends 638 pivotably or bendably mounted to the distal end of the actuating catheter 610. The distal end 640 of each radial support strut is 636 pivotably or bendably attached to a midpoint of a corresponding radial implant support arm 630. As the actuating catheter 610 is advanced with respect to the core catheter 615, the radial support struts 636 force the radial implant support arms 630 upward and outward in the fashion of an umbrella frame. Thus the actuating catheter 610, core catheter 615, radial support struts 636, and radial support arms 630 in combination form a deployment umbrella 642.

Figure 14:
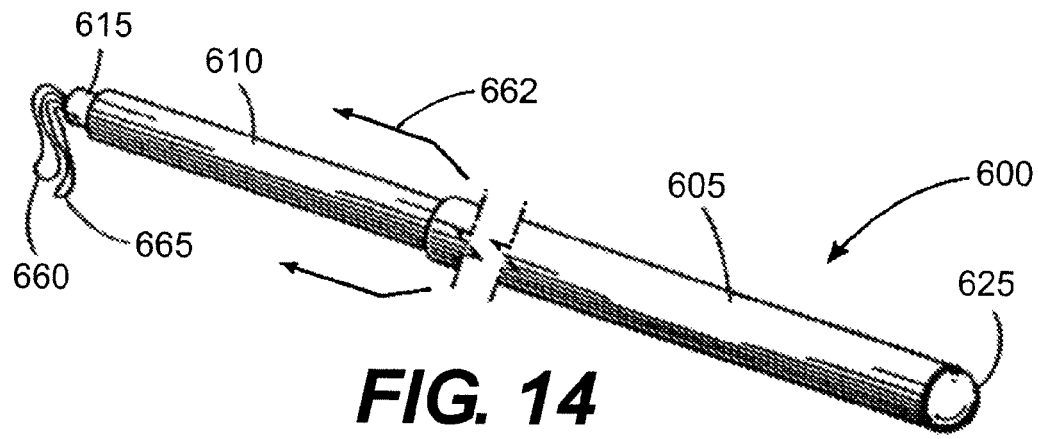
FIG. 14 is a perspective view of the implant of FIG. 12 showing the outer cannula extended to cover the implant.
Figure 15:
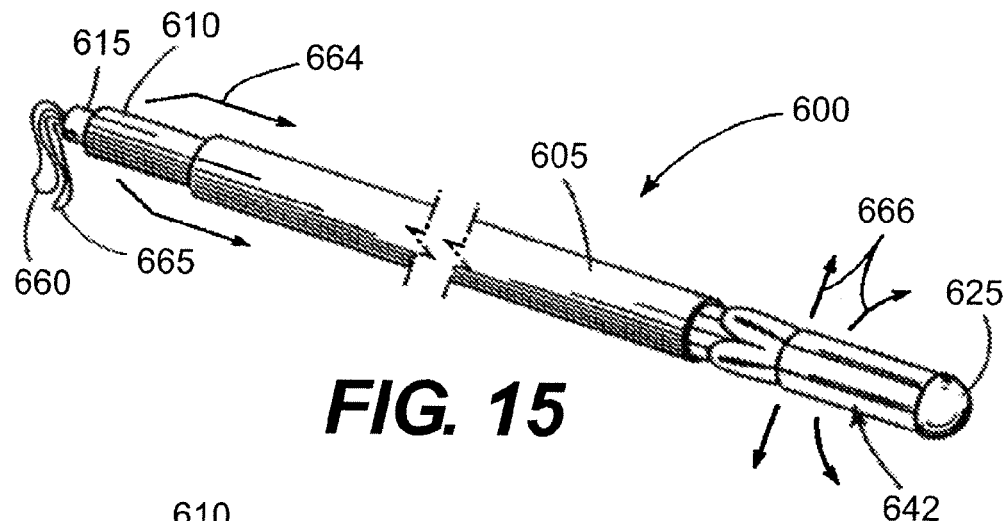
FIG. 15 is a perspective view of the implant of FIG. 12 showing the outer cannula retracted to expose the implant.
Figure 16:
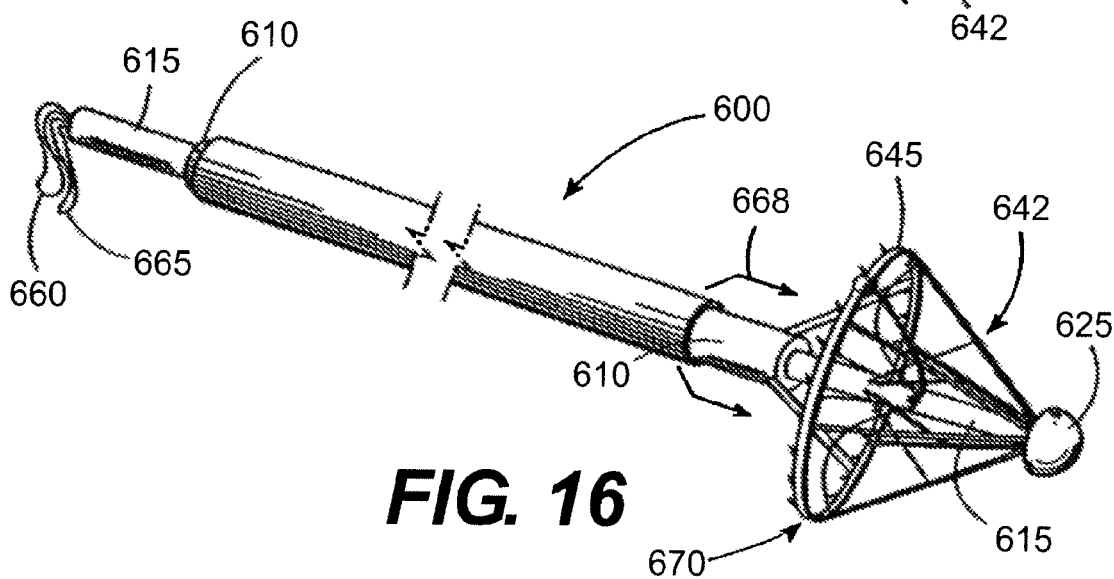
FIG. 16 is a perspective view of the implant of FIG. 12 showing the middle cannula extended to unfold the implant.

A prosthetic implant 645 is releasably attached to the proximal ends 634 of the radial implant support arms 630. Around the periphery of the prosthetic implant 645 and extending-proximally therefrom are a plurality of retention barbs 646. In addition, one or more of the radial implant support arms 630 comprise touchdown sensors 648 whose proximal ends extend proximal to the implant 645. Extending through the central lumen 616 (FIG. 13) of the core catheter 615 in the exemplary embodiment 600 and out lateral ports 650 (FIG. 12) spaced proximally from the distal tip 625 are one or more release elements 660, which serve to release the implant 645 from the delivery system, and one or more adjustment elements 665 which serve to adjust the implant's deployed size and effect. Because the release elements 660 and adjustment elements 665 extend through the proximal end of the core catheter 615, as seen in FIGS. 14-16, these elements can be directly or indirectly instrumented or manipulated by the physician. A delivery interface 670 (FIGS. 12,16) is defined in this example by the interaction of the deployment umbrella 642, the release elements 660, and the implant 645. In the disclosed embodiment, the release elements 660 may be a suture, fiber, or wire in a continuous loop that passes through laser-drilled bores in the implant 645 and in the radial implant support arms 630, and then passes through the length of the core catheter 615. In such an embodiment, the implant 645 may be released from the delivery system at a desired time by severing the release element 660 at its proximal end, outside the patient, and then withdrawing the free end of the release element 660 through the core catheter 610.

FIGS. 14-16 show the operation of the implant/delivery system array 600, in which an umbrella-like expansion of the prosthetic implant 645 is achieved by sliding movement of the housing sheath 605, the actuating catheter 610, and the core catheter 615. Referring first to FIG. 14, the housing sheath 605 is extended to cover the forward ends of the actuating catheter 610 and core catheter 615 for intravascular insertion of the implant/delivery system array 600. From this starting position, the housing sheath 605 is retracted in the direction indicated by the arrows 662. In FIG. 15 the housing sheath 605 has been retracted to expose the forward end of the actuating catheter 610 and the collapsed deployment umbrella 642. From this position the actuating catheter 610 is advanced in the direction indicated by the arrows 664. This will cause the deployment umbrellas to expand in the directions indicated by the arrows 666. FIG. 16 shows the expansion of the deployment umbrella 642 produced by distal motion of the actuating catheter 610 relative to the core catheter 615. After the implant 645 has been positioned and adjusted to the proper size, the housing sheath 605 is advanced in the direction indicated by the arrows 668 to collapse and to cover the deployment umbrella 642 for withdrawal of the device from the patient.

Figure 17:
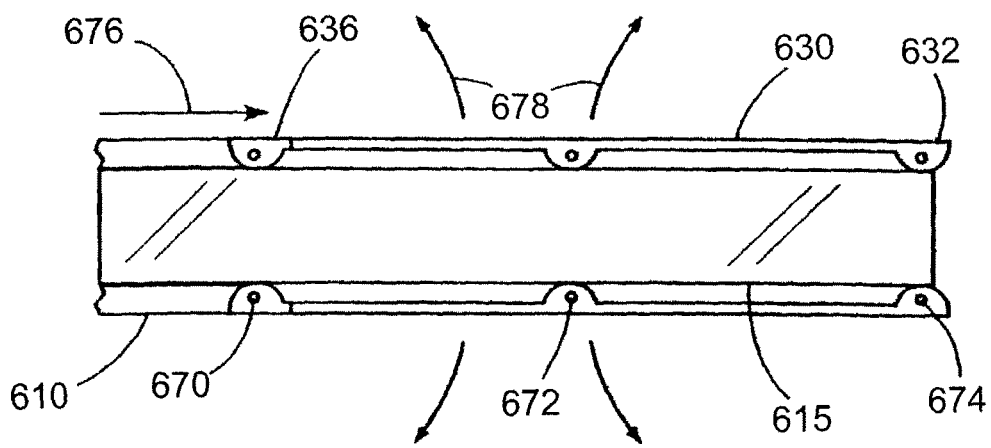
FIGS. 17 and 18 are schematic views illustrating how extension of the middle cannula causes the implant to unfold, where
Figure 18:
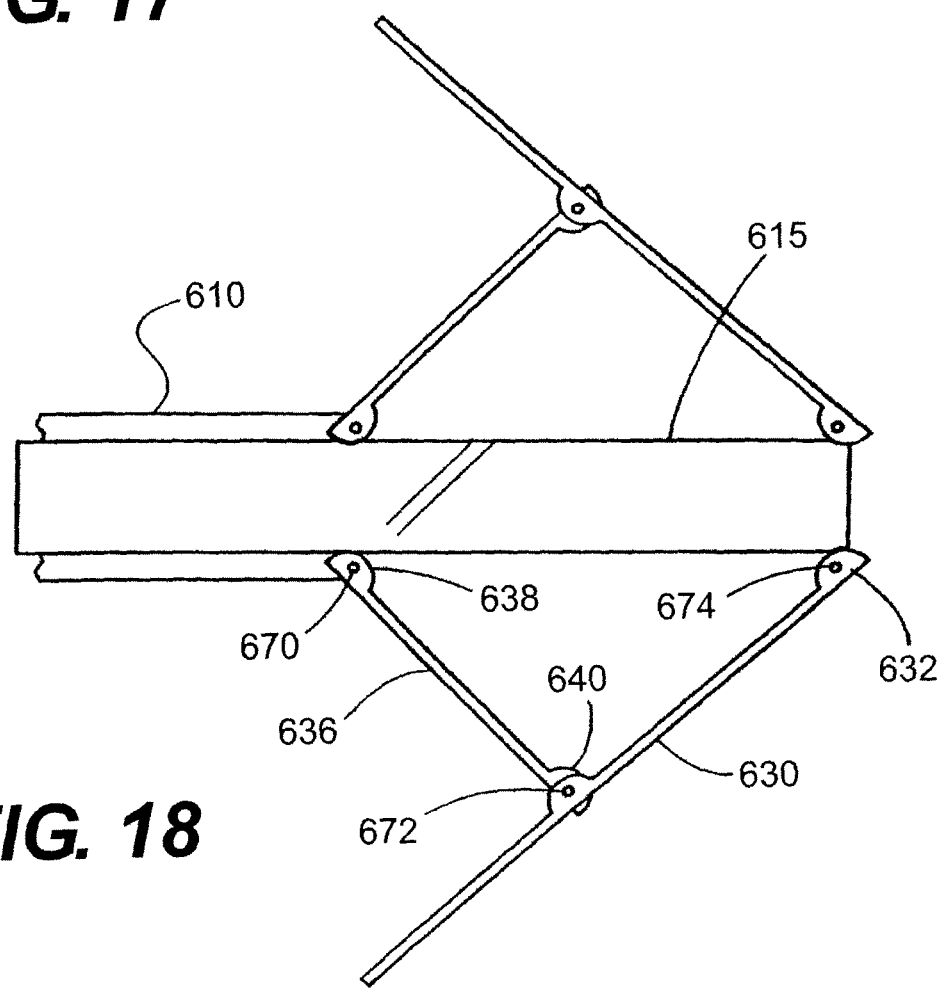

FIGS. 17 and 18 are schematic views illustrating the radial implant support arms 630 and the radial support struts 636 of the implant/delivery system array 600. In FIG. 17, a radial support strut 636 is pivotably attached at its proximal end 638 at a first pivotable joint 670 to the actuation catheter 610. The radial support strut 636 is attached at its distal end 640 to a second pivotable joint 672 at an intermediate point of a corresponding radial implant support arm 630. The radial implant support arm 630 is attached at its distal end 632 by a third pivotable joint 674 to the core catheter 620. FIG. 17 shows the assembly in a closed state. When the actuation catheter 610 is advanced distally over the core catheter 615, as shown by the arrows 676, the radial support strut 636 and the radial implant support arm 630 are extended by the motion at the first pivotable joint 670, the second pivotable joint 672, and the third pivotable joint 674, as shown by the arrow 678. This motion has the effect of expanding the deployment umbrella and folded implant (not shown in FIGS. 17 and 18), allowing it to achieve its greatest radial dimension, prior to engagement and implantation as previously discussed with reference to FIGS. 12-16.

Figure 20:
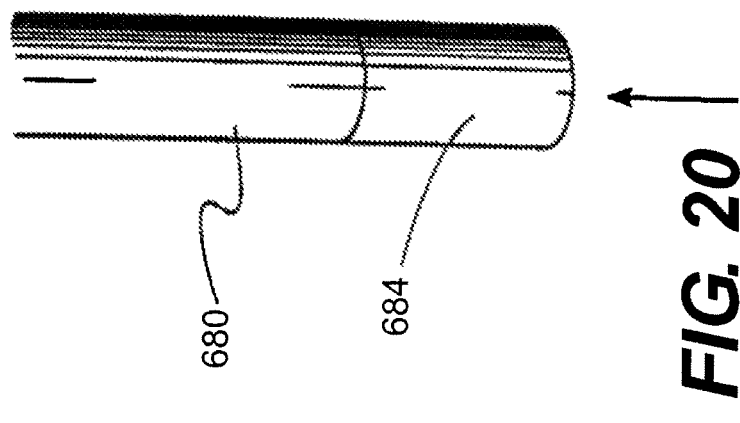
FIG. 20 is a perspective view of the lower end of the touchdown sensor of FIG. 19, showing the sensor in a compressed condition.
Figure 19:
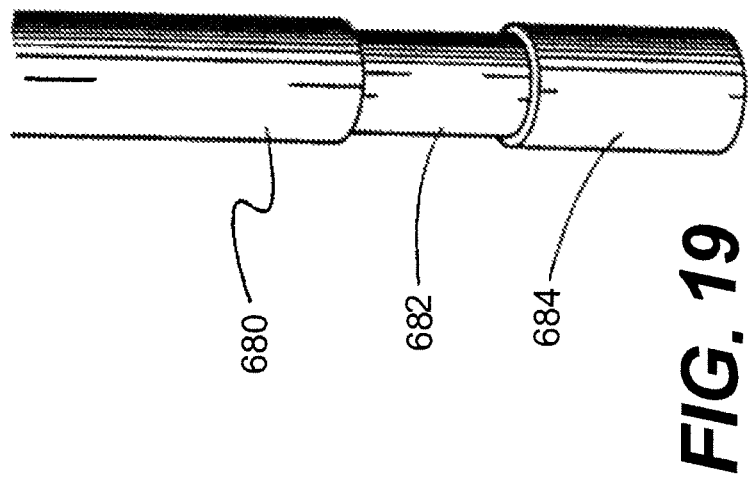
FIG. 19 is a perspective view of the lower end of a touchdown sensor of the implant of FIG. 12, showing the sensor in an uncompressed condition.

FIGS. 19 and 20 show further details of the touchdown sensors 648 shown previously in FIG. 12. The touchdown sensor 648 of FIGS. 19 and 20 includes a distal segment 680, an intermediate segment 682, and a proximal segment 684. The distal segment 680 is spring-mounted, so that it is capable of slidable, telescoping displacement over the intermediate segment 682 to achieve a seamless junction with the proximal segment 684 upon maximal displacement. When the touchdown sensor 648 is in its normal condition, the spring extends the proximal segment such that the sensor assumes the orientation shown in FIG. 19. When the implant 645 (FIG. 12) is seated against the periphery of an anatomical opening, the proximal segment 684 of the sensor 648 is compressed against the distal segment 680, as shown in FIG. 20. The distal segment 680 and the proximal segment 684 are both constructed of, are sheathed by, or otherwise covered with a radio-opaque material. However, the intermediate segment 682 is not constructed or coated with such a radio-opaque material. Therefore, when the distal segment 680 is at rest, it is fully extended from the proximal segment 684, and the gap represented by the exposed intermediate segment 682 is visible on radiographic examination. However, when the distal segment 680 is brought to maximum closeness with the proximal segment 684, no such radio-opaque gap is radiographically visible, and the touchdown sensor is said to be "activated". This embodiment allows radiographic monitoring of the position of the touchdown sensor 648 with respect to the degree of extension of the distal catheter segment 680. In the embodiment according to the present invention as shown, one or more touchdown detectors 648 are employed to ascertain that the delivery system for the prosthetic device is located in the proper position to deploy the implant into the mitral annulus. As this anatomic structure cannot be directly identified on fluoroscopy or standard radiographic procedures, such precise location could be otherwise difficult. At the same time, precise localization and engagement of the mitral annulus is critical for proper implant function and safety.

Touchdown detectors within the embodiments according to the present invention can have a multiplicity of forms, including the telescoping, spring-loaded, radio-opaque elements joined by a non-radio-opaque element as in the aforementioned examples. In embodiments employing magnetic resonance imaging, touchdown detectors according to the present invention may utilize metallic segments interposed by nonmetallic segments in a similar telescoping, spring-loaded array. Other embodiments include a visually-evident system with telescoping, spring-loaded elements with color-coded or other visual features for procedures in which direct or endoscopic observation would be possible. Still other embodiments of touchdown detectors according to the present invention include touchdown detectors provided with microswitches at their tips, such that momentary contact of sufficient pressure completes an electrical circuit and signals the activation of the touchdown detector to the operator. Still other touchdown detectors according to the present invention are provided with fiberoptic pathways for Rahmen laser spectroscopy or other spectral analytical techniques which are capable of detecting unique tissue qualities of the tissue at the desired site for implantation. In addition, still other embodiments according to the present invention include touchdown detectors containing electrodes or other electronic sensors capable of detecting and signaling the operator when a desired electrophysiologic, impedance, or other measurable quality of the desired tissue is detected for proper implantation. Such electrophysiologic touchdown detectors may include electrical circuits that produce visual, auditory, or other signals to the operator that the detectors are activated and that the implant is in the proper position for attachment.

In yet other embodiments according to the present invention, other intracardiac or extracardiac imaging techniques including, but not limited to, intravascular ultrasound, nuclear magnetic resonance, virtual anatomic positioning systems, or other imaging techniques may be employed to confirm proper positioning of the implant, obviating the need for the touchdown sensors as previously described.

Figure 21:
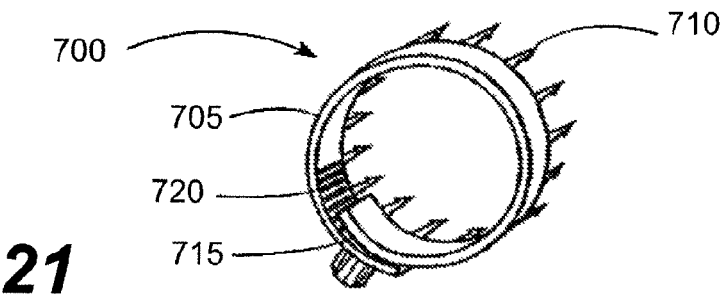
FIG. 21 is a perspective end view of a fourth embodiment of an implant for reducing the circumference of an anatomic orifice.
Figure 22:
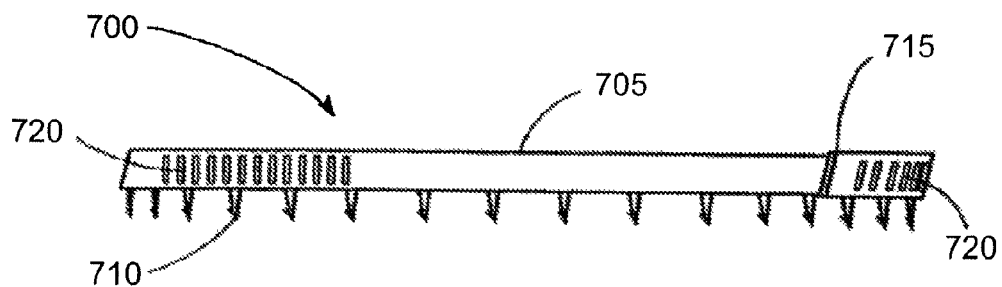
FIG. 22 is a side view of the implant of FIG. 21 with the implant opened up to show its full length.
Figure 23:
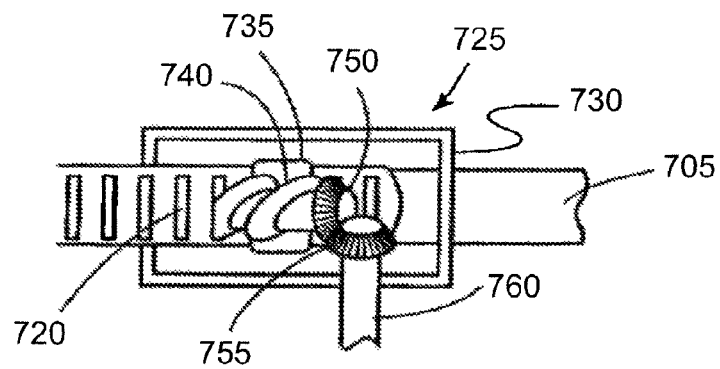
FIG. 23 is a side view of the adjustment mechanism of the implant of FIG. 21.

FIGS. 21-24 show an implant 700 according to one embodiment of the present invention. In this embodiment, the implant body 705 is bandlike and flexible. Through much of its length, the implant body 705 is provided with a series of retention barbs 710 which are oriented to facilitate placement, retention, and removal of the device. The implant body 705 is also provided with an adjustable section 715, which is provided in this example with a series of adjustment stops 720. The adjustment stops 720 may be slots, holes, detents, dimples, ridges, teeth, raised elements, or other mechanical features to allow measured adjustment of the implant 700 in use. In the embodiment shown in FIGS. 21-24, the adjustment stops 720 are engaged by a geared connector 725. FIG. 21 is an end view, showing the implant body 705 curved on itself, with the retention barbs 710 to the exterior, and with the adjustable section 715 passing through its engagement with the geared connector 725 and curving internally within the implant body 705 to form a closed, round structure. FIG. 23 shows details of an exemplary geared connector 725, in which a housing 730 is connected to the implant body 705. The housing 730 contains and supports a mechanical worm 740 with an attached first geared head 750 which mates with a second geared head 755. The second geared head 755 is attached to an adjustment stem 760 which is machined to receive a screwdriver-like adjustment element. The various embodiments according to the present invention may require a number of forms of adjustment elements. In the present example, the adjustment element is provided as a finely coiled wire with a distal tip machined to be received by a receiving slot in the adjustment stem 760 (not shown). The relationship between the distal tip of the adjustment element and the adjustment stem 760 is mechanically similar to a screwdriver bit and screwhead, such that torsion imparted to the adjustment means by the operator will result in the turning of the adjustment stem 760 and second geared head 755 allows motion of the first geared head 750 and worm 740, which creates motion of the adjustable implant section 715 as the worm engages with the series of adjustment tops 725. Excess length of the adjustable section 715 passes though a band slot 735 (FIG. 23), thus allowing the band to move concentrically inside the closed implant body 705. The adjustment element in this embodiment may be designed to remain in place after the deployment umbrella has been retracted and withdrawn. The connection between the adjustment element's distal tip and the adjustment stem 760 may be a simple friction connection, a mechanical key/slot formation, or may be magnetically or electronically maintained.

Figure 24:
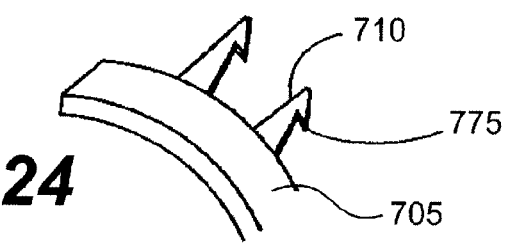
FIG. 24 is a close-up view of two of the retention barbs of the implant of FIG. 21.

As further shown in FIG. 21, the exemplary embodiment employs unidirectional retention barbs 710 which are attached to the outer perimeter of the implant body 705. The retention barbs 710 are oriented in a consistent, tangential position with respect to the implant body 705 such that rotational motion of the implant body will either engage or release the retention barbs 710 upon contact with the desired tissue at the time of deployment. This positioning of the retention barbs 710 allows the operator to "screw in" the implant 700 by turning the implant 700 upon its axis, thus engaging the retention barbs 710 into the adjacent tissue. As shown in FIG. 24, the retention barbs 710 may each be further provided with a terminal hook 775 at the end which would allow for smooth passage through tissue when engaging the retention barbs 710 by rotating the implant 700, without permitting the implant 700 to rotate in the opposite direction, because of the action of the terminal hooks 775 grasping the surrounding tissue (much like barbed fish hooks). The terminal hooks 775 thus ensure the seating of the implant 700 into the surrounding tissue.

FIGS. 25-27 illustrate another embodiment of an implant 800 as contemplated according to the present invention. The implant 800 includes a band 805 (FIG. 27), but the retention barbs of the previous example have been eliminated in favor of an outer fabric implant sheath 810. The fabric sheath 810 can be sutured or otherwise affixed to the anatomic tissue in a desired location. The circumference of the implant body 800 is adjusted through a geared connector 825 similar to the geared connector of the bandlike implant array shown in FIG. 23. More specifically, adjustment stops 820 on the band are engaged by a mechanical worm 840 with an attached first geared head 850. The first geared head 850 mates with a second geared head 855. The second geared head 855 is attached to an adjustment stem 860 which is machined to receive a screwdriver-like adjustment element.

Figure 28:
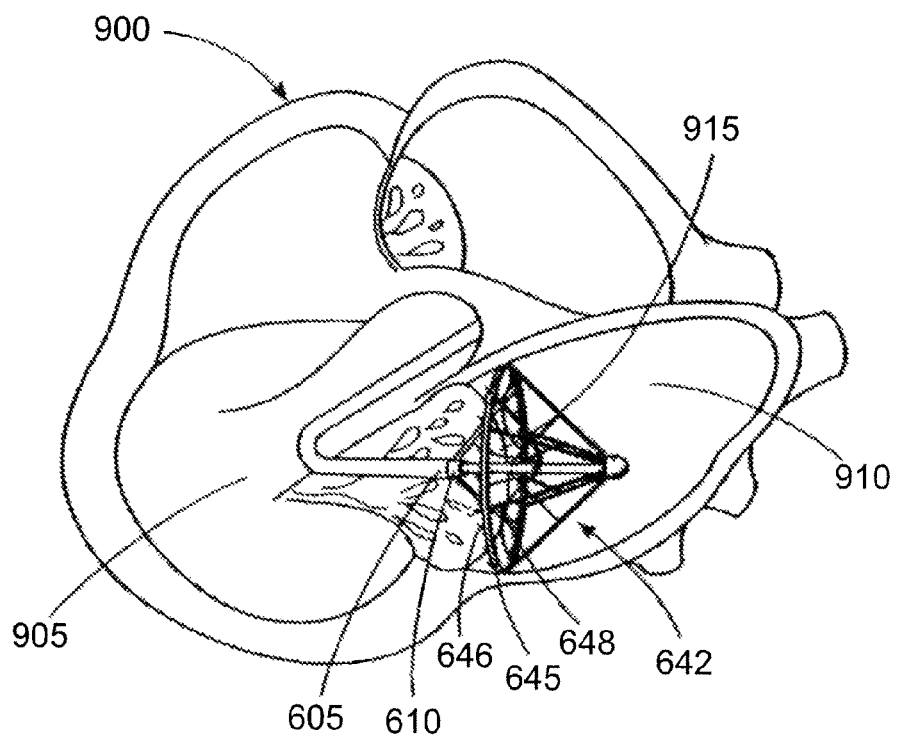
FIG. 28 is a schematic view showing the implant of FIG. 12 anatomically positioned at the mitral annulus in a heart with the implant in a fully expanded state.

FIG. 28 illustrates an example of the method of use of an implant/delivery system array 600 for positioning an implant 645 in a patient with ischemic annular dilatation and mitral regurgitation. Peripheral arterial access is obtained via conventional cutdown, arterial puncture, or other standard access techniques. After access to the arterial system is attained, guidewire placement is performed and intravascular access to the heart 900 is obtained using fluoroscopic, ultrasound, three-dimension ultrasound, magnetic resonance, or other real-time imaging techniques. The guidewire, deployment device, and implant are passed through the aortic valve in a retrograde fashion into the left ventricle 905 and then into the left atrium 910. At this point, the operator retracts the housing sheath 605, thus unsheathing the collapsed deployment umbrella 642 and implant 645. The deployment umbrella 642 is then distended by the distal motion of the actuation catheter, causing the radial support arms and struts to fully distend. At this point, the touchdown detectors 648 are not in contact with any solid structures, and are fully extended with their radiolucent gaps visible on the imaging system. Once the deployment umbrella is distended, the entire assembly is pulled back against the area of the mitral valve 915. At least two touchdown detectors 648 are employed in a preferred embodiment according to the present invention. When all touchdown detectors show the disappearance of their intermediate, non-opaque, intermediate segments and are thus activated, then the deployment umbrella must be in contact with the solid tissue in the region of the mitral annulus/atrial tissue, and further implant deployment and adjustment may proceed. However, if any one touchdown sensor is not activated, and a radiolucent gap persists, then the device is not properly positioned, and must be repositioned before further deployment. Thus, the touchdown sensor system may assist in the deployment and adjustment of prosthetic devices by the delivery system according to the present invention. Once properly positioned, the operator rotates the actuation catheter in a prescribed clockwise or counterclockwise manner to engage the retention barbs on the implant into the tissue in the region of the mitral annulus/atrial tissue. Should re-positioning be required, a reverse motion would disengage the retention barbs from the annular/atrial tissue, and repositioning may be performed, again using the touchdown detectors for proper placement. Once firmly seated, the adjustment element(s) are operated to achieve the desired degree of annular reduction. Real-time trans esophageal echocardiography, intravascular echocardiography, intracardiac echocardiography, or other modalities for assessing mitral function may then be employed to assess the physiologic effect of the repair on mitral function, and additional adjustments may be performed. Once a desired result has been achieved, the release elements are activated to detach the implant from the deployment umbrella. The operator then retracts the actuation catheter and extends the housing sheath, collapsing the deployment umbrella and covering the components for a smooth and atraumatic withdrawal of the device from the heart and vascular system.

If desired, the adjustment elements may be left in position after the catheter components are withdrawn for further physiologic adjustment. In yet other embodiments according to the present invention, a catheter-based adjustment elements may subsequently be re-inserted though a percutaneous or other route. Such an adjustment element may be steerably operable by the operator, and may be provided with magnetic, electronic, electromagnetic, or laser-guided systems to allow docking of the adjustment element with the adjustable mechanism contained within the implant. In still other embodiments, the adjustment mechanism may be driven by implanted electromechanical motors or other systems, which may be remotely controlled by electronic flux or other remote transcutaneous or percutaneous methods.

In the case of pulmonic valve repair, initial catheter access is achieved through a peripheral or central vein. Access to the pulmonary valve is also achieved from below the valve once central venous access is achieved by traversing the right atrium, the tricuspid valve, the right ventricle, and subsequently reaching the pulmonic valve.

In yet other embodiments according to the present invention, catheter access to the left atrium can be achieved from cannulation of central or peripheral veins, thereby achieving access to the right atrium. Then a standard atrial trans-septal approach may be utilized to access the left atrium by creation of an iatrogenic atrial septal defect (ASD). In such a situation, the mitral valve may be accessed from above the valve, as opposed to the retrograde access described in Example 1. The implant and a reversed deployment umbrella may be utilized with implant placement in the atrial aspect of the mitral annulus, with the same repair technique described previously. The iatrogenic ASD may then be closed using standard device methods. Access to the aortic valve may also be achieved from above the aortic valve via arterial access in a similar retrograde fashion.

Figure 29:
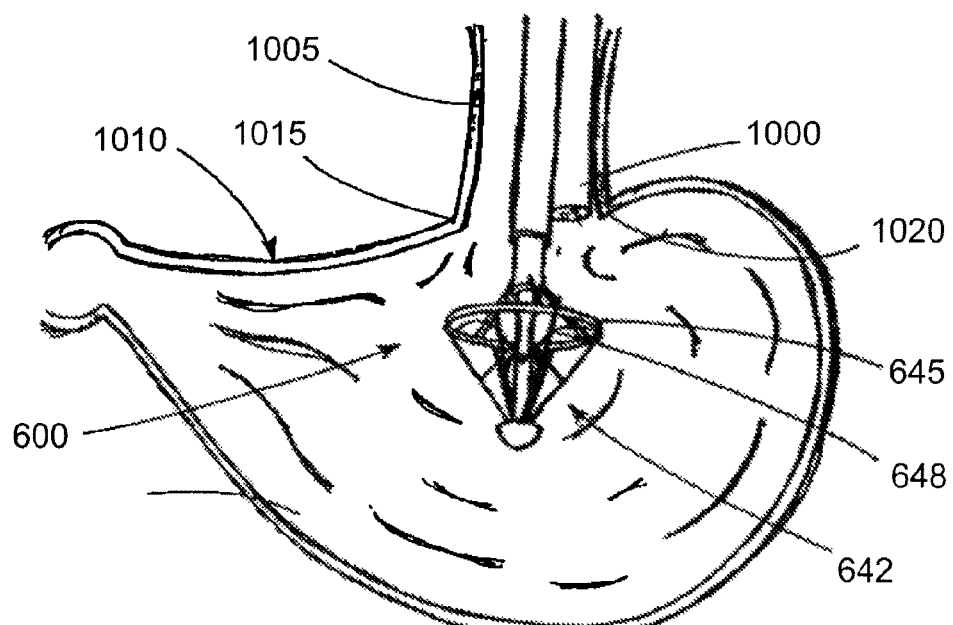
FIG. 29 is a schematic view showing the implant of FIG. 12 anatomically positioned at the gastroesophageal opening with the implant in a fully expanded state.
Figure 30:
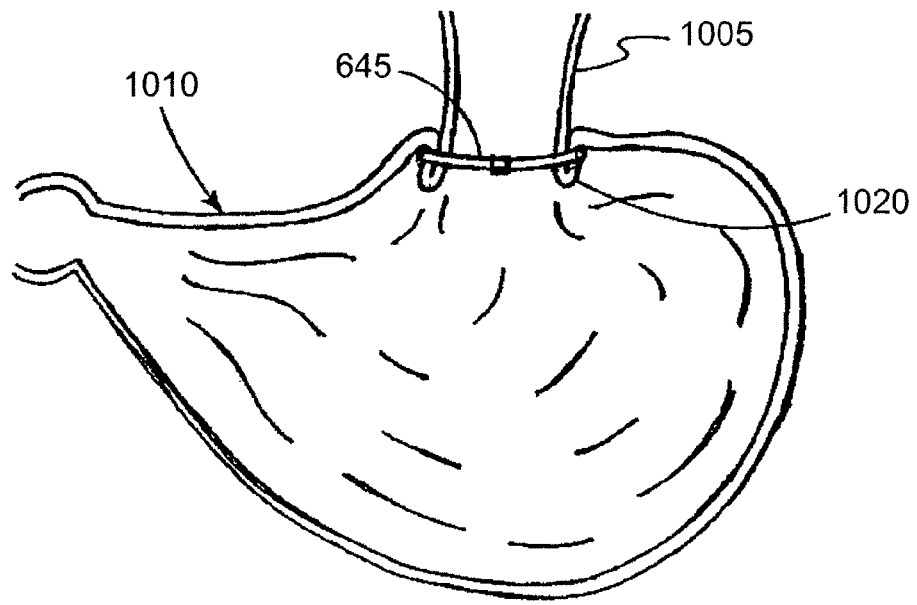
FIG. 30 is a schematic view showing the implant of FIG. 29 implanted to reduce the circumference of the gastroesophageal opening.

Other embodiments of the adjustable implant and methods according to the present invention include gastrointestinal disorders such as gastro-esophageal reflux disease (GERD), a condition in which the gastro-esophageal (GE) junction lacks adequate sphincter tone to prevent the reflux of stomach contents into the esophagus, causing classic heartburn or acid reflux. This not only results in discomfort, but may cause trauma to the lower esophagus over time that may lead to the development of pre-cancerous lesions (Barrett's esophagus) or adenocarcinoma of the esophagus at the GE junction. Surgical repair of the GE junction has historically been achieved with the Nissen Fundoplication, an operative procedure with generally good results. However, the Nissen procedure requires general anesthesia and a hospital stay. Utilizing the devices and methods according to the present invention, an adjustable implant would obviate the need for a hospital stay and be performed in a clinic or gastroenterologist's office. Referring now to FIGS. 29 and 30, an umbrella deployment device 600 with implant 645 is passed under guidance of an endoscope 1000, through the patient's mouth, esophagus 1005, and into the stomach 1010, where the deployment device 600 is opened with expansion of the implant 645 and touchdown detectors 648 with a color-coded or otherwise visible gap. The touchdown detectors are then engaged onto the stomach around the gastroesophageal junction 1015 under direct endoscopic control until all touchdown detectors 648 are visually activated. The implant is then attached to the stomach wall, 1020 the umbrella 642 is released and withdrawn, leaving behind the implant 645 and the adjustment elements. The implant is then adjusted until the desired effect is achieved, i.e., minimal acid reflux either by patient symptoms, pH monitoring of the esophagus, imaging studies, or other diagnostic means. If the patient should suffer from gas bloat, a common complication of gastroesophageal junction repair in which the repair is too tight and the patient is unable to belch, the implant can be loosened until a more desirable effect is achieved.

In various embodiments anticipated by the present invention, the implant body may be straight, curved, circular, ovoid, polygonal, or some combination thereof. In various embodiments anticipated by the present invention the implant may be capable of providing a uniform or non-uniform adjustment of an orifice or lumen within the body. The implant body may further completely enclose the native recipient anatomic site, or it may be provided in an interrupted form that encloses only a portion of the native recipient anatomic site. In still other embodiments of the present invention, the implant body may be a solid structure, while in yet other embodiments the implant body may form a tubular or otherwise hollow structure. In one embodiment of the present invention, the body may further be a structure with an outer member, an inner member, and optional attachment members. In such an embodiment, the outer member of the implant body may serve as a covering for the implant, and is designed to facilitate and promote tissue ingrowth and biologic integration to the native recipient anatomic site. The outer member in such an embodiment may be fabricated of a biologically compatible material, such as Dacron, PTFE, malleable metals, other biologically compatible materials or a combination of such biologically compatible materials in a molded, woven, or non-woven configuration. The outer member in such an embodiment also serves to house the inner member. In this embodiment, the inner member provides an adjustment means that, when operated by an adjustment mechanism, is capable of altering the shape and/or size of the outer member in a defined manner.

In alternate embodiments according to the present invention, the adjustment means may be located external to or incorporated within the outer member. In yet additional alternate embodiments contemplated by the present invention, the implant body may consist of an adjustment means without a separate outer member covering said adjustment means.

In various embodiments according to the present invention, the adjustment means may include a mechanism which may be threaded or non-threaded, and which may be engaged by the action of a screw or worm screw, a friction mechanism, a friction-detent mechanism, a toothed mechanism, a ratchet mechanism, a rack and pinion mechanism, or such other devices to permit discreet adjustment and retention of desired size a desired position, once the proper size is determined.

In yet other embodiments according to the present invention, the adjustment means may comprise a snare or purse string-like mechanism in which a suture, a band, a wire or other fiber structure, braided or non-braided, monofilament or multifilament, is capable of affecting the anatomic and/or physiologic effects of the implant device on a native anatomic recipient site upon varying tension or motion imparted to said wire or fiber structure by a surgeon or other operator. Such an adjustment means may be provided as a circular or non-circular structure in various embodiments. Changes in tension or motion may change the size and/or shape of the implant.

In various embodiments according to the present invention, the adjustment means may be a metallic, plastic, synthetic, natural, biologic, or any other biologically-compatible material, or combination thereof. Such adjustment means may further be fabricated by extrusion or other molding techniques, machined, or woven. Furthermore, in various embodiments of the present invention, the adjustment means may be smooth or may include slots, beads, ridges, or any other smooth or textured surface.

In various embodiments of the present invention, the implant body may be provided with one or more attachment members such as grommets or openings or other attachment members to facilitate attachment of the implant to the native recipient site. In alternate embodiments, the implant body may attach to or incorporate a mechanical tissue interface system that allows a sutureless mechanical means of securing the implant at the native recipient site. In still other alternate embodiments, sutures or other attachment means may be secured around or through the implant body to affix the implant body to the native recipient site. In yet other embodiments of the present invention, mechanical means of securing the implant body to the native recipient site may be augmented or replaced by use of fibrin or other biologically-compatible tissue glues or similar adhesives.

In additional various embodiments according to the present invention, the adjustable implant may be employed to adjustably enlarge or maintain the circumference or other dimensions of an orifice, ostium, lumen, or anastomosis in which a disease process tends to narrow or constrict such circumference or other dimensions.

In various embodiments according to the present invention, an adjustment mechanism may be provided to interact with the adjustment means to achieve the desired alteration in the size and/or position of the adjustment means. Such an adjustment mechanism may include one or more screws, worm-screw arrays rollers, gears, frictional stops, a friction-detent system, ratchets, rack and pinion arrays, micro-electromechanical systems, other mechanical or electromechanical devices or some combination thereof.

In some embodiments as contemplated by the present invention, an adjustment tool may be removably or permanently attached to the adjustment mechanism and disposed to impart motion to the adjustment mechanism and, in turn, to the adjustment means to increase or decrease the anatomic effect of the implant on the native recipient site.

In alternate embodiments according to the present invention, micromotor arrays with one or more micro-electromechanical motor systems with related electronic control circuitry may be provided as an adjustment means, and may be activated by remote control through signals convey by electromagnetic radiation or by direct circuitry though electronic conduit leads which may be either permanently or removably attached to said micromotor arrays.

In still other various embodiments according to the present invention, the adjustment mechanism may be provided with a locking mechanism disposed to maintain the position of the adjustment means in a selected position upon achievement of the optimally desired anatomic and/or physiologic effect upon the native recipient site and the bodily organ to which it belongs. In other embodiments, no special locking mechanism may be necessary due to the nature of the adjustment means employed.

In yet other alternate embodiments according to the present invention, the adjustment means and/or the outer member structure may be a pliable synthetic material capable of rigidification upon exposure to electromagnetic radiation of selected wavelength, such as ultraviolet light. In such embodiments, exposure to the desired electromagnetic radiation may be achieved by external delivery of such radiation to the implant by the surgeon, or by internal delivery of such radiation within an outer implant member using fiberoptic carriers placed within said outer member and connected to an appropriate external radiation source. Such fiberoptic carriers may be disposed for their removal in whole or in part from the outer implant member after suitable radiation exposure and hardening of said adjustment means.

The present invention also provides methods of using an adjustable implant device to selectively alter the anatomic structure and/or physiologic effects of tissues forming a passageway for blood, other bodily fluids, nutrient fluids, semi-solids, or solids, or wastes within a mammalian body. Various embodiments for such uses of adjustable implants include, but are not limited to, open surgical placement of said adjustable implants at the native recipient site through an open surgical incision, percutaneous or intravascular placement of said implants under visual control employing fluoroscopic, ultrasound, magnetic resonance imaging, or other imaging technologies, placement of said implants through tissue structural walls, such as the coronary sinus or esophageal walls, or methods employing some combination of the above techniques. In various embodiments as contemplated by the present invention, adjustable implants may be placed and affixed in position in a native recipient anatomic site by trans-atrial, trans-ventricular, trans-arterial, trans-venous (i.e., via the pulmonary veins) or other routes during beating or non-beating cardiac surgical procedures or endoscopically or percutaneously in gastrointestinal surgery.

Furthermore, alternate methods for use of an adjustable implant device may provide for the periodic, post-implantation adjustment of the size of the anatomic structure receiving said implant device as needed to accommodate growth of the native recipient site in a juvenile patient or other changes in the physiologic needs of the recipient patient.

Adjustment of the adjustable implants and the methods for their use as disclosed herein contemplates the use by the surgeon or operator of diagnostic tools to provide an assessment of the nature of adjustment needed to achieve a desired effect. Such diagnostic tools include, but are not limited to, transesophageal echocardiography, echocardiography, diagnostic ultrasound, intravascular ultrasound, virtual anatomic positioning systems integrated with magnetic resonance, computerized tomographic, or other imaging technologies, endoscopy, mediastinoscopy, laparoscopy, thoracoscopy, radiography, fluoroscopy, magnetic resonance imaging, computerized tomographic imaging, intravascular flow sensors, thermal sensors or imaging, remote chemical or spectral analysis, or other imaging or quantitative or qualitative analytic systems.

In one aspect, the implant/delivery system of the present invention comprises a collapsible, compressible, or distensible prosthetic implant and a delivery interface for such a prosthetic implant that is capable of delivering the prosthetic implant to a desired anatomic recipient site in a collapsed, compressed, or non-distended state, and then allowing controlled expansion or distension and physical attachment of such a prosthetic implant by a user at the desired anatomic recipient site. Such a system permits the delivery system and prosthetic implant to be introduced percutaneously through a trocar, sheath, via Seldinger technique, needle, or endoscopically through a natural bodily orifice, body cavity, or region and maneuvered by the surgeon or operator to the desired anatomic recipient site, where the delivery system and prosthetic implant may be operably expanded for deployment. When desirable, the implant/delivery system according to the present invention is also capable of allowing the user to further adjust the size or shape of the prosthetic implant once it has been attached to the desired anatomic recipient site. The delivery system according to the present invention is then capable of detaching from its interface with the prosthetic implant and being removed from the anatomic site by the operator. The delivery system and prosthetic implant may be provided in a shape and size determined by the anatomic needs of an intended native recipient anatomic site within a mammalian patient. Such a native recipient anatomic site may be a heart valve, the esophagus near the gastro-esophageal junction, the anus, or other anatomic sites within a mammalian body that are creating dysfunction that might be relieved by an implant capable of changing the size and shape of that site and maintaining a desired size and shape after surgery.

In various embodiments contemplated by the present invention, the delivery system may be a catheter, wire, filament, rod, tube, endoscope, or other mechanism capable of reaching the desired recipient anatomic site through an incision, puncture, trocar, or through an anatomic passageway such as a vessel, orifice, or organ lumen, or trans-abdominally or trans-thoracically. In various embodiments according to the present invention, the delivery system may be steerable by the operator. The delivery system may further have a delivery interface that would retain and convey a prosthetic implant to the desired recipient anatomic site. Such a delivery interface may be operably capable of distending, reshaping, or allowing the independent distension or expansion of such a prosthetic implant at the desired recipient anatomic site. Furthermore, such a delivery interface may provide an operable means to adjust the distended or expanded size, shape, or physiologic effect of the prosthetic implant once said implant has been attached in situ at the desired recipient anatomic site. In various embodiments according to the present invention, such adjustment may be carried out during the procedure in which the implant is placed, or at a subsequent time. Depending upon the specific anatomic needs of a specific application, the delivery interface and the associated prosthetic implant may be straight, curved, circular, helical, tubular, ovoid, polygonal, or some combination thereof. In still other embodiments of the present invention, the prosthetic implant may be a solid structure, while in yet other embodiments the prosthetic implant may form a tubular, composite, or otherwise hollow structure. In one embodiment of the present invention, the prosthetic implant may further be a structure with an outer member, an inner member, and optional attachment members. In such an embodiment, the outer member of the prosthetic implant may serve as a covering for the implant, and is designed to facilitate and promote tissue ingrowth and biologic integration to the native recipient anatomic site. The outer member in such an embodiment may be fabricated of a biologically compatible material, such as Dacron, PTFE, malleable metals, other biologically compatible materials or a combination of such biologically compatible materials in a molded, woven, or non-woven configuration. The outer member in such an embodiment also serves to house the inner member. In this embodiment, the inner member provides an adjustment means that, when operated by an adjustment mechanism, is capable of altering the shape and/or size of the outer member in a defined manner.

In some embodiments according to the present invention, at least some portions of the adjustable inner or outer member may be elastic to provide an element of variable, artificial muscle tone to a valve, sphincter, orifice, or lumen in settings where such variability would be functionally valuable, such as in the treatment of rectal incontinence or vaginal prolapse. In various embodiments according to the present invention, the delivery interface would have an attachment means to retain and convey the prosthetic implant en route to the native anatomic recipient site and during any in situ adjustment of the prosthetic implant once it has been placed by the operator. Such an attachment means would be operably reversible to allow detachment of the prosthetic implant from the delivery interface once desired placement and adjustment of the prosthetic implant has been accomplished.

Figure 31:
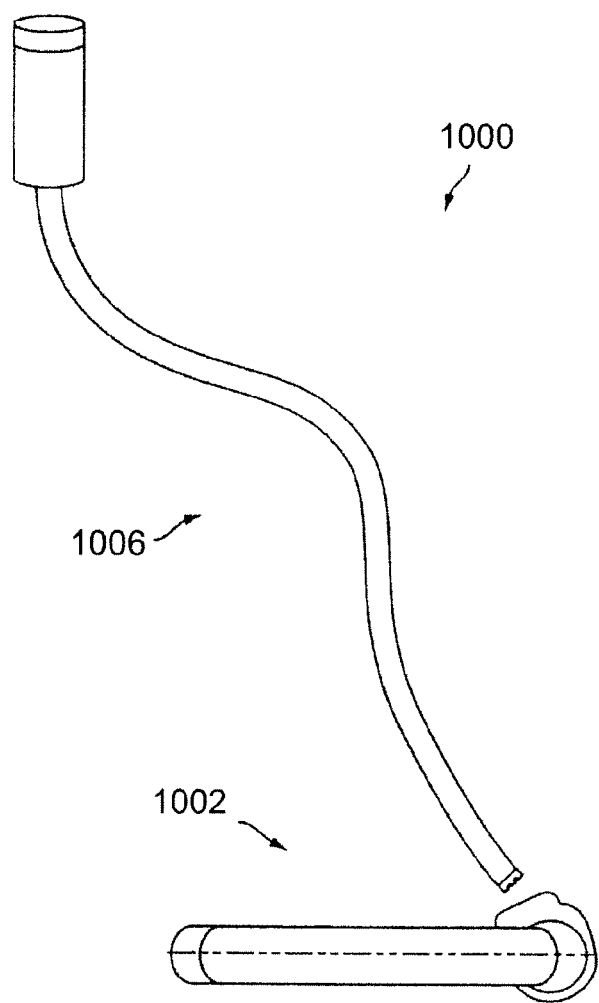
FIG. 31 is a schematic view of an embodiment of an implantable device of the present invention.

In one embodiment of the present invention, illustrated in FIG. 31, an implantable device system 1000 for controlling at least the size or shape of an anatomical structure or lumen includes an implantable device 1002 and an adjustment tool 1006. The anatomical structure or lumen is an anatomic site with dysfunction that can be relieved by the implantable device 1002 to change a size or shape of the anatomic site.

Figure 32A:
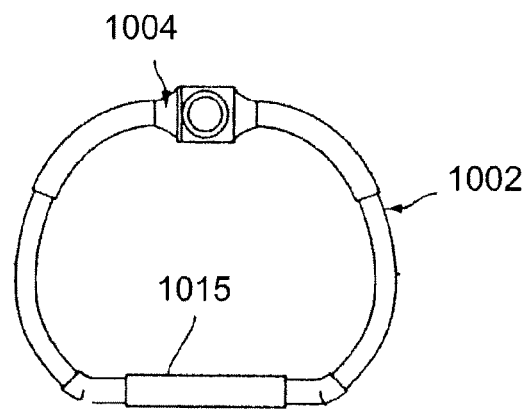
FIG. 32A is a schematic view of another embodiment of an implantable device of the present invention.
Figure 32:
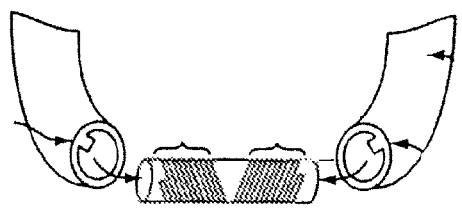
FIG. 32B is a schematic view of a threaded member in an embodiment of an implantable device of the present invention.

FIG. 32A is a schematic of the implant device 1002 without showing an optional flexible outer tube and fabric sheath. FIG. 32B is a schematic of a disassembled portion of implantable device 1002 with retaining tube 1015 removed.

Figure 36:
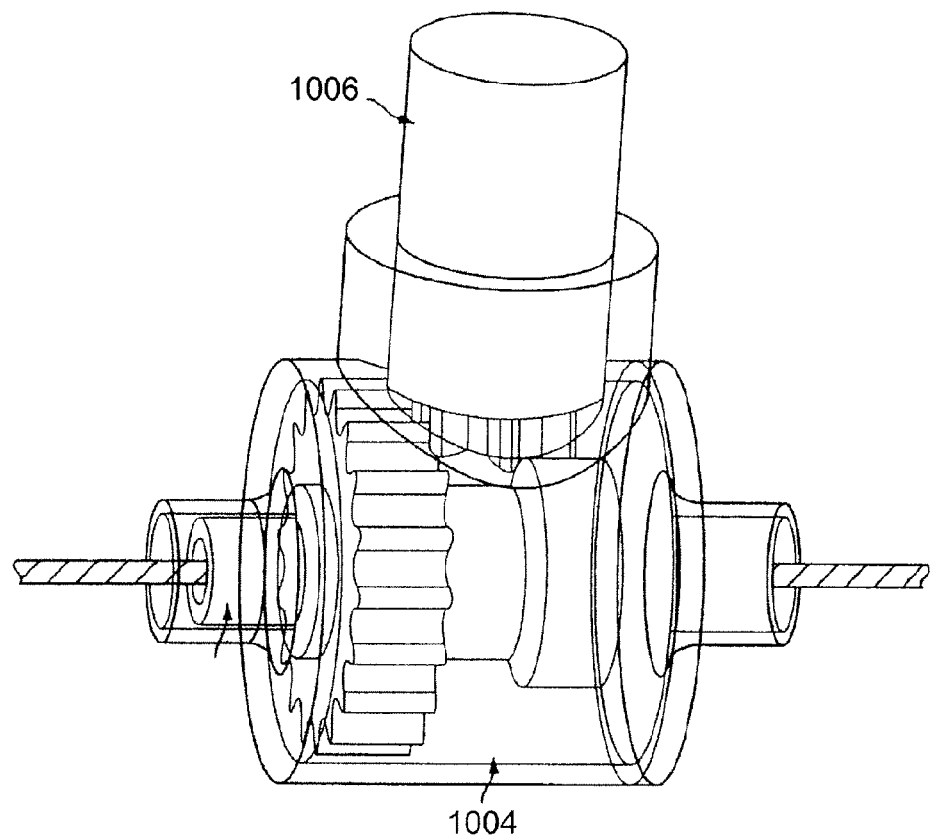
FIG. 36 is a schematic view of an embodiment of an adjustable member of the present invention, with the distal tip of the adjustment tool coupled to the adjustment member.

In another embodiment of the present invention, illustrated in FIGS. 33 through 36, the adjustable member 1004 provides translated motion through rotation. FIGS. 33 through 35 illustrate a theory of operation of an embodiment of the present invention, while FIG. 36 shows details of the adjustment member 1004.

Figure 37:
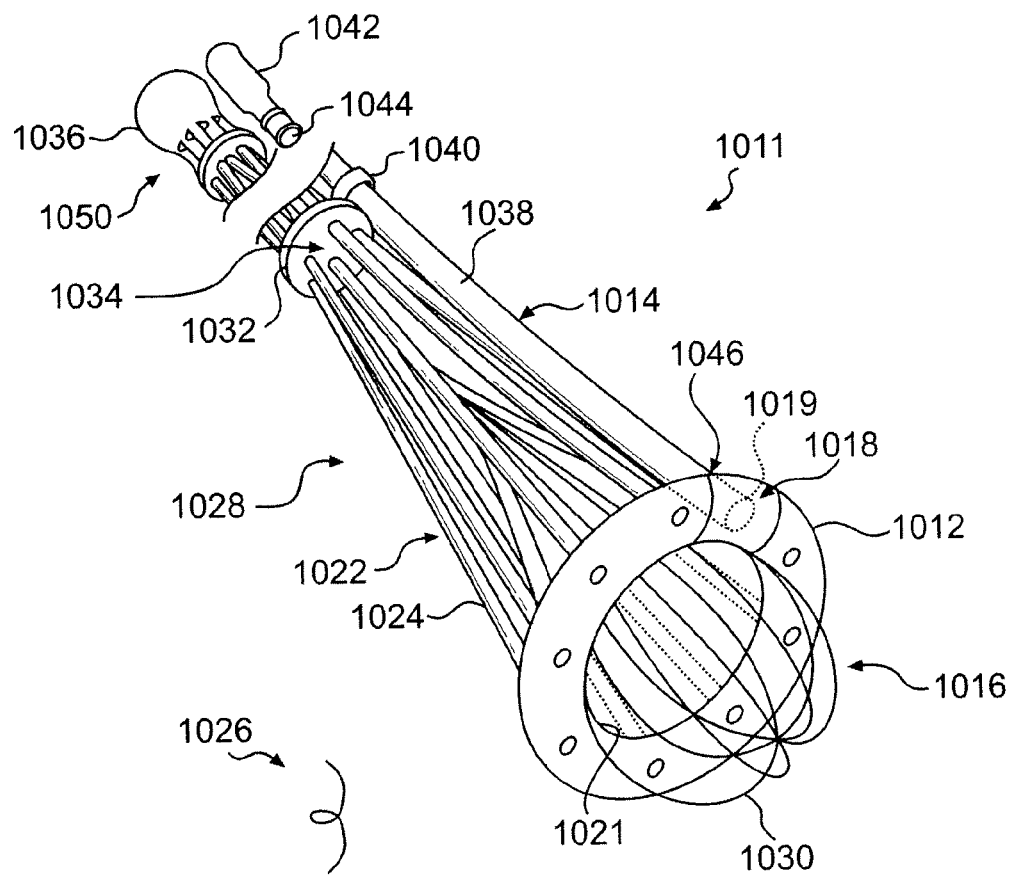
FIG. 37 provides a schematic view of portion of elements of a system having features of the invention including an adjustable implant device, an adjustment tool, and an adjustable implant device positioning element.

FIG. 37 provides a schematic view of portions of elements of a system 1011 having features of the invention including an adjustable implant tdevice 1012, an adjustment tool, 1014, and an adjustable implant device positioning element 1016. As illustrated in FIG. 37, an adjustable implant device 1012 having features of the invention has an adjustment member 1018 configured to engage an adjustment too 1014, the adjustment member 1018 having an adjustment tool coupler 1019 which serves as the interface between an adjustment tool 1014 and an adjustment member 1018. An adjustment tool coupler 1019 may include a slot or other receptacle to receive an end of an adjustment tool 1014, or may have a protuberance such as a ridge, a tee-shape, a hexagonal shape, or other engagement element configured to mate with and engage an adjustment tool 1014. An adjustable implant device 1012 has a perimeter, such as a perimeter 1021 as indicated in FIG. 37, or other perimeter associated with a substantially circumferential dimension. A perimeter 1021 or other perimeter may be adjusted (e.g., increased or decreased in magnitude) by operation of an adjustment tool 1014 engaged with an adjustment tool coupler. It will be understood that an adjustable implant device 1012 has additional dimensions, configurations, and orientations, some or all of which may be adjusted or altered by an operator, such as by using an adjustment tool 1014, during use of the device.

Also illustrated in the system 1011 shown schematically in FIG. 37 is an adjustable implant device holding element 1022, illustrated as a plurality of elongated structures 1024 which attach to the adjustable implant device 1012 (as indicated by small circles spaced around the adjustable implant device 1012) effective to hold the adjustable implant device 1012 during its, and effective to release the adjustable implant device 1012 upon its fixation to target tissue. The elongated structures 1024 may be struts, or columns, or other supporting structures configured to move and guide an adjustable implant device 1012 to a desired location, preferably under the direction and control of an operator. The elongated structures 1024 may also serve as housings or guides for securing elements 1026 configured to attach and to hold an adjustable implant device 1012 to tissue. In the embodiment illustrated in FIG. 37, the adjustable implant device holding element 1022, made up of a plurality of elongated structures 1024, forms a virtual enclosure 1028 which surrounds an implant device positioning element 1016, shown in FIG. 37 as a whisk shape made up of a plurality of thin flexible elements 1030, such as tines, wires or flexible rods. Each tine may be made with a compliant material that allows the structure to be easily collapsed to a contracted configuration, for example, under the influence of an external constraint or force, yet allows ready expansion to an expanded configuration when external constraint is removed.

In embodiments of systems 1011 having features of the invention, securing elements 1026 may be housed, during initial placement of an adjustable implant device 1012, within elongated structures 1024 that are hollow, and then may be deployed from within the hollow elongated structures 1024 effective to secure the adjustable implant device 1012 to tissue. It will be understood that, in embodiments, a securing element 1026 may be disposed on, or around an adjustable implant holding element 1022, and need not be housed within an adjustable implant holding element 1022 which serves as a securing element housing 1024. Securing elements 1026 may engage an adjustable implant device 1012 by passing through the device 1012 (e.g., passing through a fabric coating of the device 1012), or through elements of the device 1012 (e.g., passing through rings or eyelets of the device 1012), or may enclose or compress a device 1012 in order to secure it to tissue. Securing elements 1026 may pass into tissue, and adhere to tissue by their shape, with barbs, or hooks, and may pass into and then out of tissue effective to adhere to, or attach to, tissue. Securing elements 1026 may be made of a single material or composition, such as a resilient material effective to pierce and penetrate tissue, and to assume a non-linear shape within tissue; may include a staple or hook portion; or may have separate elements, such as, for example, a needle or hook portion and a suture or thread portion. In embodiments of the systems, devices and methods having features of the invention, securing elements 1026 may assume shapes selected from a curve, a loop, a coil, a spiral coil, a barb, a bifurcation, and an anchor shape.

The virtual enclosure 1028, made up of elongated structures 1024, which surrounds an implant device positioning element 1016, may have its shape maintained by an implant holding element guide 1032. An implant holding element guide 1032 having features of the invention is configured to support and guide the elongated structures 1024 that are part of the adjustable implant holding element 1022. An implant holding element guide 1032 may have an aperture 1034 for passage of a positioning element 1016. As illustrated in FIG. 37, an adjustable implant holding element 1022 may have a handle 1036 for manipulation and control of the adjustable implant holding element 1022 and of the adjustable implant device 1012.

An adjustment tool 1014 has a tool shaft 1038 for control of the adjustment tool 1014 by an operator or by operating machinery positioned at a distance from the adjustable implant device 1012. An adjustable implant holding element 1022 may have a tool guide 1040, for example, as illustrated in the embodiment shown in FIG. 37, a loop enclosing a portion of tool shaft 1038 to constrain movement of the tool shaft 1038 without constraining its rotation or ability to move or be displaces along longitudinal directions. A handle 1042 allows manipulation and control of an adjustment tool 1014. A tool shaft 1038 may be solid, or may be hollow. A hollow tool shaft 1038 may enclose a tool internal element 1044, which may be a rotary element, effective to allow rotation of a tool tip portion 1046. A tool tip portion 1046 may be configured to engage with an adjustment member 1018, for example by means of engaging with an adjustment tool coupler 1019, and may have elements, or a shape, configured to engage complementary elements or shapes on an adjustment tool coupler 1019. A tool internal element 1044 may include wires, cables, hydraulic, pneumatic, or other coupling elements effectivelo control a tool tip portion 1046 effective that the tip portion 1046 may cause or guide the operation of an adjustment tool coupler 1019 to effect the operation of an adjustment member 1018 effective to adjust an adjustable implant device 1012.

In embodiments, an implant holding element 1022 may have a handle 1036 with a securing element control 1048 or a plurality of securing element controls 1048. A securing element control 1048 may be configured, for example, to deploy a securing element 1026 from within a housing 1024 effective that the securing element 1026 secures an adjustable implant device 1012 to tissue. For example, as illustrated in FIG. 37, a securing element control 1048 may be a slider disposed on a handle 1036 and operably connected with an internal element 1049 effective to deploy a securing element 1026. For example, an internal element 1049 may be a plunger, connected with control 1048 that may move longitudinally within a housing 1024 and push on a securing element 1026 housed within the housing 1024. Such a securing element 1026 may be, for example, a stressed, pointed wire housed within housing 1024 which, upon exiting the housing 1024 penetrates tissue and assumes a coiled configuration effective to hold the tissue and to enclose an adjustable implant device 1012, securing the adjustable implant device 1012 to the tissue.

A tool guide 1040 may be configurable between different configurations. For example, in embodiments, a tool guide 1040 may assume a holding position and may assume a releasing position. A tool guide control 1050, which may be disposed on a handle 1036 as illustrated in FIG. 37, may be provided in order to control the configuration of a tool guide 1040. A tool guide control 1050 may be operably connected with a tool guide 1040 effective to open or close a loop, where a tool guide 1040 includes a loop through which a tool shaft 1038 passes. In other embodiments, a tool guide control 1050 may be operably connected with an element, such as a magnetic element, where a tool guide 1040 comprises a coupling, such as a magnetic coupling, configured to guide a tool shaft 1038, effective to engage or disengage the tool guide 1040 with the tool shaft 1038.

An implant holding element guide 1032 having an aperture 1034 may be effective to guide and direct a positioning element 1016 during operation of the positioning element. A positioning element 1016 may be used to guide an adjustable implant device 1012 to a desired position adjacent an anatomical orifice or lumen. In embodiments, where, for example, a target anatomical orifice or lumen is a heart valve such as a mitral valve, an implant holding element guide 1032 may aid in directing the adjustable implant device 1012 to a position adjacent tissue surrounding the heart valve, such as the mitral valve, effective that the adjustable implant device 1012 may be secured to tissue adjacent the valve and effective that the adjustable implant device 1012 adjust and improve the function of the valve.

Operation of a handle 1036 to position, orient, or reconfigure an adjustable implant holding element 1022 and an adjustable implant holding element guide 1032 allows an operator to position an adjustable implant positioning element 1016 and so to position an adjustable implant device 1012 in desired orientations and positions. In embodiments, for example, a positioning element 1016 may be disposed to pass through an aperture 1034 in an implant holding element guide 1032, the configuration of the aperture 1034 and the guide 1032 being effective to guide positioning element 1016, and to constrain or direct its lateral (or radial) movement while allowing movement or displacement in a longitudinal direction. As is discussed in the following, longitudinal displacement of the positioning element 1016 distal to the adjustable implant device 1012 allows placement of a distal portion 1017 of a positioning element 1016 adjacent to, or within, an anatomical orifice or lumen. Such placement of a distal portion 1017 of a positioning element 1016 serves to guide subsequent placement of an adjustable implant device 1012 into proper position adjacent a target anatomical orifice or lumen, such as a heart valve, e.g., a mitral valve.

As shown in FIG. 37, a positioning element 1016 may have a whisk shape made up of a plurality of thin flexible elements 1030, such as wires or flexible rods. In embodiments, a positioning element 1016 may have a fenestrated surface, such as a plurality of holes or apertures, or be made from a mesh, or made from an interlocking network of material. Such holes or apertures may include covers configured to allow fluid flow in at least one direction. Thus, in embodiments, a positioning element 1016 may be configured to allow passage of fluid, such as blood or other physiological fluid, including artificial physiological fluids, through the surface defined by the material making up positioning element 1016. A positioning element 1016 is configured for placement at a desired location within a heart, a blood vessel, or other anatomical location in which fluid may flow, and may be configured to allow fluid flow while in place at that anatomical location. While allowing fluid flow, a positioning element 1016 may also configured to interact with tissue so as to guide the positioning of an adjustable implant device 1012 to a desired position adjacent a target anatomical orifice or lumen.

Thus, for example, a positioning element 1016 carrying an adjustable implant device 1012, as illustrated in FIG. 37, may be positioned within a heart atrium, such as a left atrium; a distal portion 1017 of the positioning element 1016 may be placed within a heart valve, such as a mitral valve, displacing valve leaflets while allowing blood flow through the valve while the distal portion 1017 of the positioning element 1016 is in place within the valve. Interaction of such a positioning element 1016 with the valve and adjacent tissue is effective to position the adjustable implant device 1012 at a desired position in contact with valve tissue and/or tissue adjacent the valve. The placement of a distal portion 1017 of the positioning element 1016 may thus be effective to guide and position the adjustable implant device 1012 to a desired position effective that the adjustable implant device is positioned for repair or improvement of function of the valve. When so positioned, the adjustable implant device 1012 may be secured to tissue, may be adjusted for optimal improvement of valve function, and the positioning device 1016 and other elements of a system 1011 having features of the invention may be removed, leaving the adjustable implant device 1012, securing elements 1026, and optionally other elements in place effective to control the shape of the valve. Such control of the shape of the valve is effective to improve the operation and function of the valve, and, where necessary, to repair the valve to restore or improve its function. It will be understood that similar actions using systems 1011 having features of the invention may be performed with other valves, including valves not in the heart, and with other anatomical orifices and lumens, including anatomical orifices and lumens in the gastrointestinal system and in other organ systems.

In embodiments of devices 1012 and systems 1011 having features of the invention, a positioning element 1016 may be configured so that fluid flow itself may aid, guide, or control the positioning of a device 1012 to a desired position adjacent a target anatomical orifice or lumen. Thus, a positioning element 1016 may be configured so that flow or passage of fluid, such as blood or other physiological fluid, including artificial physiological fluids, towards or through the surface defined by the material making up positioning element 1016 is effective to urge, guide, or position a positioning element 1016 towards and/or at a desired location within a heart, a blood vessel, or other anatomical location in which fluid may flow. As discussed above, a positioning element 1016 may be configured to allow fluid flow while in place at that anatomical location. While allowing fluid flow, a positioning element 1016 may also configured to interact with tissue so as to guide the positioning of an adjustable implant device 1012 to a desired position adjacent a target anatomical orifice or lumen. Thus, a positioning element 1016 may be configured so that contact of the positioning element 1016 with tissue, or flow or passage of fluid, or both, may be effective to urge, guide, or position a positioning element 1016 towards and/or at a desired location within a heart, a blood vessel, or other anatomical location in which, or towards which, fluid may flow.

Figure 38A:
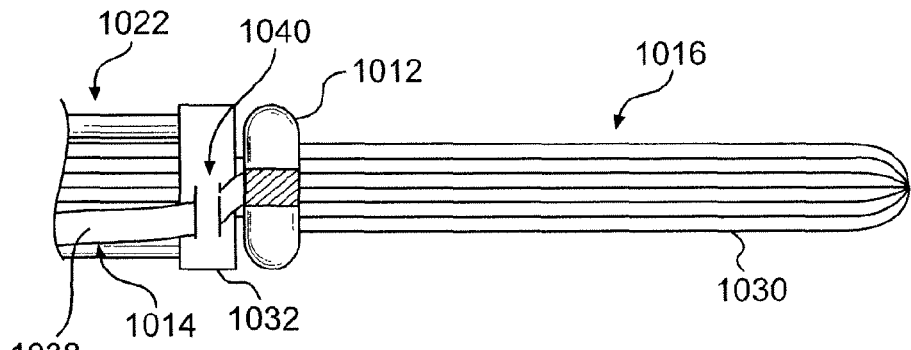
FIG. 38A-C provide a partial side view of a system having features of the invention including an adjustable implant device, an adjustment tool, and an adjustable implant device positioning element; where
Figure 38B:
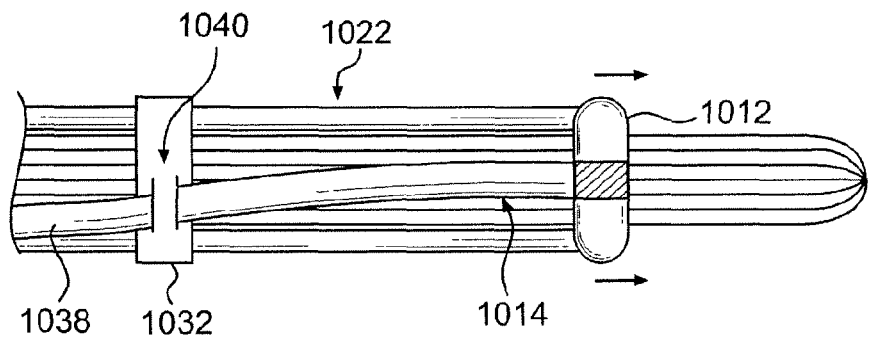
Figure 38C:
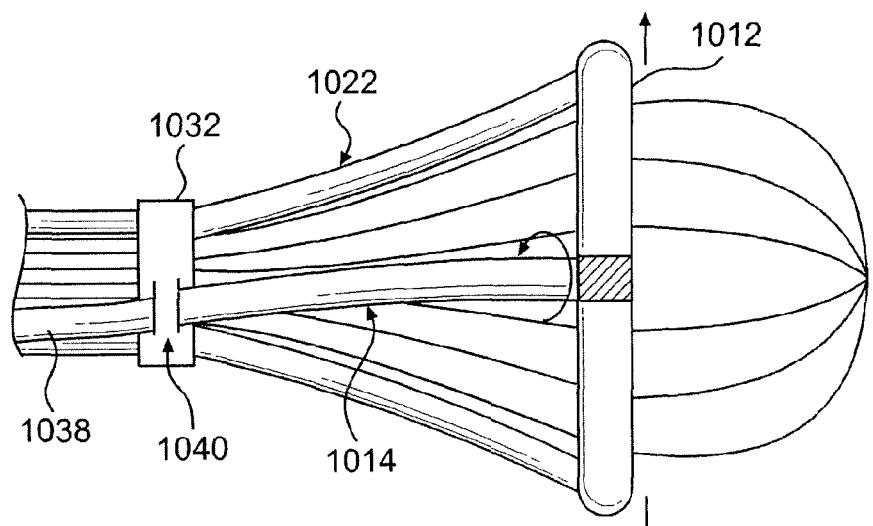

As illustrated in FIG. 38, an adjustable implant device 1012 disposed around a positioning element 1016, and having an adjustment tool 1014 operably connected with the adjustment member 1018 of the adjustable implant device 1012, may assume different configurations having different sizes. For example, as shown in FIG. 38, an adjustable implant device 1012 may assume a configuration with a reduced diameter and a reduced perimeter (e.g., FIG. 38A) and may assume a configuration with an increased diameter and a increased perimeter (e.g., FIG. 38B). As is also illustrated in FIGS. 38A, B, and C, an adjustable implant device 1012 disposed around a positioning element 1016 may be moved, or may assume different positions, along a longitudinal dimension of the positioning element 1016. Longitudinal movement of the adjustable implant device 1012 is indicated in FIG. 38B by straight arrows pointing to the right in the figure; radial increase in the size of the adjustable implant device 1012 is indicated by straight arrows pointing in vertical directions in FIG. 38C. It will be understood that longitudinal movement may be in the opposite direction as the direction shown in FIG. 38B, and that radial size changes may be to decrease the size of an adjustable implant 1012, opposite to that illustrated in FIG. 38C. It will be further understood that an adjustable implant device 1012 having features of the invention may not have a circular configuration, but may have other shapes and orientations than the exemplary one illustrated in the figures, and that size changes may not be radial changes alone, but may include orientation, angular changes, non-planar changes, asymmetrical changes, breaks or discontinuities, and other alterations of the size, shape, orientation, and configuration of an adjustable implant device 1012 having features of the invention.

Operation of tool 1014 may be effective to adjust a size and/or a shape of the adjustable implant device 1012. For example, operation of tool 1014 may be effective to adjust a size (e.g., the diameter and the perimeter) of the adjustable implant device 1012. Operation of tool 1014 may be effective to adjust a shape of the adjustable implant device 1012 (e.g., asymmetric actions, such a reduction in a dimension so that one side and not the other side of the adjustable implant device 1012 is shortened, so that a perimeter is reduced while one side of the adjustable implant device 1012 is unchanged or changed by a lesser amount than the other side). In embodiments, adjustment of an adjustable implant device 1012 is effected by operation of a tool 1014 engaged with an adjustment member 1018, typically via an adjustment tool coupler 1019. Operation of tool 1014 is indicated by the curved arrow in FIG. 38C. A tool 1014 may have a shaft 1038 guided by a tool guide 1040, as illustrated in FIGS. 38 A, B, and C. In alternative embodiments, there is no tool guide 1040. Operation of a tool 1014 may be by rotation, effective to rotate a shaft 1038 or an internal element 1044, or may be by other means of effecting adjustment of an adjustable implant device 1012.

An adjustable implant device 1012 may be secured to tissue by any suitable means, including by sutures, staples, clips, adhesives, grafts, or other attachment means. Any suitable means known in the art may be used to secure an adjustable implant device 1012 in place effective to adjust a dimension of an anatomic orifice or lumen. Examples of securing devices suitable for securing an adjustable implant device 1012 are shown FIG. 39. A securing element 1026 may have a tip portion 1052, a medial portion 1054 and a proximal portion 1056. A securing device 1026 may be configured to be delivered to an anatomic site by a system 1011, such as, e.g., by being carried within a housing 1024, or by being carried on a surface of a holding element 1022. In embodiments, a securing element 1026 may assume a particular configuration within a housing 1024, and may assume a different configuration outside of the housing 1024. A securing element 1026 may include a resilient material and may assume a first configuration, such as a substantially linear configuration, within a housing due to the physical constraint of the housing 1024, and may assume an unstrained, non-linear second configuration when disposed outside of the housing 1024. In embodiments of securing elements 1026 having features of the invention, a securing element 1026 may include shape memory materials, or composites such as bimetallic strips, that alter shape upon changes in environmental conditions.

Figure 39A:
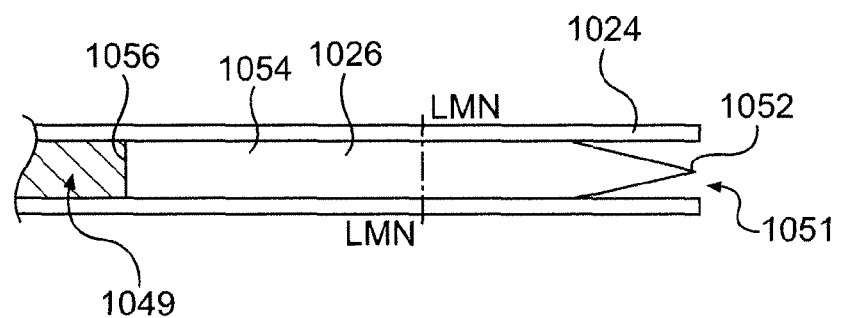
FIG. 39A-D shows partial cut-away views of securing element housings and securing elements; where
Figure 39B:
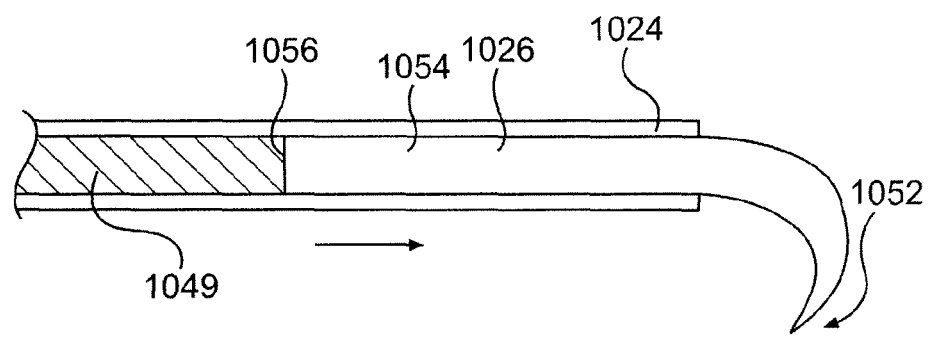
Figure 39C:
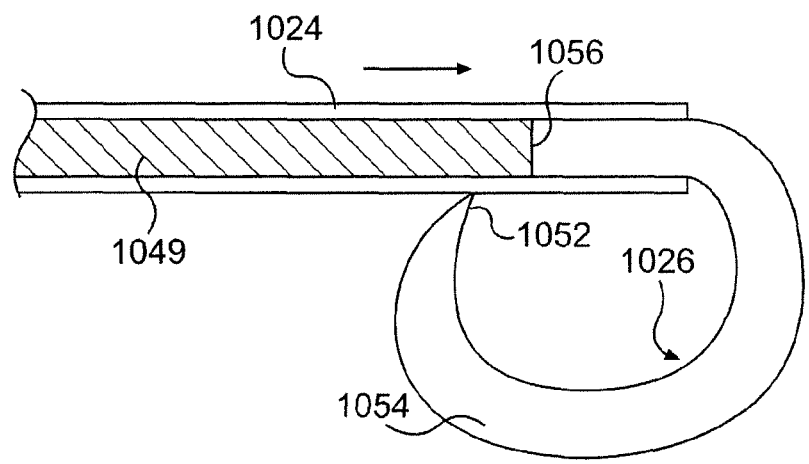
Figure 39D:
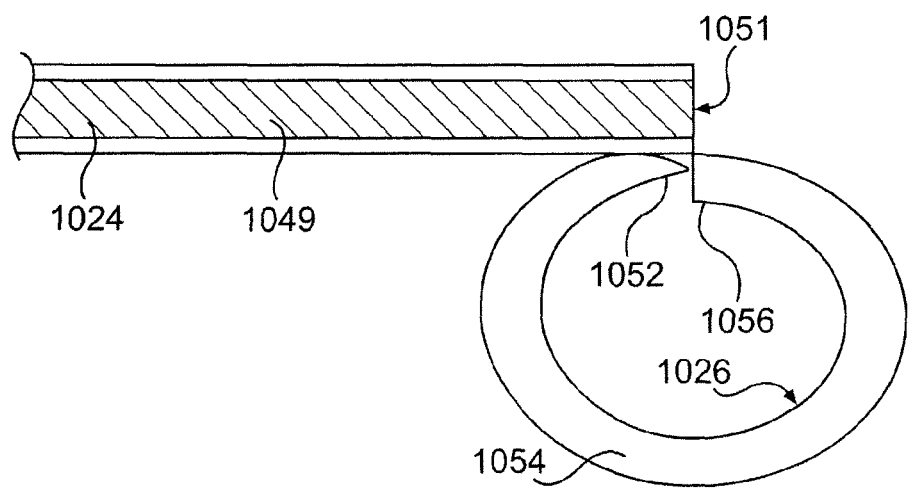
Figure 39E:
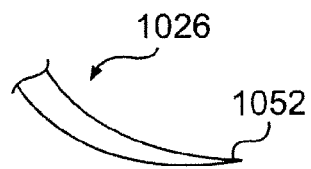
FIG. 39E shows a partial schematic side view of a securing element released from a securing element housing and having a curved configuration.
Figure 39F:
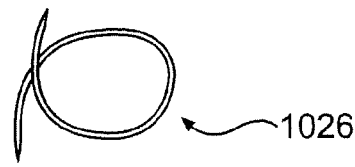
FIG. 39F shows a partial schematic side view of a securing element released from a securing element housing and having a looped configuration.
Figure 39I:
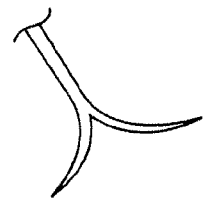
FIG. 39I shows a partial schematic side view of a securing element released from a securing element housing and having a bifurcated configuration.
Figure 39G:
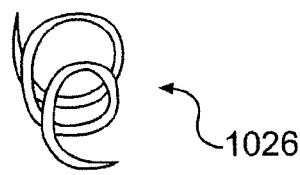
FIG. 39G shows a partial schematic side view of a securing element released from a securing element housing and having a spiral-coiled configuration.
Figure 39J:
FIG. 39J shows a partial schematic side view of a securing element released from a securing element housing and having a hooked configuration.
Figure 39H:
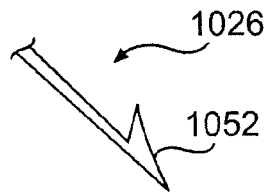
FIG. 39H shows a partial schematic side view of a securing element released from a securing element housing and having a barbed configuration.
Figure 39K:
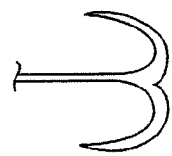
FIG. 39K shows a partial schematic side view of a securing element released from a securing element housing and having a anchor-shaped configuration.
Figure 39N:
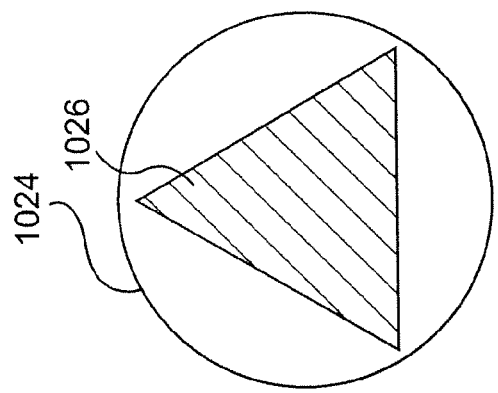
FIG. 39N shows a partial cross-sectional view of a housing and a securing element within the housing, the section taken along line LMN-LMN of FIG. 39A, showing a securing element having a triangular cross-sectional shape.
Figure 39M:
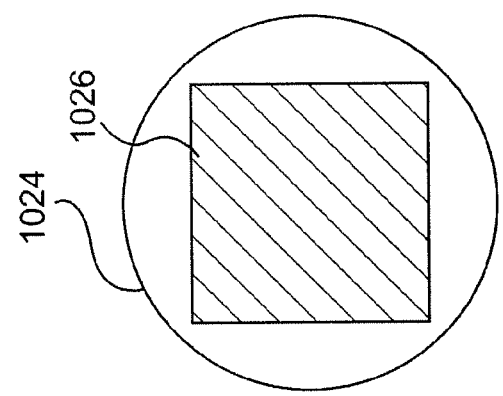
FIG. 39M shows a partial cross-sectional view of a housing and a securing element within the housing, the section taken along line LMN-LMN of FIG. 39A, showing a securing element having a square cross-sectional shape.

For example, in embodiments, a securing element 1026 may be constrained into a straight configuration within a housing 1024, as illustrated in FIG. 39A, and may be configured to assume a curved configuration outside of the housing 1024, as illustrated in FIG. 39B. For example, a securing element 1026 may be a spring clip or other deformable holding element, which may be loaded within a housing 1024 and ejected from a housing 1024 by a pushrod or plunger 1049. Such a securing element 1026 may be pre-shaped to have a curved, coiled, barbed, or other shape when free of constraint, and may be able to assume a straight or other shape suitable for placement within a housing 1024. As illustrated in the examples shown in FIGS. 39A and 39B, a securing element 1026 may be disposed within a distal portion of a housing 1024, and may be displaced outwardly of a port 1051 from the housing 1024 by action an internal element 1049 (shown here as a plunger 1049). In embodiments, an internal element 1049 within a housing 1024 contacts a proximal portion 1056 of a securing element 1026 and pushes it longitudinally effective to cause the tip portion 1052 to exit the port 1051. As indicated in FIG. 39B, tip portion 1052 may assume a non-linear configuration after exiting port 1051. Further longitudinal displacement of a plunger 1049 causes further longitudinal displacement of the securing element 1026, and a greater amount of the securing element 1026, including a medial portion 1054 as well as tip portion 1052, emerges from port 1051, and the securing element 1026 assumes further curvature, as illustrated in the example shown in FIG. 39C. As illustrated in the example of FIG. 39D, further longitudinal advancement of plunger 1049 causes further longitudinal displacement of the securing element 1026, so that the entire securing element 1026, including proximal portion 1056, is pushed out of port 1051, fully deploying the securing element 1026, which is shown having assumed the configuration of a substantially closed curve (e.g., a substantially closed ring).

In embodiments, a tip portion 1052 includes a sharp portion suitable for penetrating tissue. As a securing element 1026 is displaced longitudinally from a housing 1024, a tip portion 1052 may penetrate tissue. In embodiments, as a securing element 1026 is displaced longitudinally from a housing 1024, a tip portion 1052 may pass through or penetrate at least a portion of an adjustable implant device 1012. In embodiments, as a securing element 1026 is displaced longitudinally from a housing 1024, a tip portion 1052 may pass through or penetrate at least a portion of an adjustable implant device 1012 and may penetrate tissue.

Figure 39L:
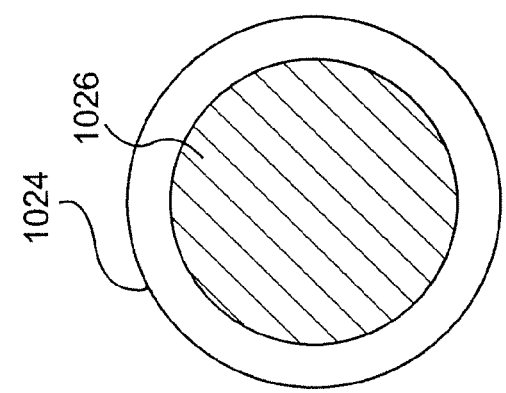
FIG. 39L shows a partial cross-sectional view of a housing and a securing element within the housing, the section taken along line LMN-LMN of FIG. 39A, showing a securing element having a circular cross-sectional shape.

It will be understood that a securing element 1026 may assume any configuration suitable for attaching to tissue, including, for example, needles, needles with suture, barbs, hooks, and other penetrating and attaching shapes. Examples of configurations of a securing element 1026 having features of the invention and suitable for attaching to tissue include curved, looped, spiral coiled, barbed, bifurcated, hooked, and anchor-shaped configurations. A securing element 1026 having features of the invention may have any suitable cross-sectional configuration. As illustrated in FIGS. 39L, M and N, which provide partial cross-sectional views of housings 1024 and securing elements 1026, and showing the securing elements 1026 within the housings 1024, the cross-sectional shape of a securing element 1026 (as taken along the line LMN-LMN shown in FIG. 39 A) may be, e.g., circular, square, or triangular. Other cross-sectional shapes, including oval, ridged, clover-shaped, or other shapes may also be used for securing elements 1026 having features of the invention. The cross-sectional shape may aid the securing element 1026 to assume the proper configuration upon exit from the housing 1024, and may aid in orienting the securing element 1026 in proper position or orientation upon exit from the housing 1024. Securing elements 1026 may be made of any suitable material, including, for example, metal, composite, plastic, shape-memory material such as a shape-memory metal (e.g., nitinol), or mixtures, alloys and combinations thereof.

Figure 40D:
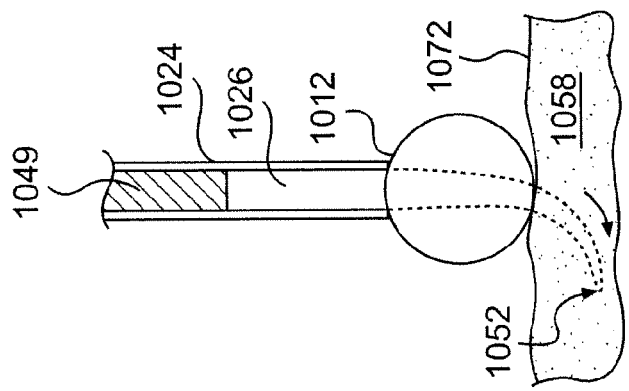
FIG. 40A-G are a series of schematic partial cross-sectional illustrations showing deployment of a securing element from a housing to secure an adjustable implant device to tissue, where
Figure 40C:
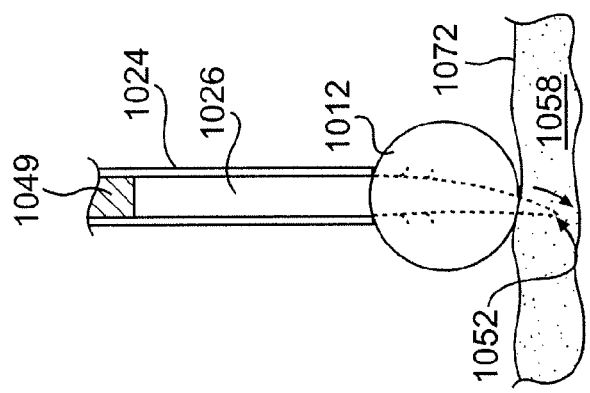
Figure 40B:
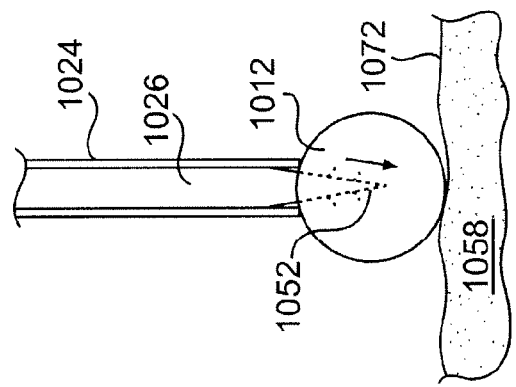
Figure 40A:
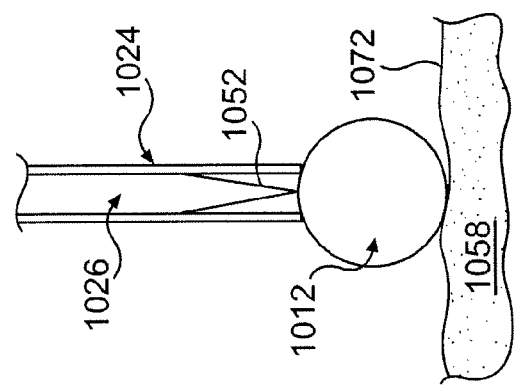
Figure 40G:
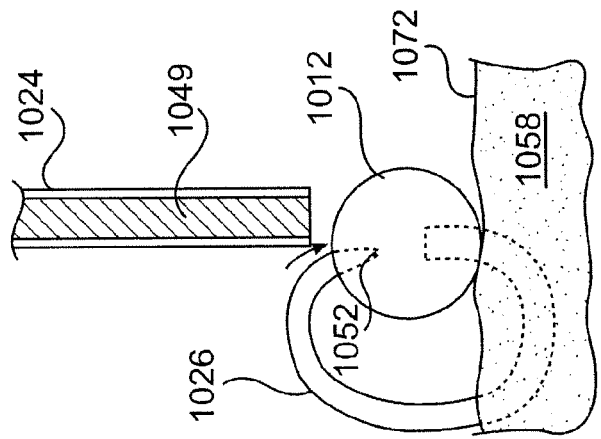
Figure 40F:
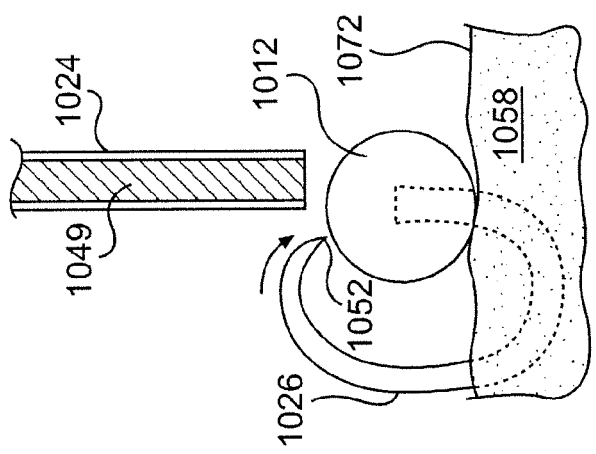
Figure 40E:
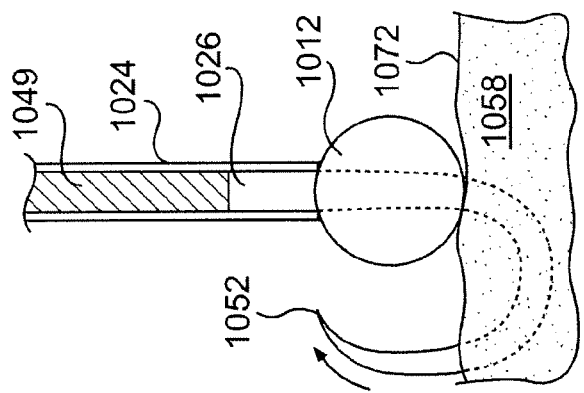

FIGS. 40A-G illustrate one method of attachment of an adjustable implant device 1012 to tissue 1058. These figures show penetration by a securing element 1026 of a portion of adjustable implant device 1012, of tissue surface 1072 and advancement into adjacent tissue 1058 (FIGS. 40A-D). Note the curvature of the securing element 1026 within the tissue 1058 shown in these figures. Further advancement of the securing element 1026 through the adjustable implant device 1012 and tissue 1058, and further curvature of the securing element 1026, leads to exit of tip portion 1052 from tissue surface 1072, as illustrated in FIG. 40E. Due to its curvature, tip portion 1052 exits tissue 1058 from the same tissue surface 1072 through which it entered tissue 1058. Still further advancement of the securing element 1026 through the adjustable implant device 1012 and tissue 1058, and further curvature of the securing element 1026, leads to additional contact with, and penetration of, the adjustable implant device 1012, as illustrated in FIGS. 40F and G. Note that a smaller and smaller portion of the securing element 1026 remains within housing 1024 as plunger 1049 advances to push securing element 1026 in a distal direction. As indicated in FIGS. 40F and G, advancement of plunger 1049 may be effective to push securing element 1026 completely out of housing 1024 and to deploy securing element 1026. In the configuration shown in FIG. 40G, securing element 1026 is deployed from the housing 1024, and is thus free of the adjustable implant holding element 1022, and is configured effective to secure the adjustable implant device 1012 to tissue 1058. As indicated by FIG. 40F, a securing element 1026 may include a tip portion 1052 that may curve back sufficiently to approach the surface of an adjustable implant device 1012 after having penetrated the adjustable implant device 1012 and tissue 1058 to secure the adjustable implant device 1012 to the tissue 1058. As indicated by FIG. 40G, a securing element 1026 may include a tip portion 1052 that may curve back even further than as shown in FIG. 40F, so as to re-enter the surface of an adjustable implant device 1012 after having penetrated the adjustable implant device 1012 and tissue 1058 to secure the adjustable implant device 1012 to the tissue 1058. Either configuration is effective to secure an adjustable implant device 1012 to the tissue 1058.

An adjustable implant device 1012 may be configured for penetration by a securing element 1026. For example, an adjustable implant device 1012 may have a passage element 1060 configured to accept a securing element 1026 and allow its passage therethrough, while retaining the securing element 1026 effective that the securing element 1026 is attached to the adjustable implant device 1012. A passage element 1060 may be, for example, an eyelet, loop, hook, grommet, or other passage element 1060. An adjustable implant device 1012 may be configured for penetration by a securing element 1026 and have an outer portion 1062 and an inner portion 1064, where the outer portion 1062 is configured to accept passage of a securing element 1026 while remaining attached to inner portion 1064. An adjustable implant device 1012 may be configured for penetration by a securing element 1026 by being made of a suitable material, such as a soft or spongy material or composition able to be penetrated without minimal or localized breakage or tearing due to the penetration, and may be made of a resilient material that adheres or regains shape to closely adhere to penetrating material. For example, a soft rubber or plastic material that encloses or accompanies wire, fabric, plastic threads or fibers, or any suitable circumferential elements may be able to be penetrated yet maintain physical properties such as its shape and strength. In embodiments, an adjustable implant device 1012 may be configured for penetration by a securing element 1026 by having a coating of, or being enclosed by, cloth, fabric, mesh, netting, web, coils, threads, or other material or materials able to be penetrated by a securing element 1026 while retaining their hold or their enclosure of the adjustable implant device 1012. In embodiments, an adjustable implant device 1012 may have passages, or loops, or eyelets, or other elements configured to allow passage of a securing element 1026 and to allow the securing element 1026 to secure the adjustable implant device 1012 to tissue 1058.

As discussed above, an adjustable implant device 1012 may include a mesh, fabric, net, knit, woven, or other coating or outer layer. Such a coating or outer layer may be suitable for passage of a securing element 1026 effective that the securing element pass though the coating or outer layer and engage the adjustable implant device 1012 effective to secure the adjustable implant device 1012 to tissue when the securing device 1026 is engaged with tissue. Suitable materials for a coating or outer layer include, for example, e.g., polyethylene, polyester, polyethylene terephthalate, polyolefin, nylon, Dacron®, Teflon®, and other biocompatible materials, and may include biologically compatible fabric, biologically compatible mesh, biologically compatible knit, biologically compatible netting, or other materials or compositions. In embodiments, materials and coatings include materials and coatings that allow or enhance tissue overgrowth after placement of the device in a patient's body. In embodiments, materials and coatings include anti-thrombogenic materials and coatings that decrease risk of thrombosis after placement of the device in a patient's body.

In embodiments of adjustable implant devices 1012 having features of the invention, an adjustable implant device 1012 may have an outer polyester coating, such as an outer polyester sewing cuff, that allows easy tissue overgrowth after placement of the device in a patient's body. Underneath the outer polyester coating may be, for example, an optional silicone sheath or layer that provides purchase for the physician as the physician applies suture or as the securing elements 1026 are applied. In embodiments, a silicone sheath or layer may be made with a silicone that is adapted to allow a securing element 1026 to properly recover its original (curved) shape, such as a soft silicone. A soft silicone sheath or layer further provides the advantage of allowing greater flexure of the securing element 1026 within the adjustable implant device 1012. In further embodiments, there is no silicone sheath or layer.

FIGS. 41A-D are sequential illustrations of another method of securing an adjustable implant device 1012 to tissue 1058. As illustrated in these figures, in this method a securing element 1026 penetrates tissue 1058, and curves within tissue 1058, but does not penetrate an adjustable implant device 1012. Instead, a securing element 1026 curves around an adjustable implant device 1012, encircling and holding the adjustable implant device 1012 effective to secure it to the tissue 1058. A securing element 1026 having features of the invention as illustrated in FIGS. 41A-D curves around an adjustable implant device 1012 in order to secure the adjustable implant device 1012. Increasing amounts of advancement of the securing element 1026 out of housing 1024 lead to increasing amounts of curvature of the securing element 1026. As indicated in FIG. 41D, advancement of plunger 1049 may be effective to push securing element 1026 completely out of housing 1024 and to deploy securing element 1026, effective to secure the adjustable implant device 1012 to tissue 1058. It will be understood that either one, or both, of the methods illustrated in FIG. 40 and FIG. 41 may be used to secure an adjustable implant device 1012 to tissue 1058.

FIGS. 42A-I are a series of schematic partial cross-sectional illustrations showing deployment of a securing element 1026 from a housing 1024 to secure an adjustable implant device 1012 to tissue 1058. FIGS. 42A-I are similar to FIGS. 40A-G, in that these figures show penetration by a securing element 1026 of a portion of adjustable implant device 1012, advancement of the securing element 1026 into adjacent tissue 1058 with increasing amounts of curvature of the securing element 1026 within the tissue 1058 as it advances. Further advancement and further curvature leads to exit of tip portion 1052 from tissue surface 1072, and additional penetration of the adjustable implant device 1012, securing the adjustable implant device 1012 to tissue. However, FIGS. 42A-I include additional elements, including a housing retention device 1066. Housing retention device 1066 is illustrated in FIGS. 42A-I as an anchor-shaped hook, however it will be understood that any suitable retention device 1066 effective to maintain contact between implant holding element 1022 (e.g., housing 1024) and adjustable implant device 1012 during securing of the adjustable implant device 1012 to tissue 1058, yet to allow separation of holding element 1022 (e.g., housing 1024) from the adjustable implant device 1012 once the adjustable implant device 1012 has been secured to tissue 1058 may be used in the systems, devices and methods having features of the invention.

Figure 42A:
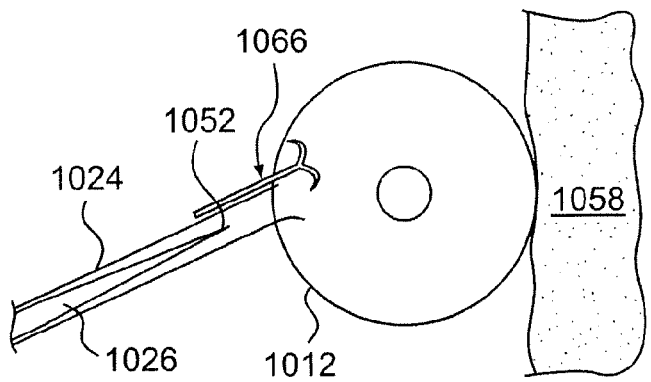
FIG. 42A-I are a series of schematic partial cross-sectional illustrations showing deployment of a securing element from a housing to secure an adjustable implant device to tissue, where
Figure 42B:
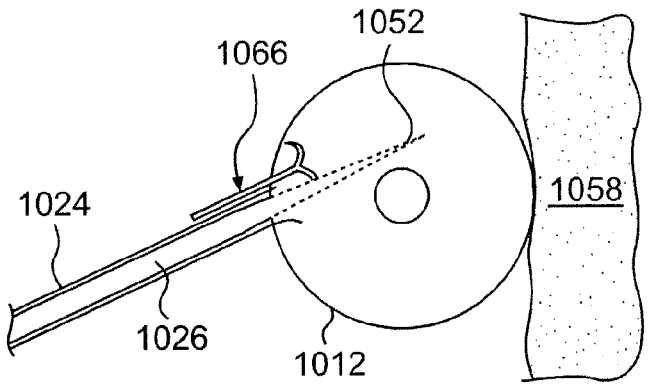
Figure 42C:
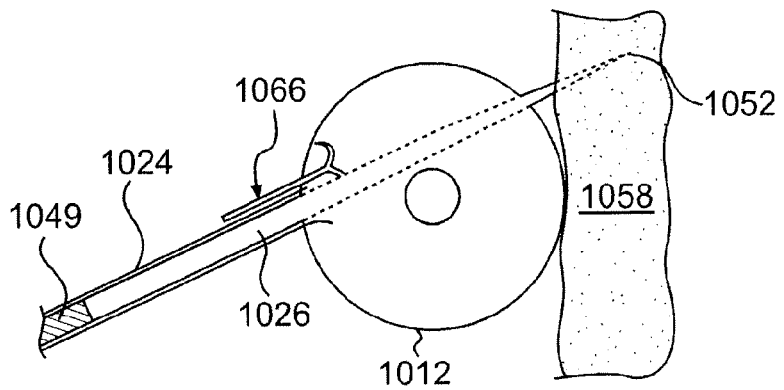
Figure 42D:
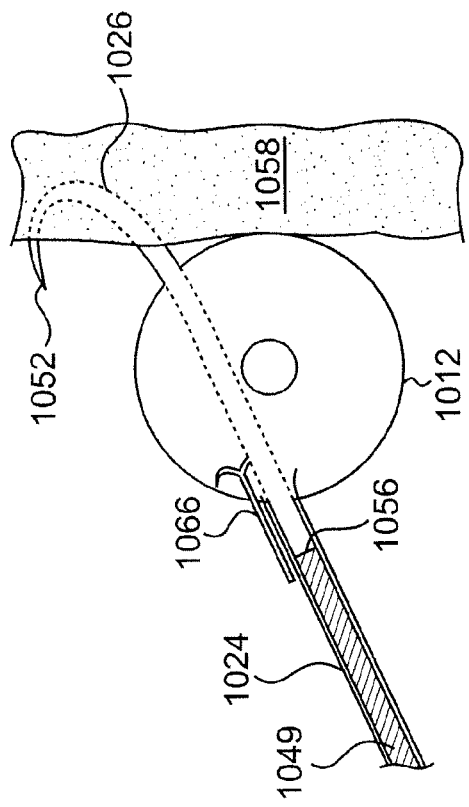
Figure 42E:
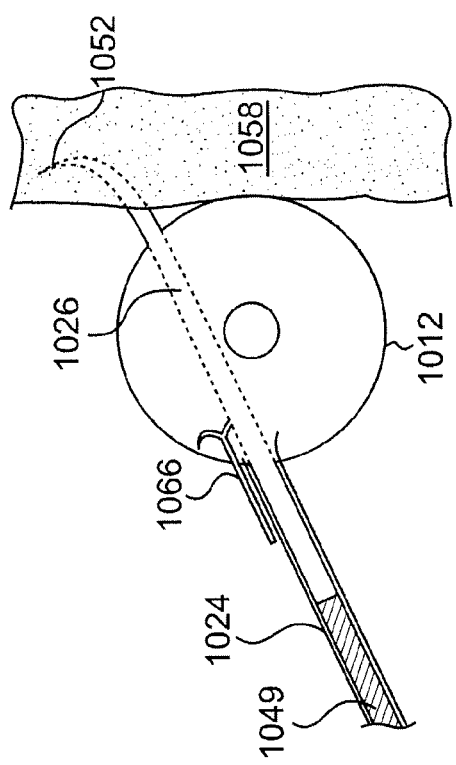
Figure 42G:
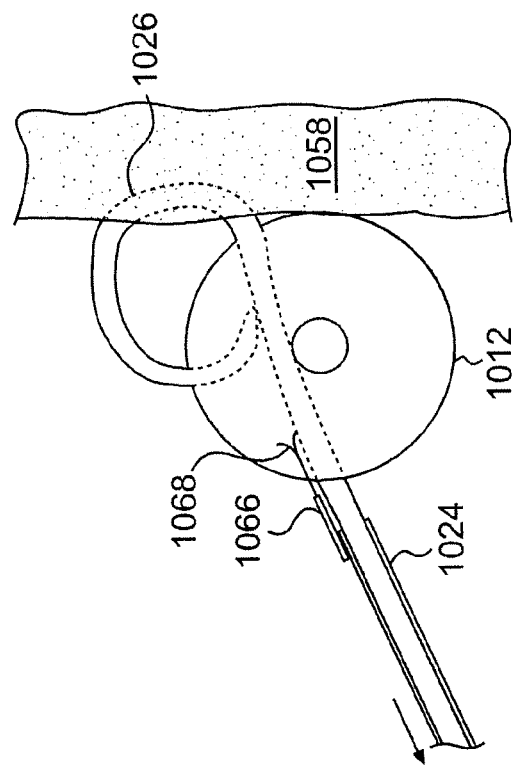
Figure 42F:
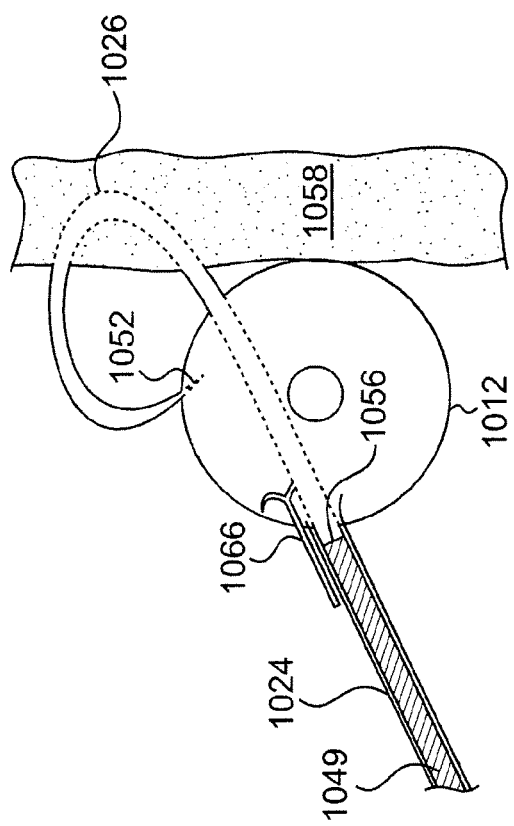
Figure 42H:
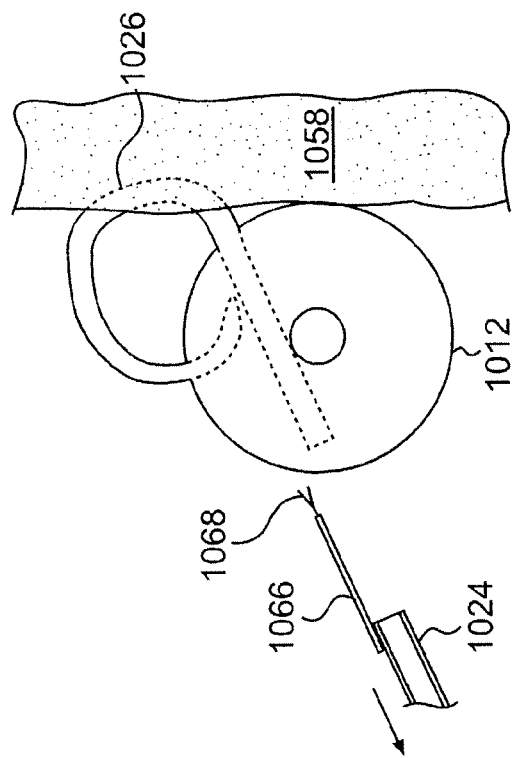
Figure 42I:
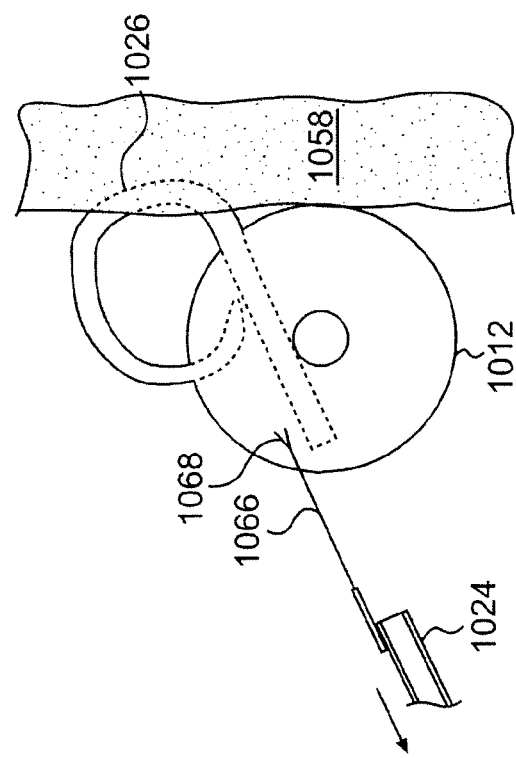

As shown in FIG. 42A an adjustable implant holding element 1022 (that is also a securing element housing 1024), having a securing element 1026 disposed within the housing 1024, may also have a retention element 1066 having grasping elements 1068 (shown here as retention element hooks 1068) which releasably secure the housing 1024 to the adjustable implant device 1012. FIGS. 42B and 42C show penetration of the implant device 1012 by the securing element 1026, and FIGS. 42D, E, and F show penetration of tissue 1058 by the securing element 1026, which curves as it advances, effective to secure the implant device 1012 to tissue 1058. As illustrated in FIG. 42F, securing element 1026 may curve sufficiently to exit tissue 1058 from the same tissue surface 1072 through which it initially entered tissue 1058, and re-connect with implant device 1012, strongly securing implant device 1012 to tissue 1058.

FIGS. 42 G, H, and I are sequential illustrations showing further steps in which the housing 1024 is retracted from the implant device 1012, the retention element 1066 deforming as the housing 1024 is retracted, allowing the housing 1024 to separate from the implant device 1012 effective to deploy the implant device 1012 and leave it secured to tissue 1058 by securing element 1026 and free of holding element 1022 (housing 1024). An operator may control such operations by hand, using handles 1036, or other control elements. For example, retraction of retention element hooks 1068 may be controlled by a manually operated handle. In further embodiments, retention element hooks 1068 are resilient, and deform and release under sufficient force; or may release upon rotation but not upon longitudinal stress; may be made with shape memory materials; may be magnetic; may be configured to release with heat, applied electricity, or other signal; or may be otherwise configured to maintain connection between an adjustable implant device 1012 and a holding element 1022.

Figure 43A:
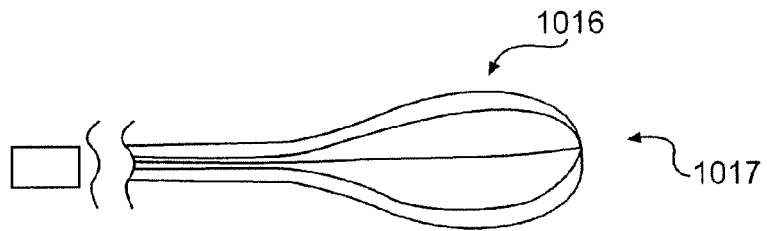
FIG. 43A is a partial schematic side-view of an implant device positioning element, shown in this illustration as a whisk of flexible wire-shaped material.
Figure 43B:
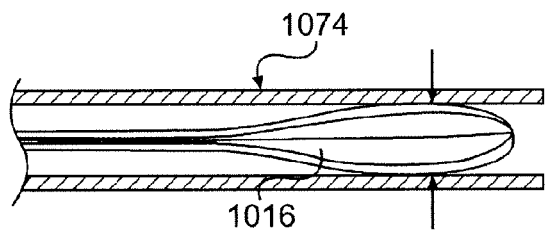
FIG. 43B is a partial schematic cross-sectional side view of a whisk embodiment of an implant device positioning element disposed within a trocar.
Figure 43C:
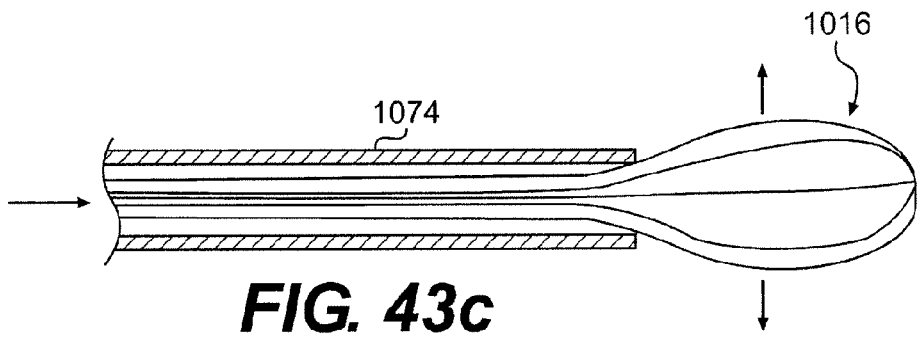
FIG. 43C is a partial schematic cross-sectional side view of a whisk embodiment of an implant device positioning element partially disposed within a trocar, and with a distal portion of the implant device positional element disposed outside the distal opening of the trocar, and has expanded radially to have a diameter equal to or greater than the diameter of the torcar.

FIGS. 43A-D provide a partial schematic side-view of an implant device positioning element 1016 and its use within a heart valve. As shown in these figures, an implant positioning device 1016 may be in the configuration of a whisk 1016. Such a whisk 1016 may be made up of several strands of flexible material, such as flexible wire-shaped material, including flexible metal wires, flexible plastic wires, flexible polymer wires, flexible carbon fiber wires, or other suitable materials. A schematic side view of portions of an exemplary whisk-shaped implant positioning device 1016 is shown in FIG. 43A with the distal portion 1017 in an expanded configuration. As indicated in FIG. 43B, a distal portion 1017 of an implant positioning device 1016 may also assume a contracted or compressed configuration. The implant positioning device 1016 shown in FIG. 43B is shown in cross-section disposed within a trocar 1074 suitable for delivery of an implant positioning device 1016 to a position near a target anatomical orifice or lumen, and near target tissue. The implant positioning device 1016 shown in FIG. 43B is shown in a contracted configuration. The implant positioning device 1016 shown in FIG. 43C is shown in an expanded configuration. The vertical arrows in FIG. 43C indicate radial expansion directions.

An implant positioning device 1016 may be resilient, and may expand upon exit from a trocar 1074 without further action or control. Thus, for example, an implant positioning element 1016 may expand from a contracted configuration assumed within a trocar 1074 to an expanded configuration (for the portion outside a trocar 1074) when advanced so that a distal portion 1017 as a result of the resiliency of the materials with which the implant positioning element 1016 is made. In embodiments, an implant positioning device 1016 may expand only under the control of an operator, or an automatic control mechanism. For example, an implant positioning device 1016 may be resilient, yet may include a stop or control effective to maintain the implant positioning device 1016 in a contracted configuration even when a portion or when all of an implant positioning device 1016 is disposed outside a trocar 1074 or other housing or delivery device. Alternatively, an adjustable implant device 1016 may be made of materials which would not normally expand into an expanded configuration after having been compressed or constrained, but may be configured with expansion mechanisms, such as gears, levers, springs, slides, or other mechanical, hydraulic, pneumatic, electric, magnetic, or other expansion elements. Upon release of such a stop, or activation of such a control, an implant positioning device 1016, or a distal portion of an implant positioning device 1017, may then assume an expanded configuration.

Thus, in embodiments of the systems, devices and methods having features of the invention, an implant positioning device 1016 may be made of a spring material, or other resilient material effective that it may collapse upon placement within a trocar 1074, but will rebound to expand to a larger diameter shape upon release from within the trocar 1074. In other embodiments, an implant positioning device 1016 may be made of any material, including non-resilient materials, that will allow it to be collapsed and place within a trocar 1074, and will allow it to be expanded to a larger diameter shape upon exit from within the trocar 1074, but such expansion may be achieved with the aid of external force or operation of additional tools or mechanisms, and need not be due to the resiliency of the material. For example, an implant positioning device 1016 may be operably connected to an adjustable implant device 1012, and its connection to the adjustable implant device 1012 may result in adjustment of the diameter of the positioning device 1016 in concert with, and due to, the adjustment of the diameter of the adjustable implant device 1012.

Figure 43D:
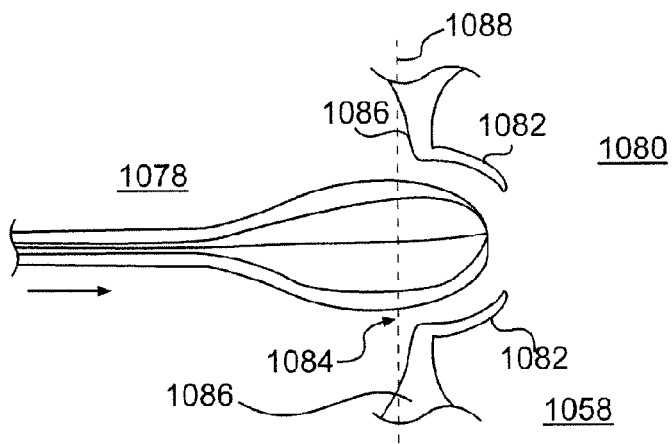
FIG. 43D is a partial schematic cross-sectional side view of a whisk embodiment of an implant device positioning element disposed within an anatomic orifice or lumen, illustrated here by a schematic representation of a cross-section of a human-mitral valve, and of portions of a left atrium and of a left ventricle adjacent the human mitral valve. The figure shown the mitral valve leaflets displaced by the implant device positioning element which has expanded to substantially fill the aperture of the valve effective to substantially center the device within the mitral valve. The implant device positioning element has sufficient open space to allow blood flow through the device and through the valve while the device is in place.

A schematic example of the operation of an implant positioning device 1016 is shown in a partial schematic cross-sectional side view in FIG. 43D. In that figure, a schematic representation of a cross-section of a human mitral valve 1076 is shown with portions of a left atrium 1078 and of a left ventricle 1080 adjacent the valve 1076. The tissue 1058 immediately adjacent the human mitral valve 1076 is the mitral valve annulus 1086, which defines a valve plane 1088 substantially perpendicular to the flow path of blood through the valve 1076. The figure shows the mitral valve leaflets 1082 displaced by the implant device positioning element 1016 which is shown with a distal portion 1017 disposed within the valve orifice 1084. The distal portion 1017 of the implant device positioning element 1016 has expanded to substantially fill the valve orifice 1084 effective to substantially center the implant device positioning element 1016 within the mitral valve 1076. Placement of a distal portion 1017 of an implant device positioning element 1016 within a valve 1076 is also effective to displace valve leaflets 1082 away from tissue 1058 so that valve leaflets 1082 will not be in the way, and will not be injured during placement and securing of an adjustable implant device 1012 to tissue 1058 adjacent a valve 1076. In addition, placement of a distal portion 1017 of an implant device positioning element 1016 within a valve 1076 and displacement of valve leaflets 1082 away from tissue 1058 also insures that valve leaflets 1082 will not be secured to tissue, or trapped by, an adjustable implant device 1012 due to securing an adjustable implant device 1012 to tissue 1058 adjacent a valve 1076. The implant device positioning element 1016 has sufficient open space to allow blood flow through the implant device positioning element 1016 and through the valve 1076 while the implant device positioning element 1016 is in place within a valve 1076.

In embodiments of the methods of using the systems and devices disclosed herein, an adjustable implant device 1012 may be mounted on, attached to, or otherwise carried with an implant positioning element 1016, as shown, for example, in FIG. 44A. In that figure, showing cross-sectional views, an implant device positioning element 1-16 is shown in the whisk embodiment, such as a whisk-shape made of flexible wire-shaped material, and carrying an adjustable implant device 1012. A similar view of these elements is provided in FIG. 44B, showing the implant device positioning element 1016 and the adjustable implant device 1012 disposed adjacent a human mitral valve 1076 within a left atrium 1078 (shown in schematic cross-sectional view). The left ventricle 1080 is shown at the right in FIGS. 44B and 44C. The implant device positioning element 1016 carrying the adjustable implant device 1012 is advanced towards the mitral valve 1076 (as indicated by the rightwardly pointing arrow) and into the valve 1076 as shown in FIG. 44C. The implant device positioning element 1016 seats within the orifice 1084 of the valve 1076, displacing leaflets 1082 and bringing the adjustable implant device 1012 into contact with tissue 1058 adjacent mitral valve 1076. In its expanded configuration, as shown in these figures, implant device positioning element 1016 centers within the valve 1076 and effectively guides the adjustable implant device 1012 into proper position around and adjacent the human mitral valve 1076 in contact with the mitral valve annulus 1086. Thus, the implant device positioning element 1016 is effective to direct the adjustable implant device 1012 into proper position in contact with the mitral valve annulus 1086, and to orient the adjustable implant device 1012 substantially along valve plane 1088 (which is substantially perpendicular to the path of blood flow through the valve 1076) for proper placement for attachment to the mitral valve annulus 1086 for repair or adjustment of a human mitral valve 1076. For example, such repair or adjustment of a human mitral valve 1076 may be accomplished by adjusting a dimension of an adjustable implant device 1012, such as a perimeter 1021 of the adjustable implant device 1012, effective to adjust a size or perimeter of the valve 1076 to effect a repair of the valve 1076.

Figure 45B:
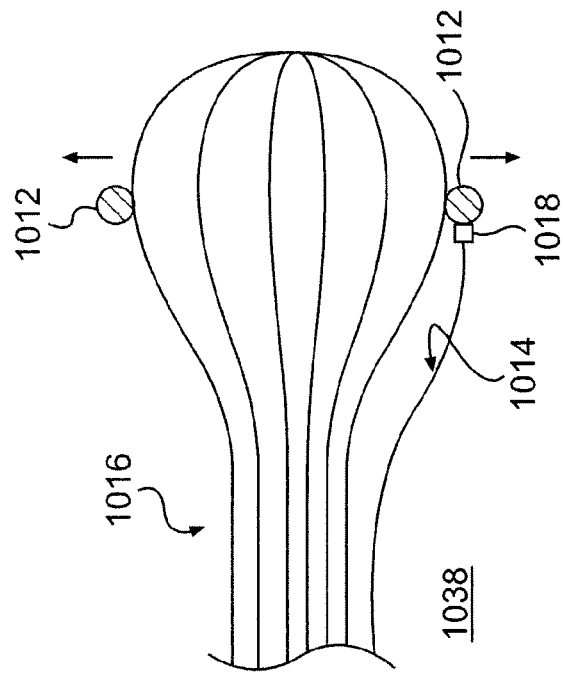
FIG. 45B is a schematic of a partial cross-sectional side view of the whisk, implant device and adjustment tool of FIG. 45A, showing operation of the tool and the resulting radial expansion of the adjustable implant device and of the whisk to assume expanded-diameter configurations.
Figure 45A:
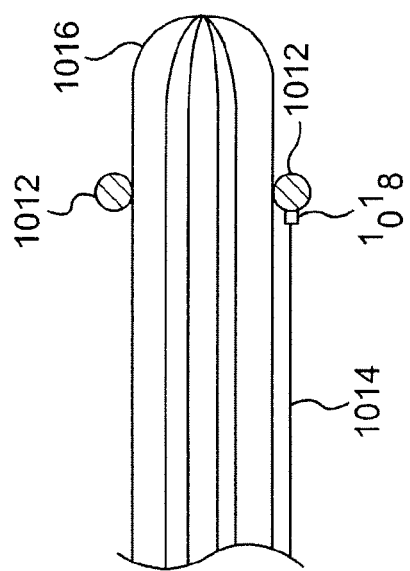
FIG. 45A is a partial schematic side-view of an implant device positioning element, shown as a whisk of flexible wire-shaped material, carrying an adjustable implant device having features of the invention and shown in schematic cross-sectional view, there being an adjustment tool operably attached to the adjustment member of the adjustable implant device. The adjustable implant device is illustrated in a reduced diameter configuration.

A similar sequence is presented in FIGS. 45A-45G, showing an adjustable implant device 1012, an implant device positioning element 1016 and a tool 1014 operably connected with an adjustment member 1018 via an adjustment coupler 1019. In FIG. 45A, an implant device positioning element 1016 is shown in partial schematic side-view, and shown as a whisk of flexible wire-shaped material, carrying an adjustable implant device 1012 having the invention and shown in schematic cross-sectional view. The tool 1014 is disposed in a non-planar configuration with respect to the adjustable implant device 1012. The adjustable implant device 1012 is illustrated in a reduced diameter configuration in FIG. 45A, and in an expanded diameter in FIG. 45B. The adjustable implant device 1012 is placed in its expanded configuration by action of the adjustment tool 1014 being operated (indicated by the curved arrow in FIG. 45B) to expand a perimeter 1021 of the adjustable implant device 1012. Expansion of the adjustable implant device 1012 is indicated by the vertical arrows in FIG. 45B. As the adjustable implant device 1012 expands, the implant positioning element 1016 may expand due to release of constraint, where the implant positioning element 1016 is resilient or otherwise under tension in a contracted configuration. In embodiments, the implant positioning element 1016 may expand by direct action of the expansion of the adjustable implant device 1012 where the implant positioning element 1016 is attached, fastened, or otherwise linked to the adjustable implant device 1012.

Placement of an adjustable implant device 1012 adjacent a mitral valve annulus 1086 with a system 1011 having features of the invention is shown in FIGS. 45C, D and E. FIG. 45C provides a schematic partial cross-sectional side view showing distal portions of an implant device positioning element 1016 carrying an adjustable implant device 1012 and having an adjustment tool 1014 operably connected to the adjustable implant device 1012 via adjustment member 1018 and adjustment tool coupler 1019. Mitral valve 1076, mitral valve annulus 1086, and leaflets 1082 are shown in these figures. As the assembly including an implant device positioning element 1016, adjustable implant device 1012 and adjustment tool 1014 approaches the mitral valve annulus 1086, the adjustable implant device 1012 (which substantially defines a plane) is disposed in an orientation with its plane substantially coplanar with the mitral valve annulus 1086, and the tool 1014 is disposed in an orientation in which its longitudinal axis is substantially non-planar with the plane of the mitral valve annulus 1086 and with the plane of the adjustable implant device 1012.

The assembly including an implant device positioning element 1016, adjustable implant device 1012 and adjustment tool 1014 is shown in FIG. 45C with the implant device positioning element 1016 in a contracted configuration within a left atrium 1078. Operation of adjustment tool 1014, as indicated by the curved arrow in FIG. 45D, expands adjustable implant device 1012 and expands (or allows expansion of) implant device positioning element 1016. Expanded adjustable implant device 1012 better approximates the proper size for placement on mitral valve annulus 1086. Advancement of assembly that includes implant device positioning element 1016, adjustable implant device 1012 and adjustment tool 1014, with the adjustable implant device 1012 and implant device positioning element 1016 in expanded configurations, as shown in FIG. 45E, displaces leaflets 1082 and places adjustable implant device 1012 in position in contact with mitral valve annulus 1086 and ready for securing to the annulus 1086. As is shown in these figures, implant device positioning element 1016 is effective to properly position an adjustable implant device 1012, by properly centering the device so that it does not overlap the valve orifice 1084 (occupied by the implant positioning element 1016) and is in contact with the valve annulus 1086. Blood flow is not blocked by these devices and methods, and damage or improper placement of valve leaflets 1082 is also avoided using these devices and methods.

An adjustable implant device having features of the invention may include an adjustable perimeter or shape, and a perimeter or shape adjustment mechanism that is operably connected with a docking element. A docking element may be configured to operably engage an adjustment tool. An adjustment tool may be configured to operate with the docking element effective to adjust a perimeter or shape of the adjustable implant device.

Figure 46A:
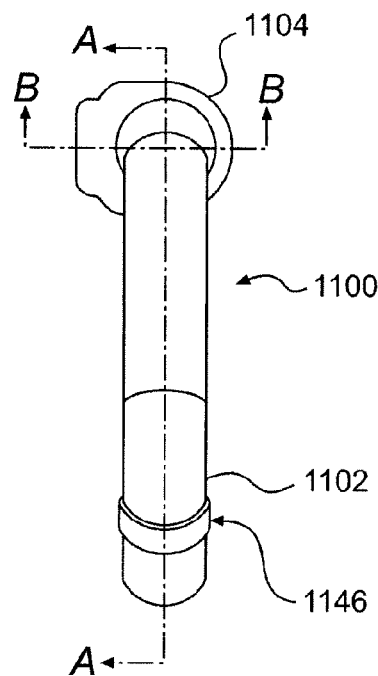
FIG. 46A provides a schematic side view of an adjustable implant device having features of the invention.
Figure 46B:
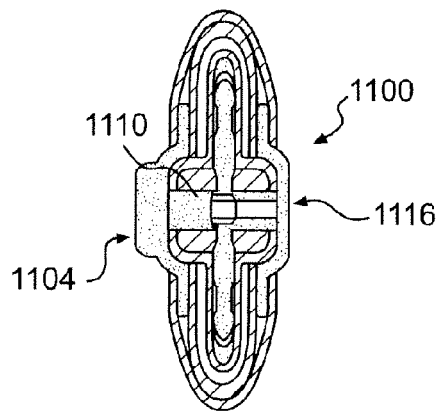
FIG. 46B provides a cross-sectional view of the adjustable implant device having features of the invention of FIG. 46A, the cross-section being taken along a plane parallel to a longitudinal axis of a cylinder oriented to pass through the inner space defined by the ring of the implant device (the line of cross-section shown was line BB in FIG. 46A).

An adjustable implant device having features of the invention is shown in FIGS. 46A, 46B and 46 C. These figures provide three related views of an implant device having features of the invention: a schematic side view of such a device (FIG. 46A), a cross-section through the device crossing the docking element and adjustment mechanism, along a plane parallel to a longitudinal axis of a cylinder oriented to pass through the inner space defined by the ring of the implant device (FIG. 46B); and a cross-sectional view taken along a plane through the device in a plane perpendicular to a longitudinal axis of a cylinder oriented to pass through the inner space defined by the ring of the implant device (FIG. 46C). The plane of the cross-section illustrated in FIG. 46C is parallel to a plane of tissue that would be found when the device was in place on a heart valve annulus.

Figure 46C:
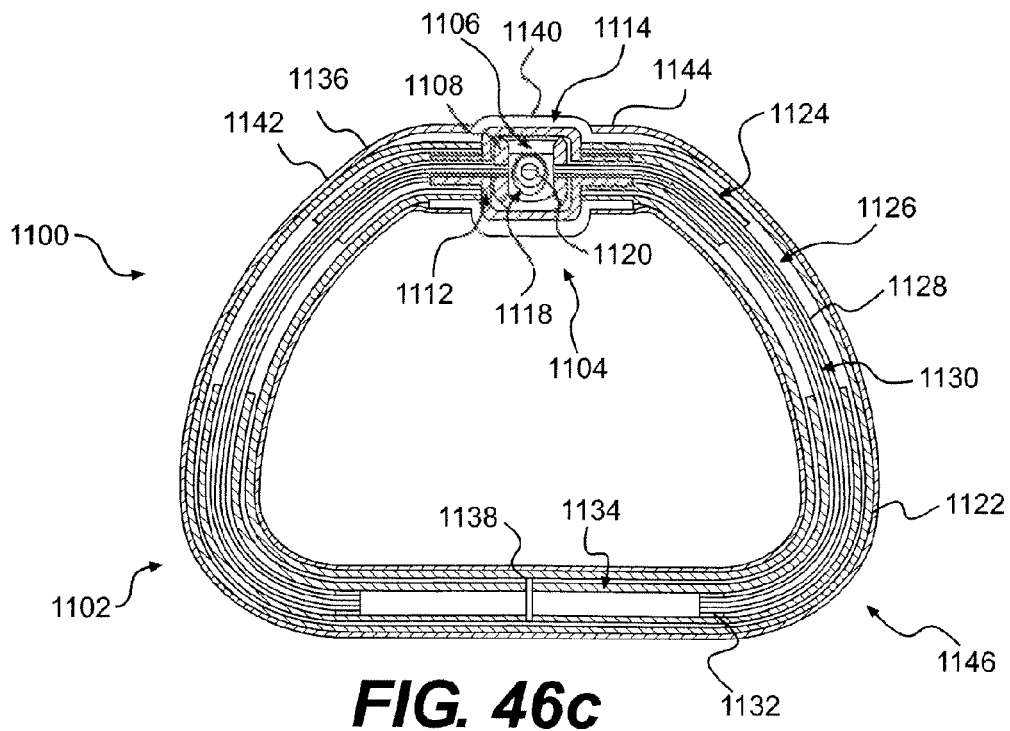
FIG. 46C provides a cross-sectional view taken along a plane through the device in a plane perpendicular to a longitudinal axis of a cylinder oriented to pass through the inner space defined by the ring of the implant device (the line of cross-section shown as line CC in FIG. 46A).

As shown in FIG. 46A, an implant device 1100 having features of the invention includes an annular body 1102 and an adjustment mechanism 1104. An annular body 1104 may have a substantially circular shape, or an oval shape, or a rounded trapezoidal shape (as illustrated, for example, in FIG. 46C), or any suitable shape. Such a suitable shape may be a closed curve, as illustrated in FIG. 46C, or may be an open curve.

It will be understood that, in embodiments, a suitable shape may be an open shape, in which an annular body 1102 has an elongated body portion having two free ends. In embodiments having an annular body 1102 having two free ends, an elongated body portion may be curved, and the free ends may be disposed near to each other. In embodiments having a curved annular body 1102 having two free ends disposed near to each other, the device 1100 may be configured to adjust the distance between the free ends (e.g., a ribbon or thread of material may connect the free ends, and may be configured to draw the free ends towards each other).

Figure 46D:
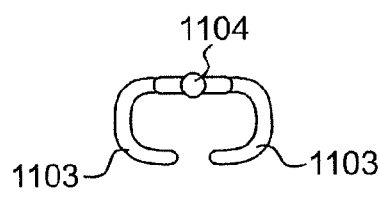
FIG. 46D provides a schematic view of a an alternative embodiment of a adjustable implant device having features of the invention that does not form a closed loop.

For example, as illustrated in FIG. 46D, an annular body 1102 of an adjustable implant device 1100 having features of the invention may not form a closed loop, but may instead be configured with two free ends 1103 instead of forming a continuous, closed loop structure. The configuration of such a device, including the closeness and angle of approach of the two free ends 1103 to each other, may be adjusted and controlled and serve to adjust a size and/or a shape of an adjustable implant device 1100 and to adjust a size and/or a shape of an anatomical orifice or lumen to which such an adjustable implant device 1100 is attached. An adjustment mechanism 1104 may be used to make such adjustments in a size and/or a shape of an adjustable implant device 1100. For example, an adjustment mechanism 1104 may be operably connected with internal guides, cables, slides, wires, and/or other elements effective to adjust the position, orientation, and placement of an end 1103 or of both ends 1103, and of other portions or elements of an annulur body 1102 and of an adjustable plant device 1100 as a whole.

Figure 46E:
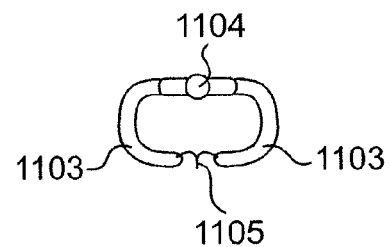
FIG. 46E provides a schematic view of a an alternative embodiment of a adjustable implant device having features of the invention that does not form a closed loop having ends connected by a flexible element, illustrated here by a thread.

As illustrated in FIG. 46E, such free ends 1103 may be connected by a connecting element 1105. Such a connecting element 1105 may be, for example, a thread, suture, ribbon, cable, filament, wire, braided wire, bar, threaded bar, or other element. The connecting element 1105 is illustrated in FIG. 46D as a thread. In embodiments having features of the invention, the connecting element 1105 may be very flexible, may be somewhat flexible, may be barely flexible, and may be substantially inflexible. An adjustment mechanism 1104 may be used to make such adjustments in a size and/or a shape of an adjustable implant device 1100. For example, an adjustment mechanism 1104 may be operably connected with such a thread effective to adjust the position, orientation, and placement of an end 1103 or of both ends 1103 and of other portions or elements of an annulur body 1102 and of an adjustable plant device 1100 as a whole.

Figure 46F:
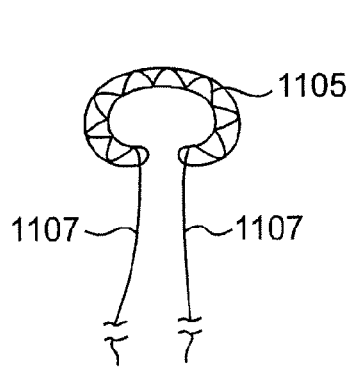
FIG. 46F provides a schematic view of a an alternative embodiment of a adjustable implant device having features of the invention that does not form a closed loop, and has an elongated flexible element (shown here as a thread) that, in two places, extends away from the body of the adjustable implant device.

An illustration of a further embodiment of an adjustable implant device 1100 having features of the invention is shown in FIG. 46F. An adjustable implant device 1100 having features of the invention that does not form a closed loop, and having free ends 1103, may have an elongated connecting element 1105 that extends away from the adjustable implant device 1100 in two places. One or both of the ends 1107 may be suitable for manipulation by an operator, such as a surgeon. For example, pulling on an elongated connecting element 1105 configured as illustrated in FIG. 46F may pull on connected portions of the elongated connecting element 1105, effective to contract a portion of, or structure on or within, a portion of annular body 1102 of an adjustable implant device 1100, and may alter a size and/or shape of the adjustable implant device 1100.

Figure 46G:
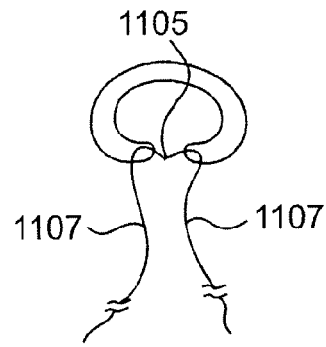
FIG. 46G provides a schematic view of a an alternative embodiment of a adjustable implant device having features of the invention that does not form a closed loop, having two ends connected by a flexible element (shown here as a ribbon), the flexible element connecting the two free ends of the body of the adjustable implant device.

In further embodiments, as illustrated, for example, in FIG. 46G, an adjustable implant device 1100 having features of the invention and having two free ends 1103 may have free ends 1103 connected to each other by a connecting element 1105. The connecting element 1105 may itself have ends 1107 which extend away from the adjustable implant device 1100. One or both of the ends 1107 may be suitable for manipulation by an operator, such as a surgeon. For example, pulling on an elongated connecting element 1105 configured as illustrated in FIG. 46G may be effective to draw ends 1107 closer together, and so to alter a size and/or shape of the adjustable implant device 1100.

Figure 46H:
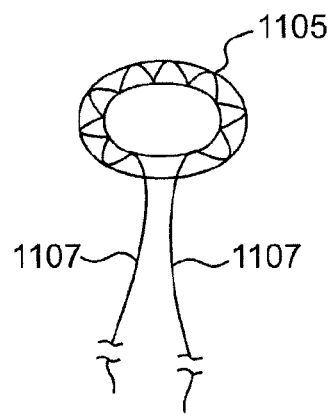
FIG. 46H provides a schematic view of a an alternative embodiment of a adjustable implant device having features of the invention that does not form a closed loop, and has an elongated flexible element (shown here as a thread) that, in two places, extends away from the body of the adjustable implant device.

FIG. 46H provides a schematic view of an embodiment of an adjustable implant device having features of the invention that does form a closed loop, and that has an elongated connecting element 1105 (shown here as a thread) that, in two places, extends away from the body of the adjustable implant device. One or both of the ends 1107 may be suitable for manipulation by an operator, such as a surgeon. For example, pulling on an elongated connecting element 1105 configured as illustrated in FIG. 46H may pull on connected portions of the elongated connecting element 1105, effective to contract a portion of, or structure on or within, a portion of annular body 1102 of an adjustable implant device 1100, and may alter a size and/or shape of the adjustable implant device 1100.

Figure 46I:
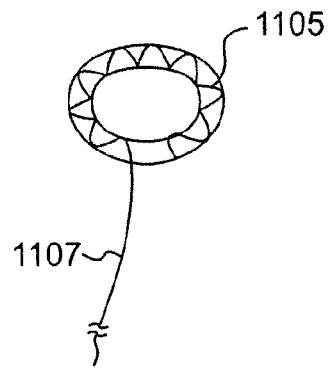
FIG. 46I provides a schematic view of a an alternative embodiment of a adjustable implant device having features of the invention that does not form a closed loop and has an elongated flexible element (shown here as a thread) that, in one place, extends away from the body of the adjustable implant device.

FIG. 46I provides a schematic view of an embodiment of an adjustable implant device having features of the invention that does form a closed loop, and that has an elongated connecting element 1105 (shown here as a thread) that, in one place, extends away from the body of the adjustable implant device. Such an end 1107 may be suitable for manipulation by an operator, such as a surgeon. For example, pulling on the elongated connecting element 1105 configured as illustrated in FIG. 46I may pull on connected portions of the elongated connecting element 1105, effective to contract a portion of, or structure on or within, a portion of annular body 1102 of an adjustable implant device 1100, and may alter a size and/or shape of the adjustable implant device 1100.

An adjustable implant device having features of the invention may include an adjustable perimeter or shape, and a perimeter or shape adjustment mechanism that is operably connected with a docking element. A docking element may be configured to operably engage an adjustment tool. An adjustment tool may be configured to operate with the docking element effective to adjust a perimeter or shape of the adjustable implant device.

Although discussed with respect to devices 1100 having an annular body 1102 that is a closed annular body 1102, elements of a device 1100 discussed herein may be similar and may operate in similar ways for devices 1100 that have open annular bodies 1102 and for devices 1100 that have closed annular bodies 1102. Thus, although the following discussion is with respect to FIGS. 46A, 46B, and 46C which show an implant device 1100 having a closed annular body 1102, it will be understood that the discussion also relates to an implant device 1100 having an open annular body 1102.

A device 1100 has an adjustment mechanism 1104 that includes a drive gear 1106 that is operably engaged with a driven gear 1108 or gears 1108. Rotation of drive gear 1106 is effective to rotate a driven gear 1108. In the embodiment shown in FIGS. 46B and 46C, a single drive gear 1106 engages two driven gears 1108 effective to adjust a size and/or shape of the device 1100. As illustrated in FIGS. 46B and 46C, gears 1106 and 1108 may be beveled gears, and may be, for example, worm gears or other gears configured to engage each other with non-parallel axes of rotation. FIG. 46C shows top thrust bushing 1110, against which drive gear 1106 may push, and also shows side thrust bushings 1112 in contact with driven gears 1108. Gear 1106 and gears 1108 are shown disposed within a housing formed from a top gear housing 1114 and a bottom gear housing 1116. Gear 1106 rotates around pin 1118 within the housing. A pin 1118 may be held in place by, for example, a threaded insert 1120. It will be understood that a drive gear 1106 is configured to engage with an adjustment tool, such as an adjustment tool 1014 as illustrated in FIG. 45, or other adjustment tool having features of the invention. Operation of such an adjustment tool is effective to initiate and control the movement of a drive gear 1106 effective to drive driven gears 1108 and to adjust a size and/or shape of a device 1100.

Several components are disposed inside the annular body 1102 of the device 1100. For example, threaded spars 1122 help to provide form and support to the annular body 1102, and (as described in more detail below) help couple rotary motion of the gears 1108 to a change in size and/or shape of the device 1100. Gearbox sleeves 1124 also help to provide form and support to the annular body 1102, and provide strength and stability to the interface between the annular ring 1102 and the adjustment mechanism 1104 of the device 1100.

Guide tube coil 1126 within annular body 1102 contains at least two elements, the outer drive coil 1128 and the inner drive coil 1130, which translate rotation of the driven gears 1108 into rotation of the screws 1132 within threaded spars 1124. Rotation of the screws 1132 causes movement of the sleeve screws 1132 within the threaded spars 1124 and spar sleeves 1134, changing a size and/or shape of the annular body 1102. For example, rotation of the screws 1132 causing axial movement of screws 1132 within threaded spars 1124 and spar sleeves 1134 effective that screws 1132 come closer to each other within spar sleeves 1134 will cause the perimeter of annular body 1102 to shrink, so as to change the shape and size of the annular body 1102 effective that the annular body 1102 has a smaller internal bore 1135. In a further example, rotation of the screws 1132 causing axial movement of screws 1132 within threaded spars 1124 and spar sleeves 1134 effective that screws 1132 become farther away from each other within spar sleeves 1134 will cause the perimeter of annular body 1102 to enlarge, so as to change the shape and size of the annular body 1102 effective that the annular body 1102 has a larger internal bore 1135.

A sheath 1136, which may comprise, for example, a silicone tube, encloses internal elements of an annular body 1102. For example, as shown in FIGS. 46B and 46C, a sheath 1136 may enclose a gearbox sleeve 1124; a coil guide 1126 and outer and inner drive cQils 1128 and 1130 within the coil guide 1126; threaded spars 1122 and sleeves 1134; and may enclose other elements. For example, a stop screw 1138 configured to prevent excessive interaction between screws 1132 if screws 1132 are moved to the ends of their travel within threaded spars 1122 and sleeves 1134 may also be disposed within a sheath 1136.

A seal jacket 1140 may join with sheath 1136 to form an enclosure 1141. An enclosure 1141 comprising a seal jacket 1140 joined with a sheath 1136 may enclose an adjustment mechanism 1104, including elements of the adjustment mechanism gears 1106 and 1108, pin 1118 and threaded insert 1120; bushings 1110 and 1112; top housing 1114 and bottom housing 1116; and may enclose other elements. Seal jacket 1140 together with sheath 1136 may enclose many or all of the working elements required for adjusting a size and/or a shape of a device 1100 having features of the invention. In embodiments, further elements may be disposed, at least in part, on, around, or otherwise outside an enclosure formed by a seal jacket 1140 joined with sheath 1136.

For example, a sewing cuff 1142 may be disposed around an enclosure 1141 effective to provide material to which sutures or other securing agents may be attached to a device 1100 having features of the invention to enable or aid in the attachment of the device 1100 to tissue. In embodiments, a sewing cuff 1142 surrounds the entire enclosure 1141. However, a sewing cuff 1142 may enclose only a portion of a device 1100; for example, a sewing cuff 1142 may enclose only a sheath 1136, or may only enclose a seal jacket 1140. In alternative embodiments, a sewing cuff 1142 surrounds only a portion of a sheath 1136 or surrounds only a portion of a seal jacket 1140.

Similarly, a suture cuff 1144 may be disposed on or around a device 1100 having features of the invention. As shown in FIG. 46C, a suture cuff 1144 may be disposed on a surface of a device 1100 effective to provide a location suitable for receiving a suture and for securing the device 1100 to tissue. In embodiments, a suture cuff 1144 may surround a portion of the adjustment device 1104; or may surround all of, or a portion of the sheath 1136; or may surround all of, or a portion of, a seal jacket 1140; or may surround all of, or a portion of, the entire enclosure 1141. However, a sewing cuff 1142 may enclose only a portion of a device 1100; for example, a sewing cuff 1142 may enclose only a sheath 1136, or may only enclose a seal jacket 1140. In alternative embodiments, a sewing cuff 1142 may surround only a portion of a sheath 1136 or may surround only a portion of a seal jacket 1140.

A sewing cuff 1142 and/or a suture cuff 1144 may be made with a material having properties suitable for receiving and retaining sewing materials, such as a needle, thread, suture, cord, wire, or other material suitable for engaging and retaining a device 1100 to tissue. For example, such materials may include woven materials including fabrics, cloth, woven polymer, woven metal, and other woven materials; mesh, including metal mesh, polymer mesh, fabric mesh, and other mesh; netting, including metal netting, polymer netting, fabric netting, and other netting; and other materials through which a needle or other guide may pass, yet which are strong enough to retain elements which pass through these materials. A sewing cuff 1142 and/or a suture cuff 1144 may include elements such as, for example, rings, loops, hoops, coils, and other shapes useful for engaging and retaining elements which pass through such rings, loops, hoops, coils, and other shapes.

As shown in FIGS. 46A and 46C, an implant device 1100 may include a marker 1146. A marker 1146 may be configured to aid an operator, such as a surgeon, in properly orienting an implant device 1100 during placement of the device. A marker 1146 may be configured to aid an operator, such as a surgeon, in properly orienting a suture, clip, or other securing device or securing aid, during placement and/or securing of the device 1100 at a desired location adjacent tissue. In embodiments, a marker 1146 may be disposed on an outside surface of a device 1100, as shown in FIGS. 46A and 46C. In embodiments, a device 1100 may carry multiple markers 1146.

A marker 1146 may be perceptible to the unaided eye in normal light, and may be perceptible by a human observer with technical aid. A marker 1146 may be detectable by other means than by observation by a human observer. For example, a marker 1146 may be perceptible or identifiable with the aid of particular illumination or of a visualization device. Particular illumination may aid the visualization of a marker 1146 where, for example, such illumination includes ultraviolet radiation, and the marker 1146 is configured to reflect or emit visible light during or following illumination by ultraviolet light. Particular illumination and visualization devices may aid the visualization of a marker 1146 where, for example, the marker is radio-opaque, and the marker is subjected to illumination by radiation (e.g., by X-rays) effective that an image may be obtained showing the approximate location of the device 1100.

A marker 1146 may be disposed on an outside surface of a device 1100, as shown in FIGS. 46A and 46C. In embodiments, a marker 1146 may be disposed within a device 1100. A marker 1146 disposed within a device 1100 may be detected, for example, where penetrating illumination such as X-ray illumination is used to aid in detection or visualization of the marker. In embodiments, some or all of markers 1146 carried by a device 1100 may be disposed on an outer surface of a device 1100, and some or all of such markers 1146 may be disposed within a device 1100.

Figure 47A:
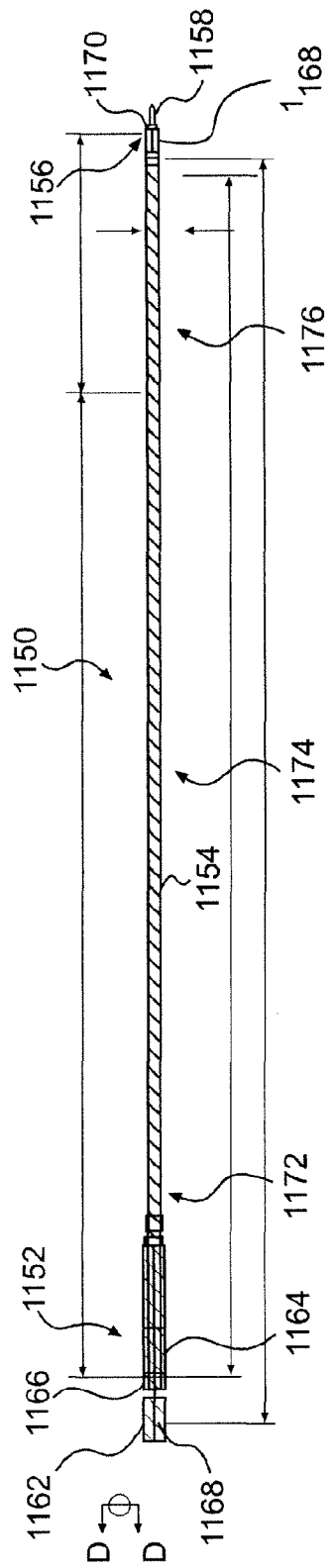
FIG. 47A provides a side schematic view of a adjustment tool having features of the invention.
Figure 47C:
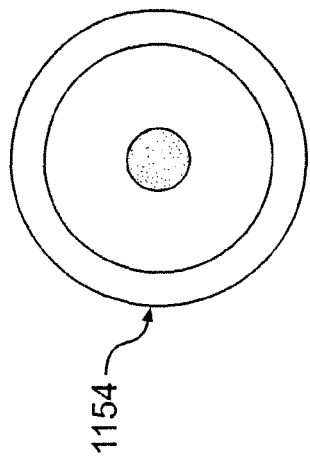
FIG. 47C provides an end-on schematic view of a proximal portion of an adjustment tool having features of the invention.
Figure 47B:
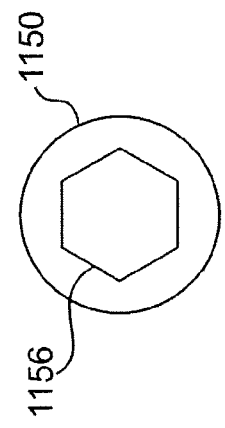
FIG. 47B provides a face-on schematic view of a distal portion of an adjustment tool having features of the invention.
Figure 47D:
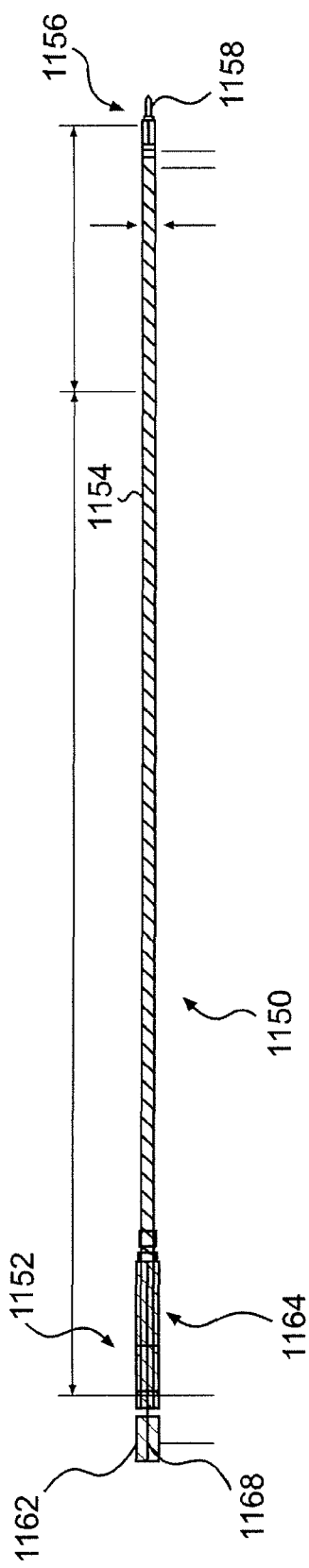
FIG. 47D provides a side cross-sectional view of an adjustment tool having features of the invention, taken through the device along a plane passing through a longitudinal axis of the adjustment tool (line DD shown in FIG. 47A).

FIG. 47A provides a side schematic view of an adjustment tool 1150 having features of the invention, showing, for example, a handle portion 1152, a shaft portion 1154, and a distal tip portion 1156 having an engagement element 1158 configured to operably engage an adjustment mechanism such as an adjustment mechanism 1104 illustrated in FIGS. 46A, B and C. FIG. 47B provides a face-on schematic view of distal tip portion 1156 of the adjustment tool 1150 shown in FIG. 47A. FIG. 47C provides an end-on schematic view of the handle portion 1154 of the adjustment tool 1150 shown in FIG. 47A. FIG. 47D provides a side cross-sectional view of the adjustment tool 1150, the cross-section being taken along a plane passing through a longitudinal axis 1160 of the adjustment tool 1150 (the cross-section taken along line DD shown in FIG. 47A). A handle portion 1152 may have more than one portion. As indicated in FIGS. 47A and 47D, a handle portion 1152 may include a proximal handle portion 1162 and a distal handle portion 1164. Different handle portions may move (e.g., may rotate) independently of the other portion(s). However, in embodiments of the adjustment tools 1150 having features of the invention, different handle portions may be configured to move together, or to be constrained in their movements, or to be restrained from moving, relative to each other. For example, an adjustment tool 1150 having features of the invention may include a stop 1166 or other element configured to brake the movement of one handle portion with respect to another handle portion.

As illustrated in the embodiment shown in FIGS. 47A, B, and C, distal handle portion 1164 may be fixedly attached to shaft 1154, so that rotation of distal handle portion 1164 rotates shaft 1154. In embodiments, such as the embodiment illustrated in FIGS. 47A, B, and C, rotation of inner axle 1168 rotates distal tip portion 1156 and rotates engagement element 1158. Thus, an operator may hold or manipulate distal handle portion 1164 to control the position and orientation of an adjustment tool 1150, and may also rotate, if desired, proximal handle portion 1162 effective to control the position and/or orientation of distal tip portion 1156 and of engagement element 1158.

As shown in the embodiment shown in FIGS. 47A, B, and C, a proximal handle portion 1162 may be configured to be able to rotate with respect to distal handle portion 1164, so that rotation of proximal handle portion 1162 does not cause rotation of shaft 1154. However, proximal handle portion 1162 may be attached to an inner axle 1168 effective that rotation of proximal handle portion 1162 causes rotation of inner axle 1168 while not significantly affecting shaft 1154. This allows operation of an adjustment tool 1150 without damage to tissue that might be caused by rotation of a shaft, and provides for control and guidance of an adjustment tool 1150, e.g., by gripping or guiding a shaft 1154, while allowing rotation of inner axle 1168 at the same time. Thus, providing a shaft 1154 having a rotatable inner axle 1168 (and handle portions 1162 and 1164 for controlling a shaft 1154 and a rotatable inner axle 1168) allows for stable operation of an adjustment tool 1150 and minimizes the possibility of tissue damage.

An engagement element 1158 may be secured to an inner axle 1168 by a connector 1170, which may be, for example, a threaded connector 1170, and/or may comprise a glue or a weld to secure an engagement element 1158 to an inner axle 1168. As mentioned above, rotation of inner axle 1168 rotates distal tip portion 1156 and engagement element 1158. For example, rotation of inner axle 1168 rotates distal tip portion 1156 having an engagement element 1158 configured to operably engage an adjustment mechanism such as an adjustment mechanism 1104 illustrated in FIGS. 46A, B and C. However, when desired, stop 1166 may be engaged effective to lock a handle portion 1162 to a handle portion 1164 so that proximal handle portion 1162 does not rotate with respect to handle portion 1164. For example, during placement of an adjustment tool 1150, it may be desirable that proximal handle portion 1162 not rotate with respect to handle portion 1164, or that distal tip portion 1156 not rotate with respect to shaft 1154. Once an adjustment tool 1150 is in place, with distal tip 1156 in correct position with respect to an adjustment mechanism 1104, and engagement element 1158 engaged with elements of an adjustment mechanism 1104, e.g., effective to operate a drive gear 1106, a stop 1166 may be disengaged to allow free rotation of distal tip portion 1156 and engagement element 1158 with respect to shaft 1154.

A shaft 1154 may be made from materials in such a way that the physical properties of the shaft may vary along its length. For example, a shaft 1154 may be configured to be stiffer at one end as compared to the other end; to be more flexible in a region or location, as compared with other regions or locations along the shaft 1154; or to have other varying physical properties. In embodiments, a shaft 1154 may have a proximal shaft portion 1172, a medial shaft portion 1174, and a distal shaft portion 1176. Shaft portions 1172, 1174, and 1176 may have different physical properties, and may be configured to provide, for example, a shaft 1154 that is flexible; a shaft 1154 that is strong; a shaft 1154 that is sterilizable; a shaft 1154 that is resistant to corrosion; a shaft 1154 that has shape memory properties; a shaft 1154 that may be bent, and retain the bent shape; a shaft 1154 that may be bent, retain the bent shape, and allow rotation of an engagement element at a distal portion of the shaft 1154; or combinations of some or all of these and other properties.

For example, a shaft 1154 may be made of a single material, compound or composite, or may be made with different components operably joined together. A shaft 1154 may be flexible, and may include curves, bends, or other shapes, while still allowing rotation of an inner axle 1168. A shaft 1154 and an inner axle 1168 may be made with, for example, e.g., a metal, such as, e.g., stainless steel; a plastic, such as, for example; a polymer, such as, e.g., polyethylene, polycarbonate, polyurethane, or other polymer; a polyether block amide (PEbax); metal tube or tubes; an alloy, such as, e.g., a nickel titanium alloy such as nitinol; an organic fiber, such as carbon fiber; metal or carbon fiber braid; a polymer including metal or carbon fiber braid; or other material or combinations and mixtures of materials.

In such embodiments, where a proximal portion 1172 comprises high density polyethylene (HDPE), a medial portion 1174 comprises composite PEbax with stainless steel braid, and a distal portion 1176 comprises composite PEbax with stainless steel braid, the distal portion 1176 having less dense PEbax than the medial portion 1174, the shaft 1154 is flexible yet strong, and can be bent or curved during use without breaking and without destroying its ability to guide and rotate inner axle 1168 effective to operably control an adjustment mechanism 1104, such as to rotate a drive gear 1106 effective to change a size and/or shape of an adjustable implant device having features of the invention (e.g., an adjustable implant device 1100).

In embodiments of adjustment tools 1150 having features of the invention, a proximal shaft portion 1172 may be made with HDPE tubing; and a medial shaft portion 1174 and a distal shaft portion 1176 may be made with a composite material comprising Polyether block amide (PEbax) and stainless steel braid. In embodiments, medial shaft portion 1174 may be made with a composite material comprising 72D PEbax and 0.002 inch stainless steel braid. In embodiments, distal shaft portion 1176 may be made with a composite material comprising 55D PEbax and 0.002 inch stainless steel braid. In such embodiments, where a proximal portion 1172 comprises HDPE, a medial portion 1174 comprises composite PEbax with stainless steel braid, and a distal portion 1176 comprises composite PEbax with stainless steel braid, the distal portion 1176 having less dense PEbax than the medial portion 1174, the shaft 1154 is flexible yet strong, and can be bent or curved during use without breaking and without destroying its ability to guide and rotate inner axle 1168 effective to operably control an adjustment mechanism 1104, such as to rotate a drive gear 1106 effective to change a size and/or shape of an adjustable implant device having features of the invention (e.g., an adjustable implant device 1100).

Thus, the methods, devices and systems disclosed herein provide advantages over the prior art, and provide means for repair and adjustment of anatomical orifices and lumens, such as a mitral valve, that are needed in the art. It will be understood that features disclosed and described with respect to one exemplary embodiment disclosed herein may also be combined with features disclosed and described with respect to any other exemplary embodiment or embodiments disclosed herein. Materials disclosed and described as being suitable for use with respect to one exemplary embodiment disclosed herein may also be used respect to other exemplary embodiments, and may be used with other materials disclosed and described with respect to any other exemplary embodiment or embodiments disclosed herein.

Further, it should be apparent to those skilled in the art that various changes in form and details of the invention as shown and described may be made. It is intended that such changes be included within the spirit and scope of the claims appended hereto.

The invention claimed is:

1. A device for positioning an adjustable implant device having an adjustable dimension adjacent to target tissue, comprising:
    an implant holding element configured to releasably hold said adjustable implant device, said implant device having an adjustment member operative for adjusting the dimension of the implant device;
    a rotatable adjustment tool having a distal end and a proximal end;
    a tool holding element directly attached to the rotatable adjustment tool and configured to releasably hold the adjustment tool adjacent the implant holding element and to allow rotation of the adjustment tool while so held, said adjustment tool having the distal end releasably coupled to the adjustment member and configured to adjust the dimension of said adjustable implant device by rotation of the adjustment tool while held by the tool holding element, said tool holding element coupled longitudinally moveably to said adjustment tool and said implant holding element between a first position arrangable adjacent said adjustable implant device and a second position arrangable spaced therefrom; and
    an implant securing element having a configuration effective to secure said implant to said target tissue.

2. The device of claim 1, wherein said implant securing element has a first configuration adapted for penetrating tissue and a tip portion adapted for penetrating tissue and a second configuration adapted for engaging tissue.

3. The device of claim 1, wherein the implant holding element comprises a plurality of elongated structures having a proximal end and a distal end, the distal end adapted to be releasably coupled to the adjustable implant device, and the proximal end coupled to an implant holding element guide.

4. The device of claim 3, wherein the tool holding element is coupled to the implant holding element for releasably holding the adjustment tool.

5. The device of claim 3, wherein at least one of the elongated structures is hollow and adapted for dischargeably holding the implant securing element.

6. The device of claim 1, further including an implant positioning element surrounded by the implant holding element.

7. The device of claim 6, wherein the implant positioning element comprises a plurality of flexible elongated members, and wherein the implant holding element comprises a plurality of elongated structures.

8. The device of claim 7, further including an implant holding element guide for supporting and guiding the elongated structures.

9. A system for controlling the internal perimeter of an anatomic orifice or lumen disposed adjacent target tissue, comprising:
    a rotatable adjustment tool having a distal end;
    an adjustable implant device including an adjustable perimeter and a perimeter adjustment mechanism having a docking element configured to operably engage the adjustment tool, said perimeter adjustment mechanism being operably connected with said docking element, wherein the distal end of the adjustment tool is configured to releasably engage said docking element for rotation of the docking element;
    an implant placement device comprising an implant holding element;
    an implant securing element configured to secure said adjustable implant device to said target tissue, wherein the adjustment tool is removeably coupled to the implant holding element; and
    a tool holding element attached to said adjustment tool and configured to hold said adjustment tool adjacent the implant holding element and to allow rotation thereof while so held and engaged with said docking element, said tool holding element coupled longitudinally moveably to said adjustment tool and said implant holding element between a first position arrangable adjacent said adjustable implant device and a second position arrangable spaced therefrom.

10. The system of claim 9 wherein said implant securing element comprises a tip portion configured to penetrate tissue, said implant securing element being configured to assume at least a first configuration and a second configuration, said first configuration being adapted for penetrating tissue, and said second configuration adapted for engaging tissue.

11. The device of claim 9, wherein the implant holding element comprises a plurality of elongated structures adapted to be releasably attached to the adjustable implant device.

12. The device of claim 11, further including an implant device positioning element, and wherein the implant holding element forms an enclosure surrounding the implant device positioning element.

13. The device of claim 11, wherein the elongated structures are hollow for storing the implant securing element.

14. The device of claim 9, further including an implant device positioning element comprising a plurality of flexible elements.

15. The device of claim 14, wherein the tool holding element further including a guide for guiding the implant holding element.

16. The device of claim 15, wherein the tool holding element includes an opening for the passage of the implant device positioning element.

17. A device for adjusting an adjustable implant device having an adjustable dimension, comprising:
an implant holding element having a proximal end and a distal end, the distal end adapted to be releasably coupled to an adjustable implant device, said implant device having an adjustment member operative for adjusting the dimension of the implant device;
a rotatable adjustment tool having a proximal end and a distal end, the distal end adapted to be operatively and releasably coupled to the adjustment member of the adjustable implant device for adjusting at least one of the size or shape of the adjustable implant device by rotation of the adjustment tool;
an implant positioning element surrounded by the implant holding element, wherein the implant positioning element expands and contracts responsive to the adjustment of the adjustable implant by the adjustment tool; and
a tool guide releasably attached to the adjustment tool and coupling the adjustment tool to the implant holding element, wherein the adjustment tool is rotatable for adjusting the adjustable implant device while being coupled to the implant holding element by the tool guide and coupled to the adjustment member, said tool guide coupled longitudinally moveably to said adjustment tool and said implant holding element between a first position arrangable adjacent said adjustable implant device and a second position arrangable spaced therefrom.

18. The device of claim 17, further including a plurality of securing elements for securing the adjustable implant device adjacent to an anatomical orifice or lumen.

19. A device for positioning and adjusting an adjustable implant, comprising:
an implant positioning element;
an implant holding element surrounding the implant positioning element, the implant holding element having a proximal end and a distal end, the distal end adapted to be releasably coupled to an adjustable implant; and
an adjustment tool having a proximal end and a distal end, the distal end of the adjustment tool adapted to be operatively coupled to the adjustable implant for adjusting at least one of the size or shape of the adjustable implant;
wherein the implant positioning element expands and contracts responsive to the adjustment of the adjustable implant by the adjustment tool.

20. The device of claim 19 wherein the implant positioning element comprises a plurality of elongated flexible members.

21. The device of claim 20, further including a plurality of securing elements for securing the adjustable implant adjacent to an anatomical orifice or lumen.

22. A device for adjusting an adjustable implant having an adjustable dimension, comprising;
an elongated flexible implant positioning element comprising a plurality of elongated flexible members;
an elongated implant holding element surrounding the implant positioning element, the implant holding element having a proximal end and a distal end, the distal end adapted to be releasably coupled to an adjustable implant, said implant having an adjustment member operative for adjusting the dimension of the implant;
a rotatable adjustment tool having a proximal end and a distal end, the distal end of the adjustment tool adapted to be operatively and rotatably coupled to the adjustment member of the adjustable implant for adjusting at least one of the size or shape of the adjustable implant by rotation of the adjustment tool; and
a tool guide releasably attached to the adjustment tool and coupling the adjustment tool to the implant holding element, wherein the adjustment tool is rotatable for adjusting at least one of the size or shape of the adjustable implant while being coupled to the implant holding element by the tool guide and coupled to the adjustment member, said tool guide coupled longitudinally moveably to said adjustment tool and said implant holding element between a first position arrangable adjacent said adjustable implant device and a second position arrangable spaced therefrom.

23. The device of claim 22, wherein the implant holding element comprises a plurality of elongated hollow structures adapted to dischargeably receive at least one securing element for securing the adjustable implant adjacent to an anatomical orifice or lumen.

24. A system for controlling the internal perimeter of an anatomic orifice or lumen disposed adjacent target tissue, comprising:
an adjustment tool;
an adjustable implant device having an adjustable perimeter, a perimeter adjustment mechanism, and a docking element configured to operably engage the adjustment tool, said perimeter adjustment mechanism being operably connected with said docking element, wherein the adjustment tool is configured to operably engage said docking element;
an implant placement device comprising an implant engagement element, wherein the implant engagement element comprises a plurality of elongated structures adapted to be releasably attached to the adjustable implant device; and
an implant securing element configured to secure said adjustable implant device to said target tissue, wherein the adjustment tool is removeably coupled to the implant engagement element, wherein the elongated structures are hollow for storing the implant securing element.

25. A system for controlling the internal perimeter of an anatomic orifice or lumen disposed adjacent target tissue, comprising:
an adjustment tool;
an adjustable implant device having an adjustable perimeter, a perimeter adjustment mechanism, and a docking element configured to operably engage the adjustment tool, said perimeter adjustment mechanism being operably connected with said docking element, wherein the adjustment tool is configured to operably engage said docking element;
an implant placement device comprising an implant engagement element;
an implant securing element configured to secure said adjustable implant device to said target tissue, wherein the adjustment tool is removeably coupled to the implant engagement element;
an implant device positioning element comprising a plurality of flexible elements surrounding the implant engagement element, wherein said flexible elements expand and contract responsive to the adjustment of the adjustable implant device by the adjustment tool; and
a guide for supporting and guiding the implant engagement element, wherein the guide includes an opening for the passage of the implant device positioning element.

26. A device for adjusting an adjustable implant device, comprising:

an implant holding element having a proximal end and a distal end, the distal end adapted to be releasably coupled to an adjustable implant device;

an adjustment tool having a proximal end and a distal end, the distal end adapted to be operatively coupled to the adjustable implant device for adjusting at least one of the size or shape of the adjustable implant;

a tool guide for releasably coupling the adjustment tool to the implant holding element, wherein the adjustment tool is operative for adjusting the adjustable implant while being coupled to the implant holding element by the tool guide; and an implant positioning element surrounded by the implant holding element, wherein the implant positioning element expands and contracts responsive to the adjustment of the adjustable implant by the adjustment tool.

27. A device for adjusting an adjustable implant, comprising;

an elongated flexible implant positioning element;

an elongated implant holding element surrounding the implant positioning element, the implant holding element having a proximal end and a distal end, the distal end adapted to be releasably coupled to an adjustable implant, wherein the implant holding element comprises a plurality of elongated hollow structures adapted to dischargeably receive at least one securing element for securing the adjustable implant adjacent to an anatomical orifice or lumen;

an adjustment tool having a proximal end and a distal end, the distal end of the adjustment tool adapted to be operatively coupled to the adjustable implant for adjusting at least one of the size or shape of the adjustable implant; and a tool guide for releasably coupling the adjustment tool to the implant holding element, wherein the adjustment tool is operative for adjusting at least one of the size or shape of the adjustable implant while being coupled to the implant holding element by the tool guide.

28. A device for positioning an adjustable implant device adjacent to target tissue, comprising:

an implant holding element configured to releasably hold said adjustable implant device;

a tool holding element configured to hold an adjustment tool adjacent the implant holding element and to allow operation thereof while so held, said adjustment tool being configured to adjust said adjustable implant device;

an implant securing element having a configuration effective to secure said implant to said target tissue; and an implant positioning element surrounded by the implant holding element, wherein the implant positioning element expands and contracts responsive to the adjustment of the adjustable implant by the adjustment tool.

29. A system for controlling the internal perimeter of an anatomic orifice or lumen disposed adjacent target tissue, comprising:

an adjustment tool;

an adjustable implant device having an adjustable perimeter, a perimeter adjustment mechanism, and a docking element configured to operably engage the adjustment tool, said perimeter adjustment mechanism being operably connected with said docking element, wherein the adjustment tool is configured to operably engage said docking element;

an implant placement device comprising an implant engagement element;

an implant securing element configured to secure said adjustable implant device to said target tissue, wherein the adjustment tool is removeably coupled to the implant engagement element; and an implant device positioning element, wherein the implant engagement element forms an enclosure surrounding the implant device positioning element, wherein the implant positioning element expands and contracts responsive to the adjustment of the adjustable implant by the adjustment tool.

30. A device for adjusting an adjustable implant, comprising;

an elongated flexible implant positioning element;

an elongated implant holding element surrounding the implant positioning element, the implant holding element having a proximal end and a distal end, the distal end adapted to be releasably coupled to an adjustable implant;

an adjustment tool having a proximal end and a distal end, the distal end of the adjustment tool adapted to be operatively coupled to the adjustable implant for adjusting at least one of the size or shape of the adjustable implant; and a tool guide for releasably coupling the adjustment tool to the implant holding element, wherein the adjustment tool is operative for adjusting at least one of the size or shape of the adjustable implant while being coupled to the implant holding element by the tool guide, wherein the implant positioning element expands and contracts responsive to the adjustment of the adjustable implant by the adjustment tool.

31. A device for positioning an adjustable implant device adjacent to target tissue, comprising:

an implant holding element configured to releasably hold said adjustable implant device, wherein the implant holding element comprises a plurality of elongated structures;

an implant positioning element surrounded by the implant holding element, wherein the implant positioning element comprises a plurality of flexible elongated members;

an adjustment tool configured to adjust said adjustable implant device;

a tool holding element configured to hold the adjustment tool adjacent the implant holding element and to allow operation of the adjustment tool while so held, said tool holding element coupled longitudinally moveable to said adjustment tool and said implant holding element between a first position arrangable adjacent said adjustable implant device and a second position arrangable spaced therefrom; and an implant securing element having a configuration effective to secure said implant to said target tissue.

32. A device for adjusting an adjustable implant device, comprising:

an implant holding element having a proximal end and a distal end, the distal end adapted to be releasably coupled to an adjustable implant device;

an adjustment tool having a proximal end and a distal end, the distal end adapted to be operatively coupled to the adjustable implant device for adjusting at least one of the size or shape of the adjustable implant device;

an implant positioning element surrounded by the implant holding element, wherein the implant positioning element expands and contracts responsive to the adjustment of the adjustable implant by the adjustment tool; and a tool guide for releasably coupling the adjustment tool to the implant holding element, wherein the adjustment tool is operative for adjusting the adjustable implant device while being coupled to the implant holding element by the tool guide, said tool guide coupled longitudinally moveable to said adjustment tool and said implant holding element between a first position arrangable adjacent said adjustable implant device and a second position arrangable spaced therefrom.

* * * * *